US008426366B2

(12) United States Patent
Hillman

(10) Patent No.: US 8,426,366 B2
(45) Date of Patent: Apr. 23, 2013

(54) DISEASE TREATMENT VIA ANTIMICROBIAL PEPTIDES OR THEIR INHIBITORS

(76) Inventor: Yitzchak Hillman, Jerusalem (IL)

( * ) Notice: Subject to any disclaimer, the term of this patent is extended or adjusted under 35 U.S.C. 154(b) by 0 days.

(21) Appl. No.: 13/459,191

(22) Filed: Apr. 29, 2012

(65) Prior Publication Data

US 2012/0277157 A1 Nov. 1, 2012

Related U.S. Application Data

(60) Division of application No. 12/173,344, filed on Jul. 15, 2008, now Pat. No. 8,202,835, which is a continuation-in-part of application No. 10/539,558, filed on Jun. 17, 2005, now abandoned.

(30) Foreign Application Priority Data

Jul. 15, 2007 (IL) .......................................... 184611
Nov. 26, 2007 (IL) .......................................... 187627

(51) Int. Cl.
*A61K 38/16* (2006.01)
(52) U.S. Cl.
USPC ........... 514/16.6; 514/16.8; 514/2.4; 514/2.8; 514/12.2; 514/21.3
(58) Field of Classification Search .................. None
See application file for complete search history.

(56) References Cited

U.S. PATENT DOCUMENTS

| 6,335,318 B1 | 1/2002 | Selsted |
| 2002/0072495 A1 | 6/2002 | Chertov |

FOREIGN PATENT DOCUMENTS

| WO | WO 94/12206 A1 | 6/1994 |
| WO | WO 95/11670 A1 | 5/1995 |
| WO | WO 98/07833 A1 | 2/1998 |
| WO | WO 99/11663 A1 | 3/1999 |
| WO | WO 99/15548 A1 | 4/1999 |
| WO | WO 02/04487 A1 | 1/2002 |
| WO | WO 2004/006725 A | 1/2004 |
| WO | WO 2004/056307 A | 7/2004 |
| WO | WO 2004/063219 A1 | 7/2004 |
| WO | WO 2004/067025 A | 8/2004 |
| WO | WO 2004/098536 A1 | 11/2004 |
| WO | WO 2005/040201 A | 5/2005 |

OTHER PUBLICATIONS

Paulsen et al. ("Antimicrobial peptides are expressed and produced in healthy and inflamed human synovial membranes," J Pathol 2002; 198: 369-377.*
Joseph F. Gera et al. Human Neutrophil Peptide Defensins Induce Single Strand DNA Breaks in Target Cells. Cellular Immunology 138, 108-120 (1991) USA.
Alan K. Lichstenstein et al. Synergic Cytolysis Mediated by Hydrogen Peroxide Combined with peptide Defensins. Cellular immunology 114, 104-116 (1988) USA.
Murphy C. J. et al. Defensins are Mitogenic for epithelial cells and fibroblasts. Journal of cellular Physiology 155, 408-413 (1993) USA.
Brogden K.A. et al. The Ovine Cathelicidin SMAP29 Kills Ovine Respiratory Pathogens in vitro and in an Ovine model of Pulmonary Infection. Antimicrobial Agents and Chemotherapy vol. 45, No. 1, Jan. 2001 p. 331-334 USA.
Tomas Ganz et al. Defensins Pharmac Ther. vol. 66 pp. 191-205, 1995 GB.
Haibo Zhang et al. Neutrophil defensins mediate acute inflammatory response and lung dysfunction in dose-related fashion. American Journal of Physiology, Lung Cell Mol Physiol. 280, pt. 1 : L974-L954, 2001. USA.
Koichi Sawak et al. Concentration of Beta-Defensin-2 in Oral Squamous Cell Carcinoma Anticancer Research 22: 4 2103-2108 (2002).
Mueller Claudia A et al: "Human alpha-defensins HNPs-1, -2, and -3 in renal cell carcinoma: Influences on tumor cell proliferation" American Journal of Pathology, vol. 160, No. 4, Apr. 2002, pp. 1311-1324, XP002469449 ISSN: 0002-9440 USA.
McKay MS et al. Immunomagnetic recovery of human neutrophil defensins from human gingival crevices. Oral microbiaol. Immunol. 1999, 14(3), 190-193.
Gallo Richard L et al: "Endogenous production of antimicrobial peptides in innate immunity and human disease." Current Allergy and Asthma Reports Sep. 2003, vol. 3, No. 5, Sep. 2003, pp. 402-409, XP009096110 ISSN: 1529-7322.
Sawaki Koichi et al: "High concentration of beta-defensin-2 in oral squamous cell carcinoma" Anticancer Research, vol. 22, No. 4, Jul. 2002, pp. 2103-2108, XP009096121 ISSN: 0250-7005.
Oh-I T et al: "Significant increase in an antimicrobial peptide, human beta-defensin-2 (hBD-2) in scales in patients with psoriasis: Comparison with one in scales of skin diseases and in healthy horny layers" Pharmacology Reviews and Communications 2001 United Kingdom, vol. 11, No. 4, 2001, pp. 329-333, XP009096120 ISSN: 1028-8945.
Ong P Y et al: "Endogenous Antimicrobial Peptides and Skin Infections in Atopic Dermatitis" New England Journal of Medicine, The, Massachusetts Medical Society, Waltham, MA, US, vol. 347, No. 15, Oct. 10, 2002, pp. 1151-1160, XP008028910 ISSN: 0028-4793.
Japanese office action issued by the JPO on Mar. 2, 2010 in connection with Appl. No. 2005-502611.
China office action issued by the CPO in on Oct. 23, 2009 in connection with Appl. No. 200380105021X.
Australia office action issued by the APO in on Sep. 7, 2009 in connection with Appl. No. 2003288507.
European office action issued by the EPO in on Sep. 3, 2008 in connection with Appl. No. 03780582.7-2402.
Mexico office action issued by the EPO in on Jul. 30, 2009 in connection with Appl. No. MX/2009/042037.

* cited by examiner

*Primary Examiner* — Christina Bradley

(57) ABSTRACT

Provided are methods for the treatment of disease and promotion of healing that include providing a therapeutically effective amount of a mammalian antimicrobial peptide (AMP) or analog thereof, in particular a cathelicidin or cathelicidin fragment or cathelicidin analog, thereby treating the disease in the subject in need thereof. Also provided are specific analogs or fragments of cathelicidin that function as agonists, as do endogenous cathelicidins, or as either dominant negatives or as inhibitors to endogenous cathelicidin or to other endogenous AMPs or that compete with pro-inflammatory agents or fragments of AMPs on cognate receptors without inducing disease.

6 Claims, 16 Drawing Sheets

Cathelicidin vs. PBS Treatment Results

| Group No. | Test material | Incidence | Mortality at day 50 | Summary clinical score (average) | Average score at first peak of disease |
|---|---|---|---|---|---|
| 1 | PBS | 3/6 | 3/6 | 50.9 | 2.0 |
| 2 | Cathelicidin | 3/6 | 0/6 | 26.8 | 1.16 |
| 3 | Cathelicidin | 3/6 | 0/6 | 17.2 | 1.16 |

EAE Clinical score chart

P-0702 - Cathelicidin of sequence: GLLRKGGEKIGEKLKKIGQKIKNFFQKLVPQPEQ

PBS Control on Day 49

Low dose cathelicidin - All EAE affected mice survived by day 49. EAE severity decreased with time.

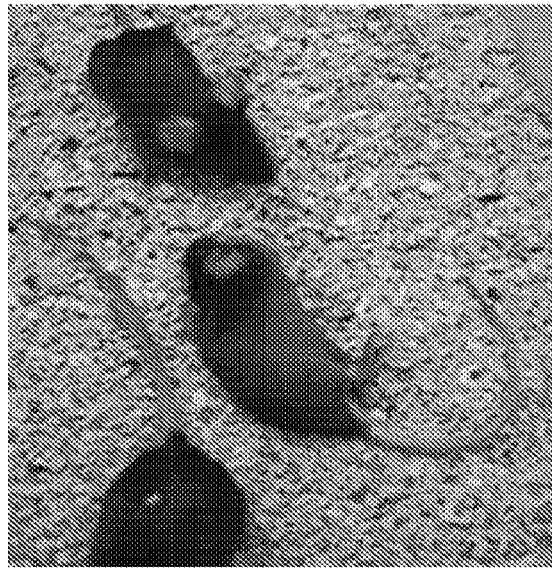
Two examples of EAE mice with paralyzed hind legs and tail
FIG. 9C Western blot analysis of four different scFv antibodies to LL-37

Binding of LL37 to scFv

Inhibition of bacterial killing by humanized antibody scFv.

FIG. 11

| Mouse | Paw | Arthritic severity index / Days since incidence | 1 | 3 | 7 | 9 | 11 | 14 | 16 | 18 | 21 | 23 | 25 | 28 | 30 | 32 | |
|---|---|---|---|---|---|---|---|---|---|---|---|---|---|---|---|---|---|
| 3 | RF | | 2 | 3 | 2 | 4 | 4 | 4 | 4 | 4 | 3 | 3 | 3 | 3 | 3 | 3 | Treatment |
| 3 | LF | | 3 | 4 | 4 | 4 | 4 | 4 | 4 | 4 | 3 | 3 | 3 | 3 | 3 | 3 | Treatment |
| 22 | LF | | 4 | 4 | 4 | 4 | 4 | 4 | 4 | 3 | 3 | 3 | 3 | 3 | 3 | 3 | control |
| 17 | RF | | 1 | 4 | 4 | 4 | 4 | 4 | 4 | 4 | 3 | 3 | 3 | 3 | 3 | 3 | control |

FIG. 15A

| mouse | paw | |
|---|---|---|
| 5 | LF | treatment |
| 8 | LF | treatment |
| 8 | RF | treatment |
| 12 | LF | control |
| 16 | RF | control |
| 18 | RH | Control – non inflamed |
| 18 | LH | Control – non inflamed |
| 13 | RH | Control - non inflamed |
| 13 | LH | Control - non inflamed |
| 10 | RH | Treatment- non inflamed |

Key: LF = Left Front paw
RF = Right Front paw
LH = Left Hind paw
RH = Right Hind paw

FIG. 15B

Mouse 3 Right Front paw. TRAP
Arrow shows one osteoclast

Mouse 3 Right Front Paw.
Staining by H&E

Control – Non-inflamed mouse 13 Right Hind after TRAP staining

Control inflamed- mouse 17 Right Front paw after TRAP staining

SEQUENCE LISTING

```
<160> NUMBER OF SEQ ID NOS: 98

<210> SEQ ID NO 1
<211> LENGTH: 50
<212> TYPE: PRT
<213> ORGANISM: Homo sapiens

<400> SEQUENCE: 1

Phe Asp Ile Ser Cys Asp Lys Asp Asn Lys Arg Phe Ala Leu Leu Gly
1               5                   10                  15

Asp Phe Phe Arg Lys Ser Lys Glu Lys Ile Gly Lys Glu Phe Lys Arg
            20                  25                  30

Ile Val Gln Arg Ile Lys Asp Phe Leu Arg Asn Leu Val Pro Arg Thr
        35                  40                  45

Glu Ser
```

50

<210> SEQ ID NO 2
<211> LENGTH: 49
<212> TYPE: PRT
<213> ORGANISM: Homo sapiens

<400> SEQUENCE: 2

Asp Ile Ser Cys Asp Lys Asp Asn Lys Arg Phe Ala Leu Leu Gly Asp
1               5                   10                  15

Phe Phe Arg Lys Ser Lys Glu Lys Ile Gly Lys Glu Phe Lys Arg Ile
                20                  25                  30

Val Gln Arg Ile Lys Asp Phe Leu Arg Asn Leu Val Pro Arg Thr Glu
            35                  40                  45

Ser

<210> SEQ ID NO 3
<211> LENGTH: 48
<212> TYPE: PRT
<213> ORGANISM: Homo sapiens

<400> SEQUENCE: 3

Ile Ser Cys Asp Lys Asp Asn Lys Arg Phe Ala Leu Leu Gly Asp Phe
1               5                   10                  15

Phe Arg Lys Ser Lys Glu Lys Ile Gly Lys Glu Phe Lys Arg Ile Val
                20                  25                  30

Gln Arg Ile Lys Asp Phe Leu Arg Asn Leu Val Pro Arg Thr Glu Ser
            35                  40                  45

<210> SEQ ID NO 4
<211> LENGTH: 47
<212> TYPE: PRT
<213> ORGANISM: Homo sapiens

<400> SEQUENCE: 4

Ser Cys Asp Lys Asp Asn Lys Arg Phe Ala Leu Leu Gly Asp Phe Phe
1               5                   10                  15

Arg Lys Ser Lys Glu Lys Ile Gly Lys Glu Phe Lys Arg Ile Val Gln
                20                  25                  30

Arg Ile Lys Asp Phe Leu Arg Asn Leu Val Pro Arg Thr Glu Ser
            35                  40                  45

<210> SEQ ID NO 5
<211> LENGTH: 46
<212> TYPE: PRT
<213> ORGANISM: Homo sapiens

<400> SEQUENCE: 5

Cys Asp Lys Asp Asn Lys Arg Phe Ala Leu Leu Gly Asp Phe Phe Arg
1               5                   10                  15

Lys Ser Lys Glu Lys Ile Gly Lys Glu Phe Lys Arg Ile Val Gln Arg
                20                  25                  30

Ile Lys Asp Phe Leu Arg Asn Leu Val Pro Arg Thr Glu Ser
            35                  40                  45

<210> SEQ ID NO 6
<211> LENGTH: 45
<212> TYPE: PRT
<213> ORGANISM: Homo sapiens

<400> SEQUENCE: 6

Asp Lys Asp Asn Lys Arg Phe Ala Leu Leu Gly Asp Phe Phe Arg Lys
1               5                   10                  15

Ser Lys Glu Lys Ile Gly Lys Glu Phe Lys Arg Ile Val Gln Arg Ile
            20                  25                  30

Lys Asp Phe Leu Arg Asn Leu Val Pro Arg Thr Glu Ser
    35                  40                  45

<210> SEQ ID NO 7
<211> LENGTH: 44
<212> TYPE: PRT
<213> ORGANISM: Homo sapiens

<400> SEQUENCE: 7

Lys Asp Asn Lys Arg Phe Ala Leu Leu Gly Asp Phe Phe Arg Lys Ser
1               5                   10                  15

Lys Glu Lys Ile Gly Lys Glu Phe Lys Arg Ile Val Gln Arg Ile Lys
            20                  25                  30

Asp Phe Leu Arg Asn Leu Val Pro Arg Thr Glu Ser
    35                  40

<210> SEQ ID NO 8
<211> LENGTH: 43
<212> TYPE: PRT
<213> ORGANISM: Homo sapiens

<400> SEQUENCE: 8

Asp Asn Lys Arg Phe Ala Leu Leu Gly Asp Phe Phe Arg Lys Ser Lys
1               5                   10                  15

Glu Lys Ile Gly Lys Glu Phe Lys Arg Ile Val Gln Arg Ile Lys Asp
            20                  25                  30

Phe Leu Arg Asn Leu Val Pro Arg Thr Glu Ser
    35                  40

<210> SEQ ID NO 9
<211> LENGTH: 42
<212> TYPE: PRT
<213> ORGANISM: Homo sapiens

<400> SEQUENCE: 9

Asn Lys Arg Phe Ala Leu Leu Gly Asp Phe Phe Arg Lys Ser Lys Glu
1               5                   10                  15

Lys Ile Gly Lys Glu Phe Lys Arg Ile Val Gln Arg Ile Lys Asp Phe
            20                  25                  30

Leu Arg Asn Leu Val Pro Arg Thr Glu Ser
    35                  40

<210> SEQ ID NO 10
<211> LENGTH: 41
<212> TYPE: PRT
<213> ORGANISM: Homo sapiens

<400> SEQUENCE: 10

Lys Arg Phe Ala Leu Leu Gly Asp Phe Phe Arg Lys Ser Lys Glu Lys
1               5                   10                  15

Ile Gly Lys Glu Phe Lys Arg Ile Val Gln Arg Ile Lys Asp Phe Leu
            20                  25                  30

Arg Asn Leu Val Pro Arg Thr Glu Ser
    35                  40

<210> SEQ ID NO 11
<211> LENGTH: 40

```
<212> TYPE: PRT
<213> ORGANISM: Homo sapiens

<400> SEQUENCE: 11

Arg Phe Ala Leu Leu Gly Asp Phe Phe Arg Lys Ser Lys Glu Lys Ile
1               5                   10                  15

Gly Lys Glu Phe Lys Arg Ile Val Gln Arg Ile Lys Asp Phe Leu Arg
            20                  25                  30

Asn Leu Val Pro Arg Thr Glu Ser
        35                  40

<210> SEQ ID NO 12
<211> LENGTH: 39
<212> TYPE: PRT
<213> ORGANISM: Homo sapiens

<400> SEQUENCE: 12

Phe Ala Leu Leu Gly Asp Phe Phe Arg Lys Ser Lys Glu Lys Ile Gly
1               5                   10                  15

Lys Glu Phe Lys Arg Ile Val Gln Arg Ile Lys Asp Phe Leu Arg Asn
            20                  25                  30

Leu Val Pro Arg Thr Glu Ser
        35

<210> SEQ ID NO 13
<211> LENGTH: 38
<212> TYPE: PRT
<213> ORGANISM: Homo sapiens

<400> SEQUENCE: 13

Ala Leu Leu Gly Asp Phe Phe Arg Lys Ser Lys Glu Lys Ile Gly Lys
1               5                   10                  15

Glu Phe Lys Arg Ile Val Gln Arg Ile Lys Asp Phe Leu Arg Asn Leu
            20                  25                  30

Val Pro Arg Thr Glu Ser
        35

<210> SEQ ID NO 14
<211> LENGTH: 37
<212> TYPE: PRT
<213> ORGANISM: Homo sapiens

<400> SEQUENCE: 14

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
        35

<210> SEQ ID NO 15
<211> LENGTH: 36
<212> TYPE: PRT
<213> ORGANISM: Homo sapiens

<400> SEQUENCE: 15

Leu Gly Asp Phe Phe Arg Lys Ser Lys Glu Lys Ile Gly Lys Glu Phe
1               5                   10                  15

Lys Arg Ile Val Gln Arg Ile Lys Asp Phe Leu Arg Asn Leu Val Pro
            20                  25                  30

Arg Thr Glu Ser
```

```
<210> SEQ ID NO 16
<211> LENGTH: 35
<212> TYPE: PRT
<213> ORGANISM: Homo sapiens

<400> SEQUENCE: 16

Gly Asp Phe Phe Arg Lys Ser Lys Glu Lys Ile Gly Lys Glu Phe Lys
1               5                   10                  15

Arg Ile Val Gln Arg Ile Lys Asp Phe Leu Arg Asn Leu Val Pro Arg
            20                  25                  30

Thr Glu Ser
        35

<210> SEQ ID NO 17
<211> LENGTH: 34
<212> TYPE: PRT
<213> ORGANISM: Homo sapiens

<400> SEQUENCE: 17

Asp Phe Phe Arg Lys Ser Lys Glu Lys Ile Gly Lys Glu Phe Lys Arg
1               5                   10                  15

Ile Val Gln Arg Ile Lys Asp Phe Leu Arg Asn Leu Val Pro Arg Thr
            20                  25                  30

Glu Ser

<210> SEQ ID NO 18
<211> LENGTH: 33
<212> TYPE: PRT
<213> ORGANISM: Homo sapiens

<400> SEQUENCE: 18

Phe Phe Arg Lys Ser Lys Glu Lys Ile Gly Lys Glu Phe Lys Arg Ile
1               5                   10                  15

Val Gln Arg Ile Lys Asp Phe Leu Arg Asn Leu Val Pro Arg Thr Glu
            20                  25                  30

Ser

<210> SEQ ID NO 19
<211> LENGTH: 32
<212> TYPE: PRT
<213> ORGANISM: Homo sapiens

<400> SEQUENCE: 19

Phe Arg Lys Ser Lys Glu Lys Ile Gly Lys Glu Phe Lys Arg Ile Val
1               5                   10                  15

Gln Arg Ile Lys Asp Phe Leu Arg Asn Leu Val Pro Arg Thr Glu Ser
            20                  25                  30

<210> SEQ ID NO 20
<211> LENGTH: 31
<212> TYPE: PRT
<213> ORGANISM: Homo sapiens

<400> SEQUENCE: 20

Arg Lys Ser Lys Glu Lys Ile Gly Lys Glu Phe Lys Arg Ile Val Gln
1               5                   10                  15

Arg Ile Lys Asp Phe Leu Arg Asn Leu Val Pro Arg Thr Glu Ser
            20                  25                  30
```

<210> SEQ ID NO 21
<211> LENGTH: 30
<212> TYPE: PRT
<213> ORGANISM: Homo sapiens

<400> SEQUENCE: 21

Lys Ser Lys Glu Lys Ile Gly Lys Glu Phe Lys Arg Ile Val Gln Arg
1               5                   10                  15

Ile Lys Asp Phe Leu Arg Asn Leu Val Pro Arg Thr Glu Ser
            20                  25                  30

<210> SEQ ID NO 22
<211> LENGTH: 29
<212> TYPE: PRT
<213> ORGANISM: Homo sapiens

<400> SEQUENCE: 22

Ser Lys Glu Lys Ile Gly Lys Glu Phe Lys Arg Ile Val Gln Arg Ile
1               5                   10                  15

Lys Asp Phe Leu Arg Asn Leu Val Pro Arg Thr Glu Ser
            20                  25

<210> SEQ ID NO 23
<211> LENGTH: 36
<212> TYPE: PRT
<213> ORGANISM: Homo sapiens

<400> SEQUENCE: 23

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu
        35

<210> SEQ ID NO 24
<211> LENGTH: 35
<212> TYPE: PRT
<213> ORGANISM: Homo sapiens

<400> SEQUENCE: 24

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr
        35

<210> SEQ ID NO 25
<211> LENGTH: 34
<212> TYPE: PRT
<213> ORGANISM: Homo sapiens

<400> SEQUENCE: 25

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg

<210> SEQ ID NO 26
<211> LENGTH: 33

-continued

```
<212> TYPE: PRT
<213> ORGANISM: Homo sapiens

<400> SEQUENCE: 26

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro

<210> SEQ ID NO 27
<211> LENGTH: 32
<212> TYPE: PRT
<213> ORGANISM: Homo sapiens

<400> SEQUENCE: 27

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

<210> SEQ ID NO 28
<211> LENGTH: 31
<212> TYPE: PRT
<213> ORGANISM: Homo sapiens

<400> SEQUENCE: 28

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu
            20                  25                  30

<210> SEQ ID NO 29
<211> LENGTH: 30
<212> TYPE: PRT
<213> ORGANISM: Homo sapiens

<400> SEQUENCE: 29

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn
            20                  25                  30

<210> SEQ ID NO 30
<211> LENGTH: 29
<212> TYPE: PRT
<213> ORGANISM: Homo sapiens

<400> SEQUENCE: 30

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg
            20                  25

<210> SEQ ID NO 31
<211> LENGTH: 28
<212> TYPE: PRT
<213> ORGANISM: Homo sapiens

<400> SEQUENCE: 31

Leu Leu Gly Asp Phe Phe Arg Lys Ser Lys Glu Lys Ile Gly Lys Glu
1               5                   10                  15
```

```
Phe Lys Arg Ile Val Gln Arg Ile Lys Asp Phe Leu
            20                  25

<210> SEQ ID NO 32
<211> LENGTH: 27
<212> TYPE: PRT
<213> ORGANISM: Homo sapiens

<400> SEQUENCE: 32

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe
            20                  25

<210> SEQ ID NO 33
<211> LENGTH: 26
<212> TYPE: PRT
<213> ORGANISM: Homo sapiens

<400> SEQUENCE: 33

Leu Leu Gly Asp Phe Phe Arg Lys Ser Lys Glu Lys Ile Gly Lys Glu
1               5                   10                  15

Phe Lys Arg Ile Val Gln Arg Ile Lys Asp
            20                  25

<210> SEQ ID NO 34
<211> LENGTH: 25
<212> TYPE: PRT
<213> ORGANISM: Homo sapiens

<400> SEQUENCE: 34

Leu Leu Gly Asp Phe Phe Arg Lys Ser Lys Glu Lys Ile Gly Lys Glu
1               5                   10                  15

Phe Lys Arg Ile Val Gln Arg Ile Lys
            20                  25

<210> SEQ ID NO 35
<211> LENGTH: 24
<212> TYPE: PRT
<213> ORGANISM: Homo sapiens

<400> SEQUENCE: 35

Leu Leu Gly Asp Phe Phe Arg Lys Ser Lys Glu Lys Ile Gly Lys Glu
1               5                   10                  15

Phe Lys Arg Ile Val Gln Arg Ile
            20

<210> SEQ ID NO 36
<211> LENGTH: 23
<212> TYPE: PRT
<213> ORGANISM: Homo sapiens

<400> SEQUENCE: 36

Leu Leu Gly Asp Phe Phe Arg Lys Ser Lys Glu Lys Ile Gly Lys Glu
1               5                   10                  15

Phe Lys Arg Ile Val Gln Arg
            20

<210> SEQ ID NO 37
<211> LENGTH: 22
<212> TYPE: PRT
<213> ORGANISM: Homo sapiens

<400> SEQUENCE: 37
```

-continued

```
Leu Leu Gly Asp Phe Phe Arg Lys Ser Lys Glu Lys Ile Gly Lys Glu
1               5                   10                  15

Phe Lys Arg Ile Val Gln
            20

<210> SEQ ID NO 38
<211> LENGTH: 21
<212> TYPE: PRT
<213> ORGANISM: Homo sapiens

<400> SEQUENCE: 38

Leu Leu Gly Asp Phe Phe Arg Lys Ser Lys Glu Lys Ile Gly Lys Glu
1               5                   10                  15

Phe Lys Arg Ile Val
            20

<210> SEQ ID NO 39
<211> LENGTH: 20
<212> TYPE: PRT
<213> ORGANISM: Homo sapiens

<400> SEQUENCE: 39

Leu Leu Gly Asp Phe Phe Arg Lys Ser Lys Glu Lys Ile Gly Lys Glu
1               5                   10                  15

Phe Lys Arg Ile
            20

<210> SEQ ID NO 40
<211> LENGTH: 6
<212> TYPE: PRT
<213> ORGANISM: Homo sapiens

<400> SEQUENCE: 40

Glu Phe Lys Arg Ile Val
1               5

<210> SEQ ID NO 41
<211> LENGTH: 8
<212> TYPE: PRT
<213> ORGANISM: Homo sapiens

<400> SEQUENCE: 41

Lys Glu Phe Lys Arg Ile Val Gln
1               5

<210> SEQ ID NO 42
<211> LENGTH: 10
<212> TYPE: PRT
<213> ORGANISM: Homo sapiens

<400> SEQUENCE: 42

Gly Lys Glu Phe Lys Arg Ile Val Gln Arg
1               5                   10

<210> SEQ ID NO 43
<211> LENGTH: 12
<212> TYPE: PRT
<213> ORGANISM: Homo sapiens

<400> SEQUENCE: 43

Ile Gly Lys Glu Phe Lys Arg Ile Val Gln Arg Ile
1               5                   10
```

```
<210> SEQ ID NO 44
<211> LENGTH: 14
<212> TYPE: PRT
<213> ORGANISM: Homo sapiens

<400> SEQUENCE: 44

Lys Ile Gly Lys Glu Phe Lys Arg Ile Val Gln Arg Ile Lys
1               5                   10

<210> SEQ ID NO 45
<211> LENGTH: 16
<212> TYPE: PRT
<213> ORGANISM: Homo sapiens

<400> SEQUENCE: 45

Glu Lys Ile Gly Lys Glu Phe Lys Arg Ile Val Gln Arg Ile Lys Asp
1               5                   10                  15

<210> SEQ ID NO 46
<211> LENGTH: 18
<212> TYPE: PRT
<213> ORGANISM: Homo sapiens

<400> SEQUENCE: 46

Lys Glu Lys Ile Gly Lys Glu Phe Lys Arg Ile Val Gln Arg Ile Lys
1               5                   10                  15

Asp Phe

<210> SEQ ID NO 47
<211> LENGTH: 20
<212> TYPE: PRT
<213> ORGANISM: Homo sapiens

<400> SEQUENCE: 47

Ser Lys Glu Lys Ile Gly Lys Glu Phe Lys Arg Ile Val Gln Arg Ile
1               5                   10                  15

Lys Asp Phe Leu
            20

<210> SEQ ID NO 48
<211> LENGTH: 29
<212> TYPE: PRT
<213> ORGANISM: Homo sapiens

<400> SEQUENCE: 48

Ser Lys Glu Lys Ile Gly Lys Glu Phe Lys Arg Ile Val Gln Arg Ile
1               5                   10                  15

Lys Asp Phe Leu Arg Asn Leu Val Pro Arg Thr Glu Ser
            20                  25

<210> SEQ ID NO 49
<211> LENGTH: 22
<212> TYPE: PRT
<213> ORGANISM: Homo sapiens

<400> SEQUENCE: 49

Lys Ser Lys Glu Lys Ile Gly Lys Glu Phe Lys Arg Ile Val Gln Arg
1               5                   10                  15

Ile Lys Asp Phe Leu Arg
            20

<210> SEQ ID NO 50
<211> LENGTH: 24
<212> TYPE: PRT
```

<213> ORGANISM: Homo sapiens

<400> SEQUENCE: 50

Arg Lys Ser Lys Glu Lys Ile Gly Lys Glu Phe Lys Arg Ile Val Gln
1               5                   10                  15

Arg Ile Lys Asp Phe Leu Arg Asn
            20

<210> SEQ ID NO 51
<211> LENGTH: 26
<212> TYPE: PRT
<213> ORGANISM: Homo sapiens

<400> SEQUENCE: 51

Phe Arg Lys Ser Lys Glu Lys Ile Gly Lys Glu Phe Lys Arg Ile Val
1               5                   10                  15

Gln Arg Ile Lys Asp Phe Leu Arg Asn Leu
            20                  25

<210> SEQ ID NO 52
<211> LENGTH: 28
<212> TYPE: PRT
<213> ORGANISM: Homo sapiens

<400> SEQUENCE: 52

Phe Phe Arg Lys Ser Lys Glu Lys Ile Gly Lys Glu Phe Lys Arg Ile
1               5                   10                  15

Val Gln Arg Ile Lys Asp Phe Leu Arg Asn Leu Val
            20                  25

<210> SEQ ID NO 53
<211> LENGTH: 30
<212> TYPE: PRT
<213> ORGANISM: Homo sapiens

<400> SEQUENCE: 53

Asp Phe Phe Arg Lys Ser Lys Glu Lys Ile Gly Lys Glu Phe Lys Arg
1               5                   10                  15

Ile Val Gln Arg Ile Lys Asp Phe Leu Arg Asn Leu Val Pro
            20                  25                  30

<210> SEQ ID NO 54
<211> LENGTH: 32
<212> TYPE: PRT
<213> ORGANISM: Homo sapiens

<400> SEQUENCE: 54

Gly Asp Phe Phe Arg Lys Ser Lys Glu Lys Ile Gly Lys Glu Phe Lys
1               5                   10                  15

Arg Ile Val Gln Arg Ile Lys Asp Phe Leu Arg Asn Leu Val Pro Arg
            20                  25                  30

<210> SEQ ID NO 55
<211> LENGTH: 34
<212> TYPE: PRT
<213> ORGANISM: Homo sapiens

<400> SEQUENCE: 55

Leu Gly Asp Phe Phe Arg Lys Ser Lys Glu Lys Ile Gly Lys Glu Phe
1               5                   10                  15

Lys Arg Ile Val Gln Arg Ile Lys Asp Phe Leu Arg Asn Leu Val Pro
            20                  25                  30

-continued

Arg Thr

<210> SEQ ID NO 56
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(28)
<223> OTHER INFORMATION: Any amino acid and this region may encompass
      0-16 residues

<400> SEQUENCE: 56

Phe Ala Leu Leu Gly Asp Phe Phe Arg Lys Ser Lys Xaa Xaa Xaa Xaa
1               5                   10                  15

Xaa Xaa Xaa Xaa Xaa Xaa Xaa Xaa Xaa Xaa Xaa Xaa
            20                  25

<210> SEQ ID NO 57
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(16)
<223> OTHER INFORMATION: Any amino acid and this region may encompass
      0-16 residues
<220> FEATURE:
<221> NAME/KEY: MOD_RES
<222> LOCATION: (27)..(34)
<223> OTHER INFORMATION: Any amino acid and this region may encompass
      0-8 residues

<400> SEQUENCE: 57

Xaa Xaa Xaa Xaa Xaa Xaa Xaa Xaa Xaa Xaa Xaa Xaa Xaa Xaa Xaa Xaa
1               5                   10                  15

Ile Gly Lys Glu Phe Lys Arg Ile Val Gln Xaa Xaa Xaa Xaa Xaa Xaa
            20                  25                  30

Xaa Xaa

<210> SEQ ID NO 58
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(19)
<223> OTHER INFORMATION: Any amino acid and this region may encompass
      0-19 residues
<220> FEATURE:
<221> NAME/KEY: MOD_RES
<222> LOCATION: (30)..(36)
<223> OTHER INFORMATION: Any amino acid and this region may encompass
      0-7 residues

<400> SEQUENCE: 58

Xaa Xaa Xaa Xaa Xaa Xaa Xaa Xaa Xaa Xaa Xaa Xaa Xaa Xaa Xaa Xaa
1               5                   10                  15

Xaa Xaa Xaa Val Gln Arg Ile Lys Asp Phe Leu Arg Asn Xaa Xaa Xaa
            20                  25                  30

Xaa Xaa Xaa Xaa
        35

<210> SEQ ID NO 59
<211> LENGTH: 43
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(19)
<223> OTHER INFORMATION: Any amino acid and this region may encompass
      0-19 residues
<220> FEATURE:
<221> NAME/KEY: MOD_RES
<222> LOCATION: (37)..(43)
<223> OTHER INFORMATION: Any amino acid and this region may encompass
      0-7 residues

<400> SEQUENCE: 59

Xaa Xaa Xaa Xaa Xaa Xaa Xaa Xaa Xaa Xaa Xaa Xaa Xaa Xaa Xaa Xaa
1               5                   10                  15

Xaa Xaa Xaa Gly Lys Glu Phe Lys Arg Ile Val Gln Arg Ile Lys Asp
            20                  25                  30

Phe Leu Arg Asn Xaa Xaa Xaa Xaa Xaa Xaa Xaa
        35                  40

<210> SEQ ID NO 60
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(16)
<223> OTHER INFORMATION: Any amino acid and this region may encompass
      0-16 residues
<220> FEATURE:
<221> NAME/KEY: MOD_RES
<222> LOCATION: (28)..(35)
<223> OTHER INFORMATION: Any amino acid and this region may encompass
      0-8 residues

<400> SEQUENCE: 60

Xaa Xaa Xaa Xaa Xaa Xaa Xaa Xaa Xaa Xaa Xaa Xaa Xaa Xaa Xaa Xaa
1               5                   10                  15

Phe Phe Arg Lys Ser Lys Glu Lys Ile Gly Lys Xaa Xaa Xaa Xaa Xaa
            20                  25                  30

Xaa Xaa Xaa
        35

<210> SEQ ID NO 61
<211> LENGTH: 34
<212> TYPE: PRT
<213> ORGANISM: Mus sp.

<400> SEQUENCE: 61

Gly Leu Leu Arg Lys Gly Gly Glu Lys Ile Gly Glu Lys Leu Lys Lys
1               5                   10                  15

Ile Gly Gln Lys Ile Lys Asn Phe Phe Gln Lys Leu Val Pro Gln Pro
            20                  25                  30

Glu Gln

```
<210> SEQ ID NO 62
<211> LENGTH: 21
<212> TYPE: PRT
<213> ORGANISM: Mus sp.

<400> SEQUENCE: 62

Met Glu Val Gly Trp Tyr Arg Ser Pro Phe Ser Arg Val Val His Leu
1               5                   10                  15

Tyr Arg Asn Gly Lys
            20

<210> SEQ ID NO 63
<211> LENGTH: 37
<212> TYPE: PRT
<213> ORGANISM: Macaca mulatta

<400> SEQUENCE: 63

Arg Leu Gly Asn Phe Phe Arg Lys Val Lys Glu Lys Ile Gly Gly Gly
1               5                   10                  15

Leu Lys Lys Val Gly Gln Lys Ile Lys Asp Phe Leu Gly Asn Leu Val
            20                  25                  30

Pro Arg Thr Ala Ser
        35

<210> SEQ ID NO 64
<211> LENGTH: 37
<212> TYPE: PRT
<213> ORGANISM: Unknown
<220> FEATURE:
<223> OTHER INFORMATION: Description of Unknown: Rabbit CAP18 sequence

<400> SEQUENCE: 64

Gly Leu Arg Lys Arg Leu Arg Lys Phe Arg Asn Lys Ile Lys Glu Lys
1               5                   10                  15

Leu Lys Lys Ile Gly Gln Lys Ile Gln Gly Leu Leu Pro Lys Leu Ala
            20                  25                  30

Pro Arg Thr Asp Tyr
        35

<210> SEQ ID NO 65
<211> LENGTH: 33
<212> TYPE: PRT
<213> ORGANISM: Mus sp.

<400> SEQUENCE: 65

Gly Leu Leu Arg Lys Gly Gly Glu Lys Ile Gly Glu Lys Leu Lys Lys
1               5                   10                  15

Ile Gly Gln Lys Ile Lys Asn Phe Phe Gln Lys Leu Val Pro Gln Pro
            20                  25                  30

Glu

<210> SEQ ID NO 66
<211> LENGTH: 34
<212> TYPE: PRT
<213> ORGANISM: Rattus sp.

<400> SEQUENCE: 66

Gly Leu Val Arg Lys Gly Gly Glu Lys Phe Gly Glu Lys Leu Arg Lys
1               5                   10                  15

Ile Gly Gln Lys Ile Lys Glu Phe Phe Gln Lys Leu Ala Leu Glu Ile
            20                  25                  30

Glu Gln
```

<210> SEQ ID NO 67
<211> LENGTH: 43
<212> TYPE: PRT
<213> ORGANISM: Unknown
<220> FEATURE:
<223> OTHER INFORMATION: Description of Unknown: Guinea CAP11 sequence

<400> SEQUENCE: 67

Gly Leu Arg Lys Lys Phe Arg Lys Thr Arg Lys Arg Ile Gln Lys Leu
1               5                   10                  15

Gly Arg Lys Ile Gly Lys Thr Gly Arg Lys Val Trp Lys Ala Trp Arg
            20                  25                  30

Glu Tyr Gly Gln Ile Pro Tyr Pro Cys Arg Ile
        35                  40

<210> SEQ ID NO 68
<211> LENGTH: 42
<212> TYPE: PRT
<213> ORGANISM: Canis sp.

<400> SEQUENCE: 68

Lys Lys Ile Asp Arg Leu Lys Glu Leu Ile Thr Thr Gly Gly Gln Lys
1               5                   10                  15

Ile Gly Glu Lys Ile Arg Arg Ile Gly Gln Arg Ile Lys Asp Phe Phe
            20                  25                  30

Lys Asn Leu Gln Pro Arg Glu Glu Lys Ser
        35                  40

<210> SEQ ID NO 69
<211> LENGTH: 43
<212> TYPE: PRT
<213> ORGANISM: Bos sp.
<220> FEATURE:
<221> NAME/KEY: amidation
<222> LOCATION: (43)..(43)

<400> SEQUENCE: 69

Arg Phe Arg Pro Pro Ile Arg Arg Pro Pro Ile Arg Pro Pro Phe Tyr
1               5                   10                  15

Pro Pro Phe Arg Pro Pro Ile Arg Pro Pro Ile Phe Pro Pro Ile Arg
            20                  25                  30

Pro Pro Phe Arg Pro Pro Leu Gly Pro Phe Pro
        35                  40

<210> SEQ ID NO 70
<211> LENGTH: 60
<212> TYPE: PRT
<213> ORGANISM: Bos sp.

<400> SEQUENCE: 70

Arg Arg Ile Arg Pro Arg Pro Pro Arg Leu Pro Arg Pro Arg Pro Arg
1               5                   10                  15

Pro Leu Pro Phe Pro Arg Pro Gly Pro Arg Pro Ile Pro Arg Pro Leu
            20                  25                  30

Pro Phe Pro Arg Pro Gly Pro Arg Pro Ile Pro Arg Pro Leu Pro Phe
        35                  40                  45

Pro Arg Pro Gly Pro Arg Pro Ile Pro Arg Pro Leu
    50                  55                  60

<210> SEQ ID NO 71
<211> LENGTH: 26

```
<212> TYPE: PRT
<213> ORGANISM: Bos sp.
<220> FEATURE:
<221> NAME/KEY: amidation
<222> LOCATION: (26)..(26)
<223> OTHER INFORMATION: C-term amidated

<400> SEQUENCE: 71

Gly Arg Phe Lys Arg Phe Arg Lys Lys Phe Lys Lys Leu Phe Lys Lys
1               5                   10                  15

Leu Ser Pro Val Ile Pro Leu Leu His Leu
            20                  25

<210> SEQ ID NO 72
<211> LENGTH: 27
<212> TYPE: PRT
<213> ORGANISM: Bos sp.
<220> FEATURE:
<221> NAME/KEY: amidation
<222> LOCATION: (27)..(27)

<400> SEQUENCE: 72

Gly Gly Leu Arg Ser Leu Gly Arg Lys Ile Leu Arg Ala Trp Lys Lys
1               5                   10                  15

Tyr Gly Pro Ile Ile Val Pro Ile Ile Arg Ile
            20                  25

<210> SEQ ID NO 73
<211> LENGTH: 33
<212> TYPE: PRT
<213> ORGANISM: Bos sp.
<220> FEATURE:
<221> NAME/KEY: amidation
<222> LOCATION: (33)..(33)

<400> SEQUENCE: 73

Gly Leu Phe Arg Arg Leu Arg Asp Ser Ile Arg Arg Gly Gln Gln Lys
1               5                   10                  15

Ile Leu Glu Lys Ala Arg Arg Ile Gly Glu Arg Ile Lys Asp Ile Phe
            20                  25                  30

Arg

<210> SEQ ID NO 74
<211> LENGTH: 13
<212> TYPE: PRT
<213> ORGANISM: Bos sp.
<220> FEATURE:
<221> NAME/KEY: amidation
<222> LOCATION: (13)..(13)

<400> SEQUENCE: 74

Ile Leu Pro Trp Lys Trp Pro Trp Trp Pro Trp Arg Arg
1               5                   10

<210> SEQ ID NO 75
<211> LENGTH: 12
<212> TYPE: PRT
<213> ORGANISM: Bos sp.

<400> SEQUENCE: 75

Arg Leu Cys Arg Ile Val Val Ile Arg Val Cys Arg
1               5                   10

<210> SEQ ID NO 76
<211> LENGTH: 13
<212> TYPE: PRT
```

-continued

```
<213> ORGANISM: Bubalus sp.
<220> FEATURE:
<221> NAME/KEY: amidation
<222> LOCATION: (13)..(13)

<400> SEQUENCE: 76

Gly Leu Pro Trp Ile Leu Leu Arg Trp Leu Phe Phe Arg
1               5                   10

<210> SEQ ID NO 77
<211> LENGTH: 12
<212> TYPE: PRT
<213> ORGANISM: Ovis sp.

<400> SEQUENCE: 77

Arg Tyr Cys Arg Ile Ile Phe Leu Arg Val Cys Arg
1               5                   10

<210> SEQ ID NO 78
<211> LENGTH: 28
<212> TYPE: PRT
<213> ORGANISM: Ovis sp.
<220> FEATURE:
<221> NAME/KEY: amidation
<222> LOCATION: (28)..(28)

<400> SEQUENCE: 78

Arg Gly Leu Arg Arg Leu Gly Arg Lys Ile Ala His Gly Val Lys Lys
1               5                   10                  15

Tyr Gly Pro Thr Val Leu Arg Ile Ile Arg Ile Ala
            20                  25

<210> SEQ ID NO 79
<211> LENGTH: 33
<212> TYPE: PRT
<213> ORGANISM: Ovis sp.
<220> FEATURE:
<221> NAME/KEY: amidation
<222> LOCATION: (33)..(33)

<400> SEQUENCE: 79

Gly Leu Phe Gly Arg Leu Arg Asp Ser Leu Gln Arg Gly Gly Gln Lys
1               5                   10                  15

Ile Leu Glu Lys Ala Glu Arg Ile Trp Cys Lys Ile Lys Asp Ile Phe
            20                  25                  30

Arg

<210> SEQ ID NO 80
<211> LENGTH: 43
<212> TYPE: PRT
<213> ORGANISM: Ovis sp.
<220> FEATURE:
<221> NAME/KEY: amidation
<222> LOCATION: (43)..(43)

<400> SEQUENCE: 80

Arg Phe Arg Pro Pro Ile Arg Arg Pro Pro Ile Arg Pro Pro Phe Arg
1               5                   10                  15

Pro Pro Phe Arg Pro Pro Val Arg Pro Pro Ile Arg Pro Pro Phe Arg
            20                  25                  30

Pro Pro Phe Arg Pro Pro Ile Gly Pro Phe Pro
            35                  40

<210> SEQ ID NO 81
<211> LENGTH: 52
```

```
<212> TYPE: PRT
<213> ORGANISM: Ovis sp.
<220> FEATURE:
<221> NAME/KEY: amidation
<222> LOCATION: (52)..(52)

<400> SEQUENCE: 81

Arg Arg Leu Arg Pro Arg His Gln His Phe Pro Ser Glu Arg Pro Trp
1               5                   10                  15

Pro Lys Pro Leu Pro Leu Pro Leu Pro Arg Pro Gly Pro Arg Pro Trp
            20                  25                  30

Pro Lys Pro Leu Pro Leu Pro Leu Pro Arg Pro Gly Leu Arg Pro Trp
        35                  40                  45

Pro Lys Pro Leu
    50

<210> SEQ ID NO 82
<211> LENGTH: 60
<212> TYPE: PRT
<213> ORGANISM: Ovis sp.

<400> SEQUENCE: 82

Arg Arg Leu Arg Pro Arg Arg Pro Arg Leu Pro Arg Pro Arg Pro Arg
1               5                   10                  15

Pro Arg Pro Arg Pro Arg Ser Leu Pro Leu Pro Arg Pro Gln Pro Arg
            20                  25                  30

Arg Ile Pro Arg Pro Ile Leu Leu Pro Trp Arg Pro Pro Arg Pro Ile
        35                  40                  45

Pro Arg Pro Gln Ile Gln Pro Ile Pro Arg Trp Leu
    50                  55                  60

<210> SEQ ID NO 83
<211> LENGTH: 94
<212> TYPE: PRT
<213> ORGANISM: Ovis sp.

<400> SEQUENCE: 83

Arg Arg Leu Arg Pro Arg Arg Pro Arg Leu Pro Arg Pro Arg Pro Arg
1               5                   10                  15

Pro Arg Pro Arg Pro Arg Ser Leu Pro Leu Pro Arg Pro Lys Pro Arg
            20                  25                  30

Pro Ile Pro Arg Pro Leu Pro Leu Pro Arg Pro Arg Pro Lys Pro Ile
        35                  40                  45

Pro Arg Pro Leu Pro Leu Pro Arg Pro Arg Pro Arg Ile Pro Arg
    50                  55                  60

Pro Leu Pro Leu Pro Arg Pro Arg Pro Arg Pro Ile Pro Arg Pro Leu
65                  70                  75                  80

Pro Leu Pro Gln Pro Gln Pro Ser Pro Ile Pro Arg Pro Leu
            85                  90

<210> SEQ ID NO 84
<211> LENGTH: 43
<212> TYPE: PRT
<213> ORGANISM: Capra sp.
<220> FEATURE:
<221> NAME/KEY: amidation
<222> LOCATION: (43)..(43)

<400> SEQUENCE: 84

Arg Phe Arg Pro Pro Ile Arg Arg Pro Pro Ile Arg Pro Pro Phe Asn
1               5                   10                  15
```

Pro Pro Phe Arg Pro Pro Val Arg Pro Pro Phe Arg Pro Pro Phe Arg
            20                  25                  30

Pro Pro Phe Arg Pro Pro Ile Gly Pro Phe Pro
            35                  40

<210> SEQ ID NO 85
<211> LENGTH: 26
<212> TYPE: PRT
<213> ORGANISM: Equus sp.

<400> SEQUENCE: 85

Lys Arg Phe Gly Arg Leu Ala Lys Ser Phe Leu Arg Met Arg Ile Leu
1               5                   10                  15

Leu Pro Arg Arg Lys Ile Leu Leu Ala Ser
            20                  25

<210> SEQ ID NO 86
<211> LENGTH: 27
<212> TYPE: PRT
<213> ORGANISM: Equus sp.

<400> SEQUENCE: 86

Lys Arg Arg His Trp Phe Pro Leu Ser Phe Gln Glu Phe Leu Glu Gln
1               5                   10                  15

Leu Arg Arg Phe Arg Asp Gln Leu Pro Phe Pro
            20                  25

<210> SEQ ID NO 87
<211> LENGTH: 40
<212> TYPE: PRT
<213> ORGANISM: Equus sp.

<400> SEQUENCE: 87

Lys Arg Phe His Ser Val Gly Ser Leu Ile Gln Arg His Gln Gln Met
1               5                   10                  15

Ile Arg Asp Lys Ser Glu Ala Thr Arg His Gly Ile Arg Ile Ile Thr
            20                  25                  30

Arg Pro Lys Leu Leu Leu Ala Ser
        35                  40

<210> SEQ ID NO 88
<211> LENGTH: 39
<212> TYPE: PRT
<213> ORGANISM: Sus sp.
<220> FEATURE:
<221> NAME/KEY: amidation
<222> LOCATION: (39)..(39)

<400> SEQUENCE: 88

Arg Arg Arg Pro Arg Pro Pro Tyr Leu Pro Arg Pro Arg Pro Pro Pro
1               5                   10                  15

Phe Phe Pro Pro Arg Leu Pro Pro Arg Ile Pro Pro Gly Phe Pro Pro
            20                  25                  30

Arg Phe Pro Pro Arg Phe Pro
        35

<210> SEQ ID NO 89
<211> LENGTH: 79
<212> TYPE: PRT
<213> ORGANISM: Sus sp.
<220> FEATURE:
<221> NAME/KEY: amidation
<222> LOCATION: (79)..(79)

<400> SEQUENCE: 89

Ala Phe Pro Pro Asn Val Pro Gly Pro Arg Phe Pro Pro Asn
1               5                   10                  15

Phe Pro Gly Pro Arg Phe Pro Pro Asn Phe Pro Gly Pro Arg Phe
            20                  25                  30

Pro Pro Pro Asn Phe Pro Gly Pro Arg Phe Pro Pro Asn Phe Pro
                35                  40                  45

Gly Pro Pro Phe Pro Pro Ile Phe Pro Gly Pro Trp Phe Pro Pro
    50                  55                  60

Pro Pro Pro Phe Arg Pro Pro Pro Phe Gly Pro Pro Arg Phe Pro
65                  70                  75

<210> SEQ ID NO 90
<211> LENGTH: 79
<212> TYPE: PRT
<213> ORGANISM: Sus sp.
<220> FEATURE:
<221> NAME/KEY: amidation
<222> LOCATION: (79)..(79)

<400> SEQUENCE: 90

Ala Phe Pro Pro Asn Val Pro Gly Pro Arg Phe Pro Pro Asn
1               5                   10                  15

Val Pro Gly Pro Arg Phe Pro Pro Asn Phe Pro Gly Pro Arg Phe
            20                  25                  30

Pro Pro Pro Asn Phe Pro Gly Pro Arg Phe Pro Pro Asn Phe Pro
                35                  40                  45

Gly Pro Pro Phe Pro Pro Ile Phe Pro Gly Pro Trp Phe Pro Pro
    50                  55                  60

Pro Pro Pro Phe Arg Pro Pro Pro Phe Gly Pro Pro Arg Phe Pro
65                  70                  75

<210> SEQ ID NO 91
<211> LENGTH: 18
<212> TYPE: PRT
<213> ORGANISM: Sus sp.
<220> FEATURE:
<221> NAME/KEY: amidation
<222> LOCATION: (18)..(18)

<400> SEQUENCE: 91

Arg Gly Gly Arg Leu Cys Tyr Cys Arg Arg Arg Phe Cys Val Cys Val
1               5                   10                  15

Gly Arg

<210> SEQ ID NO 92
<211> LENGTH: 16
<212> TYPE: PRT
<213> ORGANISM: Sus sp.
<220> FEATURE:
<221> NAME/KEY: amidation
<222> LOCATION: (16)..(16)

<400> SEQUENCE: 92

Arg Gly Gly Arg Leu Cys Tyr Cys Arg Arg Arg Phe Cys Ile Cys Val
1               5                   10                  15

<210> SEQ ID NO 93
<211> LENGTH: 18
<212> TYPE: PRT
<213> ORGANISM: Sus sp.
<220> FEATURE:
<221> NAME/KEY: amidation

<222> LOCATION: (18)..(18)

<400> SEQUENCE: 93

Arg Gly Gly Gly Leu Cys Tyr Cys Arg Arg Phe Cys Val Cys Val
1               5                   10                  15

Gly Arg

<210> SEQ ID NO 94
<211> LENGTH: 18
<212> TYPE: PRT
<213> ORGANISM: Sus sp.
<220> FEATURE:
<221> NAME/KEY: amidation
<222> LOCATION: (18)..(18)

<400> SEQUENCE: 94

Arg Gly Gly Arg Leu Cys Tyr Cys Arg Gly Trp Ile Cys Phe Cys Val
1               5                   10                  15

Gly Arg

<210> SEQ ID NO 95
<211> LENGTH: 18
<212> TYPE: PRT
<213> ORGANISM: Sus sp.
<220> FEATURE:
<221> NAME/KEY: amidation
<222> LOCATION: (18)..(18)

<400> SEQUENCE: 95

Arg Gly Gly Arg Leu Cys Tyr Cys Arg Pro Arg Phe Cys Val Cys Val
1               5                   10                  15

Gly Arg

<210> SEQ ID NO 96
<211> LENGTH: 23
<212> TYPE: PRT
<213> ORGANISM: Sus sp.

<400> SEQUENCE: 96

Arg Ile Ile Asp Leu Leu Trp Arg Val Arg Arg Pro Gln Lys Pro Lys
1               5                   10                  15

Phe Val Thr Val Trp Val Arg
            20

<210> SEQ ID NO 97
<211> LENGTH: 35
<212> TYPE: PRT
<213> ORGANISM: Sus sp.
<220> FEATURE:
<221> NAME/KEY: amidation
<222> LOCATION: (35)..(35)

<400> SEQUENCE: 97

Gly Arg Phe Arg Arg Leu Arg Lys Lys Thr Arg Lys Arg Leu Lys Lys
1               5                   10                  15

Ile Gly Lys Val Leu Lys Trp Ile Pro Pro Ile Val Gly Ser Ile Pro
            20                  25                  30

Leu Gly Cys
        35

<210> SEQ ID NO 98
<211> LENGTH: 37
<212> TYPE: PRT
<213> ORGANISM: Sus sp.

```
<400> SEQUENCE: 98

Gly Leu Leu Ser Arg Leu Arg Asp Phe Leu Ser Asp Arg Gly Arg Arg
1               5                   10                  15

Leu Gly Glu Lys Ile Glu Arg Ile Gly Gln Lys Ile Lys Asp Leu Ser
            20                  25                  30

Glu Phe Phe Gln Ser
            35
```

DISEASE TREATMENT VIA ANTIMICROBIAL PEPTIDES OR THEIR INHIBITORS

CROSS-REFERENCE TO RELATED APPLICATIONS

The present application is a divisional of prior application Ser. No. 12/173,344, filed Jul. 15, 2008 now U.S. Pat. No. 8,202,835, which is, in turn, a continuation-in-part of U.S. application Ser. No. 10/539,558 filed Jun. 17, 2005 now abandoned (U.S. Pub. No. 2006/0115480 A1) and also claims priority to each of Israel application serial nos. 184611 filed Jul. 15, 2007 and 187627 filed Nov. 26, 2007, the disclosures of which are incorporated by reference herein in their entireties.

FIELD OF THE INVENTION

The invention relates to the field of mammalian antimicrobial peptides (AMPs) and their use in the treatment of disease.

The Sequence Listing submitted in text format (.txt) on Jul. 18, 2012, named "SEQLIST_ST25.txt", (created on Tuesday, Jul. 17, 2012, 36.2 KB), is incorporated herein by reference.

BACKGROUND OF THE INVENTION

The present invention relates to methods of treating diseases using anti-antimicrobial peptide (AMP) and/or AMP-like molecule (AML) and in particular cathelicidin type AMPs, and to methods of identifying compounds capable of regulating, decreasing or increasing activities/levels of AMPs/AMLs so as to enable treatment of diseases. More particularly, the present invention relates to methods of treating diseases by using cathelicidin or cathelicidin fragments or cathelicidin analogs or compounds capable of regulating the levels/activity of cathelicidin, such diseases including dysregulated cell proliferation/differentiation leading to bone loss or degradation, osteoporosis osteoarthritis, or to other autoimmune diseases such as multiple sclerosis, arthritis, psoriasis, and to malignancies such as carcinomas, which are associated with inflammation, to metabolic diseases, obesity, insulin resistance, diabetes type 2, diabetes type 1 and related diseases. Also, the present invention relates to methods of identifying compounds capable of regulating levels of cathelicidin or other AMPs or to increasing or to decreasing activity/levels of AMPs so as to enable treatment of diseases including autoimmune and inflammatory diseases such as, multiple sclerosis, arthritis, metabolic disorders such as diabetes, obesity and malignant diseases such as carcinomas, which are associated with inflammation, dysregulated cell proliferation/differentiation, angiogenesis and/or metastasis.

Both inhibiting endogenous cathelicidin based peptides or other AMPs as well as the use of such cathelicidin based peptides or analogs of cathelicidin peptides are effective modes of treatments for disease. As was demonstrated in WO 2004-056307 filed by the present inventors and incorporated herein, cathelicidins are immune regulators and are over expressed locally in autoimmune diseases. They are also expressed systemically through bone marrow such that normal plasma concentrations average around 1.2 ug/ml to 1.5 ug/ml (Journal of Immunological Methods 206__1997.53-59). Regulation of their expression is essential for homeostasis. AMPs are involved is skewing dendritic cell activation between Th1 and Th2 inflammatory processes via Toll-like receptors and therefore are involved in homeostasis (J Immunol. 2004 Jan. 15; 172(2):1146-56). Controlling or maintaining such homeostasis is performed by either increasing or decreasing of level/activity between the various AMPs.

Cathelicidins are mainly expressed by Vitamin D3 (calcitriol), via vitamin D3 receptor elements (VDRE) and Vitamin D3 itself has a modulating influence on cathelicidin expression both as an agonist via calcitriol/VDRE and by a negative feedback mechanisms (Marshall T BioEssays 30:173-182, 2008). This VDRE/cathelicidin pathway is unique to humans and furry/haired animals such as rodents for example whose skin is less exposed to sunlight do not possess this pathway. As shown in data included in this invention for the first time relative to prior art, cathelicidin forms a major immune regulator for diseases which are known to be also regulated by vitamin D3. These include amongst others, bone loss in Periodontitis (which is associated with low vitamin D and low cathelicidin), Obesity, Type 2 Diabetes mellitus type 1 and type 2 (which is associated with low vitamin D and Toll like receptor 4, which cathelicidin inhibits), Atherosclerosis (low vitamin D association), Hypertension (low vitamin D association), Asthma and Allergy (low vitamin D association), Osteoporosis and Ostepenia (low vitamin D association), Multiple Sclerosis (low vitamin D association), Rheumatoid arthritis (low vitamin D association), Autoimmune Diseases such as Crohn, Type 1 Diabetes (low vitamin D association), Schizophrenia (low vitamin D association), Muscle wasting disease including age associated muscle wasting (low vitamin D association as well as beta defensin overexpression), Cancer (low vitamin D association as well as Cathelicidin and beta defensin overexpression), Depression (low vitamin D association), Skin inflammation including Psoriasis (treated with vitamin D analogues), Tuberculosis and Influenza (low vitamin D association), Chronic Pain (low vitamin D association), Osteoartheritis (low vitamin D association), The Common Cold and other known diseases (The Breast Journal, Volume 14 Number 3, 2008 255-260, Photochem Photobiol. 2008 March-April; 84(2):356-65) associated with vitamin D3, commonly known as the "Sunshine vitamin" and inappropriately called a vitamin but is in fact a hormone. Data as presented in this invention indicate a common pathway of disease regulation between cathelicidin and vitamin D3. For this reason, the inventor reasons that diseases such as schizophrenia and depression which cannot be modeled suitably by animals are also regulated by cathelicidin.

Diseases, such as malignant, autoimmune, and allergic diseases, which are associated with biological processes such as inflammation, dysregulated cell proliferation/differentiation, and dysregulated cell proliferation/differentiation balance include a vast range of highly debilitating and/or lethal pathologies of great economic impact, for which no satisfactory treatment methods are presently available. For example autoimmune diseases represent diseases of major clinical and economic impact. These include major diseases such as psoriasis, rheumatoid arthritis, type I diabetes, inflammatory bowel diseases, and multiple sclerosis for which no satisfactory treatment methods are available. Similarly, malignant diseases, such as skin carcinoma, breast carcinoma, colon carcinoma, head and neck carcinoma, hepatic carcinoma, lung carcinoma, renal cell carcinoma, urinary bladder carcinoma, and the like, represent numerous lethal diseases for which no satisfactory treatment methods are available.

There is an urgent and long-felt need for optimal methods of treating such diseases which are associated with inflammation, dysregulated cell/tissue proliferation/differentiation and autoimmunity.

The epithelial lining of the skin, gastrointestinal tract and bronchial tree produces a number of peptides with antimicrobial activities termed antimicrobial peptides (AMPs), which appear to be involved in both innate host defense and adaptive immune responses (Yang D. et al., 2001. Cell Mol Life Sci. 58:978-89). AMPs are cationic peptides which display antimicrobial activity at physiological concentrations under conditions prevailing in the tissues of origin. AMP synthesis and release is regulated by microbial signals, developmental and differentiation signals, cytokines and in some cases neuroendocrine signals in a tissue-specific manner. Their mode of action is unknown, however the leading theory claims that permeabilization of target membranes is the crucial step in AMP-mediated antimicrobial activity and cytotoxicity. AMPs are classified into two major groups in humans; cathelicidins and defensins. AMPs appear to have common characteristics that enable them to affect mammalian cells in a way that does not necessarily function through a ligand-receptor pathway, and that, being small, and highly ionic or hydrophobic or structurally amphiphilic, AMPs can bind mammalian cell membranes. They are able to penetrate through the cell membrane to the cytoplasm. For example, it was shown that granulysin penetrates and damages human cell membranes dependent upon negative charge (J. Immunol., 2001, 167:350-356). At high concentrations they are cytotoxic to cells, they tear through the membrane causing lysis or apoptosis. Likewise they are able to change the charge density of the inner membrane by the very fact that they have charge, are small and are distributed around the cell membrane from the outer surface of the membrane.

Cathelicidins contain a conserved "cathelin" precursor domain. Their organization includes an N-terminal signal peptide, a highly conserved prosequence, and a structurally variable cationic peptide at the C-terminus. The prosequence resembles cathelin, a protein originally isolated from porcine neutrophils as an inhibitor of cathepsin L (hence, the name cathelin). The 37 amino acid-long human cathelicidin, LL-37/hCAP18 has a hydrophobic N-terminal domain in an α-helical conformation, particularly in the presence of negatively charged lipids. In a step essential for its activation, LL-37 is enzymatically cleaved from the C-terminus of hCAP 18 precursor via enzymes such as neutrophil elastase and proteinase 3. LL-37 functions in synergy with other AMPs, and can directly activate host cells. Inappropriate cleavage of the cathelicidin hCAP18 pro-peptide by endogenous proteases can produce pro-inflammatory fragments of the cathelicidin (Nat Med. 2007 August; 13(8):975-80). At the same time, correct cleavage via appropriate endogenous protease processing will produce the anti-inflammatory cathelicidin analogs and peptides. Thus, a method for regulating inadequate processing of cathelicidin is required as well as a method of using the anti-inflammatory analogs or fragments to the cathelicidin peptides or pro-peptide is described and exemplified below.

The ability of cathelicidins such as LL-37 to both kill bacteria and regulate immune responses is a characteristic of numerous AMPs. The peptide can influence host immune responses via a variety of cellular interactions, for example, it has been suggest to possibly function as a chemoattractant by binding to formyl-peptide-receptor-like-1 (FPRL-1). LL-37 can recruit mast cells, and then be produced by the mast cell to kill bacteria.

AMPs exert their effects either individually or as the resultant effect of multiple AMPs. For example, in the menstrual cycle there is a monthly cycle-dependent expression of various AMPs (King A. E. et al., 2003. J. Reprod. Immunol. 59:1-16). For example, there is higher expression during the menstrual cycle of beta-defensin-2 in the menstrual stage, beta-defensin-4 in the proliferative stage, beta-defensin-3 in the early secretory stage, beta-defensin-1 in the mid secretory stage, and beta-defensin-3 in the late secretory stage. It has been suggested that maintaining the balance between the AMPs is essential for normal proliferation, differentiation and in the specific example of menstrual cycle for development. In light of the apparent roles of AMPs and most importantly of cathelicidin as was demonstrated in this and the former patent application (number WO 2004-056307) of the current inventor, cathelicidin is associated with inflammation, dysregulated cell proliferation/differentiation, dysregulated cell proliferation/differentiation balance, angiogenesis metastasis, and/or epithelial wounds, the inventor hypothesized that an optimal strategy for treating such diseases would be via methods involving decreasing the levels/activity of such AMPs/AMLs, and/or via methods involving administering such AMPs/AMLs or enhancing their expression.

The prior art approaches relating to such methods involve the previous application of the inventors in WO 2004-056307 which show that cathelicidin is an immune regulator in-vivo and therefore poses a target in treating autoimmune diseases.

The current application provides in-vivo data for specific diseases such as metabolic diseases and low grade inflammatory diseases, obesity, insulin resistance, diabetes type 2, type 1 diabetes, insulin related diabetes, osteoporosis, periodontitis, osteoarthritis, arthritic diseases, rheumatologic diseases such as rheumatoid arthritis, ankylosing spondylitis, gout and systemic lupus erythematosus, as well as multiple sclerosis, neurological and central nervous system diseases as well as osteoporosis.

In particular, the current invention shows in-vivo the use of cathelicidin or cathelicidin analogs in the treatment of said diseases.

SUMMARY OF THE INVENTION

According to one aspect of the present invention there is provided a method of treating a medical condition, such as a disease, in a subject in need of treatment thereof, the method comprising providing to the subject a therapeutically effective amount of a compound in particular a cathelicidin peptide or fragment analog thereof, being capable of treating the disease in the subject in need thereof or of regulating, or increasing or decreasing an activity and/or level of an antimicrobial peptide (AMP) and/or AMP-like molecule, thereby treating the disease in the subject in need thereof.

According to further features in preferred embodiments of the invention described below, administering the compound to the subject is effected by exposing a location of the subject to a carrier which includes the compound at a concentration selected from a range of about 50 nanograms per milliliter to about 2 milligram per milliliter.

According to still further features in the described preferred embodiments, administering the compound to the subject is effected by administering to the subject a plurality of doses of the compound selected from a range of 2 doses to 30 doses, wherein each inter dose interval of the plurality of doses is selected from a range of about 2.4 hours to about 30 days.

According to still further features in the described preferred embodiments, administering the compound to the subject is effected via a route selected from the group consisting of the topical, intravenous, intranasal, transdermal, intradermal, oral, buccal, parenteral, rectal and inhalation route.

According to still further features in the described preferred embodiments, the disease is associated with a biological process in a cell and/or tissue, wherein the biological process is selected from the group consisting of growth, differentiation, autoimmunity or inflammation.

According to still further features in the described preferred embodiments, the subject is human.

According to another aspect of the present invention there is provided an article of manufacture comprising packaging material and a pharmaceutical composition, the article of manufacture being identified for treatment of a disease being associated with a biological process in a cell and/or tissue, the biological process being selected from the group consisting of growth, differentiation or diseases associated with inflammation or autoimmunity; the pharmaceutical composition comprising a pharmaceutically acceptable carrier and, as an active ingredient, a compound being capable of regulating an activity and/or level of an antimicrobial peptide (AMP) and/or AMP-like molecule.

According to further features in preferred embodiments of the invention described below, the pharmaceutically acceptable carrier is selected so as to enable administration of the pharmaceutical composition via a route selected from the group consisting of the topical, intranasal, transdermal, intradermal, intravenous, oral, buccal, parenteral, rectal and inhalation route.

According to still further features in the described preferred embodiments, the pharmaceutical composition is formulated as a solution, suspension, emulsion or gel.

According to still further features in the described preferred embodiments, the pharmaceutical composition is composed so as to enable exposure of a cell and/or tissue of a subject having the disease to the compound at a concentration selected from a range of about 50 nanograms per milliliter to about 1 milligram per milliliter.

According to still further features in the described preferred embodiments, the pharmaceutical composition is further identified for administration to a subject of a plurality of doses of the pharmaceutical composition selected from a range of 2 doses to 30 doses, wherein each inter dose interval of the plurality of doses is selected from a range of about 2.4 hours to about 30 days According to still further features in the described preferred embodiments, the cell and/or tissue is selected from the group consisting of skin cells, bone cells beta cells and synovial tissue.

According to still further features in the described preferred embodiments, the disease is selected from the group consisting of an autoimmune disease, a bone resorption disease, a neurological disease, a metabolic disease including diabetes, obesity, and a diabetes related disease.

According to yet another aspect of the present invention there is provided a method of regulating a biological process in a cell and/or tissue, the method comprising exposing the cell and/or tissue to a compound in particular a cathelicidin peptide or its analog, being capable of regulating the biological process in the cell and/or tissue or of increasing or decreasing an activity and/or level of an antimicrobial peptide (AMP) and/or AMP-like molecule, thereby regulating the biological process in the cell and/or tissue.

According to further features in preferred embodiments of the invention described below, exposing the cell and/or tissue to the compound (such as for example, a cathelicidin peptide or its analog) effected by providing said compound to a subject.

According to still further features in the described preferred embodiments, the providing to the subject the compound is effected by administering the compound to the subject and/or by expressing the compound in the subject.

According to still further features in the described preferred embodiments, the exposing the cell and/or tissue to the compound is effected by exposing the cell and/or tissue to the compound at a concentration selected from a range of about 50 nanograms per milliliter to about one milligram per milliliter.

According to still further features in the described preferred embodiments, the cell and/or tissue is bone or nerve tissue or synovial tissue, wherein the exposing the cell and/or tissue to the compound (such as for example, a cathelicidin peptide or its analog) is effected by exposing the cell and/or tissue to the compound at a concentration selected from a range of about 0.4 microgram per milliliter to about 100 micrograms per milliliter.

According to still another aspect of the present invention there is provided a method of identifying a compound being capable of regulating a biological process in a cell and/or tissue, the method comprising: (a) exposing the cell and/or tissue to a test compound which is: (i) capable of decreasing an activity and/or level of an antimicrobial peptide (AMP) and/or AMP-like molecule, and/or (ii) the AMP and/or AMP-like molecule; and (b) evaluating a capacity of the test compound to regulate the biological process in the cell and/or tissue, thereby identifying the compound being capable of regulating the biological process in the cell and/or tissue.

According to still further features in the described preferred embodiments, the cell and/or tissue is a cultured cell and/or tissue.

According to still further features in the described preferred embodiments, the cell and/or tissue is derived from a human.

According to still further features in the described preferred embodiments, the exposing the cell and/or tissue to the test compound is effected by providing the test compound to a subject.

According to still further features in the described preferred embodiments, the exposing the cell and/or tissue to the test compound is effected by exposing the cell and/or tissue to a cell which produces the test compound.

According to still further features in the described preferred embodiments, the cell which produces the test compound is a B-cell hybridoma.

According to still further features in the described preferred embodiments, the providing the test compound to the subject is effected by administering the test compound to the subject and/or by expressing the test compound in the subject.

According to still further features in the described preferred embodiments, administering the test compound to the subject is effected via a route selected from the group consisting of the topical, intranasal, intravenous, transdermal, intradermal, oral, buccal, parenteral, rectal and inhalation route.

According to still further features in the described preferred embodiments, the test compound is selected from the group consisting of: (a) a molecule capable of binding the AMP and/or AMP-like molecule; (b) an enzyme capable of cleaving the AMP and/or AMP-like molecule; (c) an siRNA molecule capable of inducing degradation of an mRNA encoding the AMP and/or AMP-like molecule; (d) a DNAzyme capable of cleaving an mRNA or DNA encoding the AMP and/or AMP-like molecule; (e) an antisense polynucleotide capable of hybridizing with an mRNA encoding the AMP and/or AMP-like molecule; (f) a ribozyme capable of cleaving an mRNA encoding the AMP and/or AMP-like molecule; (g) a non-functional analog of at least a functional portion of the AMP and/or AMP-like molecule; (h) a molecule capable of inhibiting activation or ligand binding of the AMP and/or AMP-like molecule; and (i) a triplex-forming oligonucleotide capable of hybridizing with a DNA encoding the AMP and/or AMP-like molecule.

According to still further features in the described preferred embodiments, the molecule capable of binding the AMP and/or AMP-like molecule is an antibody or an antibody fragment.

According to still further features in the described preferred embodiments, the antibody fragment is selected from the group consisting of a single-chain Fv, an Fab, an Fab', and an F(ab')2.

According to still further features in the described preferred embodiments, the AMP and/or AMP-like molecule is selected from the group consisting of a defensin, a cathelicidin, a cationic peptide, a hydrophobic peptide, a human AMP and a human AMP-like molecule.

According to still further features in the described preferred embodiments, the AMP is any one of the cathelicidin and/or cathelicidin fragments listed below as SEQ. ID NOS. 1-59.

According to still further features in the described preferred embodiments, the cell and/or tissue is selected from the group consisting of an synovial cell and/or tissue, a nerve cell and/or tissue, a beta cell and/or tissue, an osteoblast, osteocyte or osteoclast cell and/or tissue and an endothelial cell and/or tissue.

According to still further features in the described preferred embodiments, the biological process is selected from the group consisting of growth, differentiation, and associated with an inflammatory disease or autoimmunity.

According to a further aspect of the present invention there is provided a method of treating a disease in a subject, such as a mammal, for example, a human pateitn, in need thereof, the method comprising providing to the subject a therapeutically effective amount of an antimicrobial peptide (AMP) and/or AMP-like molecule (and in particular a cathelicidin, active fragment thereof or active cathelicidin analog of the cathelicidin or the fragment thereof), thereby treating the disease in the subject in need thereof.

According to further features in preferred embodiments of the invention described below, administering the AMP and/or AMP-like molecule to the subject is effected by exposing a location of the subject to a carrier which includes the AMP and/or AMP-like molecule at a concentration selected from a range of about 2 nanograms per milliliter to about 10 micrograms per milliliter.

According to still further features in the described preferred embodiments, administering the AMP and/or AMP-like molecule to the subject is effected via a route selected from the group consisting of the topical, intranasal, transdermal, intradermal, oral, buccal, intravenous, parenteral, rectal and inhalation route.

According to still further features in the described preferred embodiments, the subject is human.

According to yet a further aspect of the present invention there is provided an article of manufacture comprising packaging material and a pharmaceutical composition, the article of manufacture being identified for treatment of a disease being associated with a biological process in a cell and/or tissue, the biological process being selected from the group consisting of growth, differentiation, or inflammation associated with a disease; the pharmaceutical composition comprising a pharmaceutically acceptable carrier and, as an active ingredient, an antimicrobial peptide (AMP) and/or AMP-like molecule.

According to further features in preferred embodiments of the invention described below, the pharmaceutically acceptable carrier is selected so as to enable administration of the pharmaceutical composition via a route selected from the group consisting of the topical, intranasal, transdermal, intravenous, intradermal, oral, buccal, parenteral, rectal and inhalation route. The pharmaceutically acceptable carrier may, for example, be of the sort of carriers known in the art for the delivery of therapeutic peptides. The pharmaceutically acceptable carrier may, for example, be other than water alone or other than water altogether.

According to still further features in the described preferred embodiments, the pharmaceutical composition is formulated as a solution, suspension, emulsion or gel.

According to still further features in the described preferred embodiments, the pharmaceutical composition is composed so as to enable exposure of a cell and/or tissue of a subject having the disease to the compound at a concentration selected from a range of about 2 nanograms per milliliter to about 10 micrograms per milliliter.

According to a further aspect of the present invention there is provided a method of treating an autoimmune disease, chronic inflammatory disease, an inflammatory disease, a cancer, the method comprising of delivering the AMP or analog thereof, in particular a cathelicidin AMP to a human subject or mammal, thereby regulating the biological process in the subject.

According to still a further aspect of the present invention there is provided a method of regulating a biological process in a cell and/or tissue, the method comprising exposing the cell and/or tissue to an antimicrobial peptide (AMP) and/or AMP-like molecule, thereby regulating the biological process in the cell and/or tissue.

According to further features in preferred embodiments of the invention described below, exposing the cell and/or tissue to the AMP and/or AMP-like molecule is effected by providing the AMP and/or AMP-like molecule to a subject.

According to still further features in the described preferred embodiments, the providing to the subject the AMP and/or AMP-like molecule is effected by administering the AMP and/or AMP-like molecule to the subject and/or by expressing the AMP and/or AMP-like molecule in the subject.

According to still further features in the described preferred embodiments, the exposing the cell and/or tissue to the AMP and/or AMP-like molecule is effected by exposing the cell and/or tissue to the AMP and/or AMP-like molecule at a concentration selected from a range of about 2 nanograms per milliliter to about 10 micrograms per milliliter or from about 10 micrograms per milliliter to about 30 micrograms per milliliter.

According to still further features in the described preferred embodiments, the AMP and/or AMP-like molecule is selected from the group consisting of and LL-37 or analogs of LL-37 or other cathelicidins and cathelicidin fragments or analogs as listed below.

According to still further features in the described preferred embodiments, the cell and/or tissue is derived from a human.

The present invention successfully addresses the shortcomings of the presently known configurations by providing: (i) a method of treating a disease which is associated with a biological process in a cell/tissue such as growth, differentiation, inflammation, metastasis and/or angiogenesis by using a compound which is capable of regulating levels/activity of an AMP and/or an AMP-like molecule, of decreasing olevels/activity of an AMP and/or an AMP-like molecule; and/or by using an AMP and/or an AMP-like molecule or by increasing levels/activity of an AMP and/or an AMP-like molecule; (ii) an article of manufacture including such a compound and being labeled for treatment of such a disease; and (iii) a method of identifying such a compound.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Starting on day 11, all mice were examined 3 times per week for incidence and severity of arthritis and each arthritic limb was assigned a numerical score based on the degree of inflammation observed according to the scale below.

Erythema or mild swelling to the tarsals, metatarsal, foot, digits, ankylosis or ankle joint in any one of the four legs marks incidence of arthritis. As can be seen, incidence rate is greater in the control group.

Figure 6:
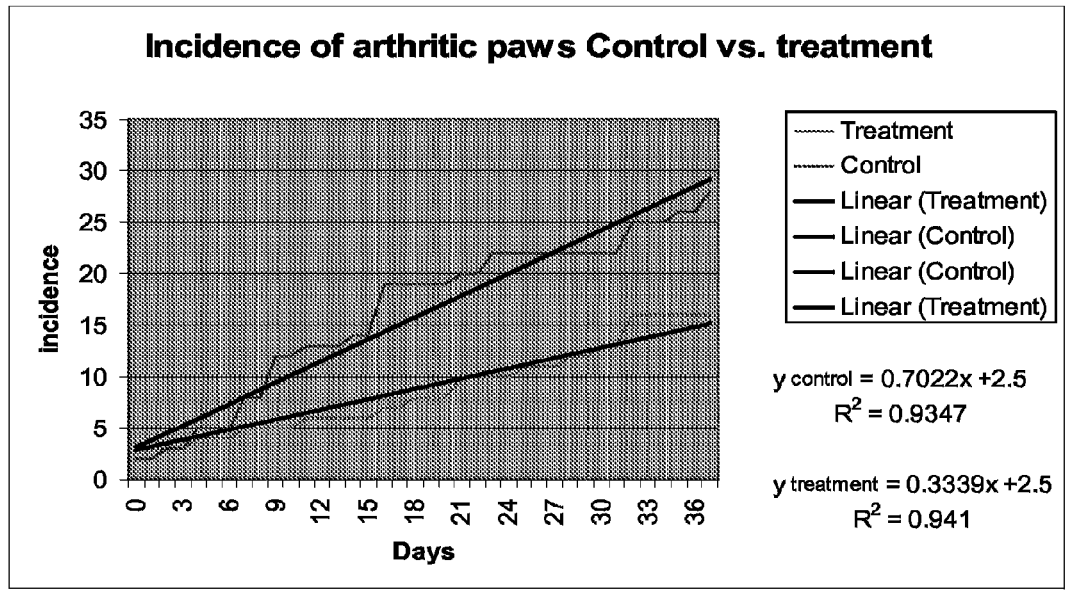

Further analysis of incidence rate of inflamed paws in all mice is shown in FIG. 6.

The sequence of mCRAMP is: gllrkggekigeklkkigqkiknffqklvpqpeq.

Figure 2:
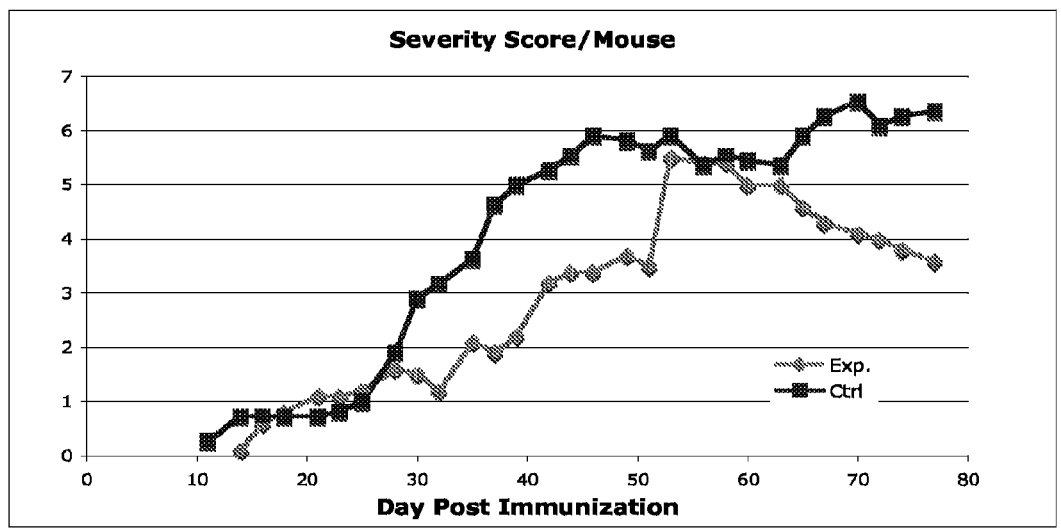

FIG. 2 is a graph depicting Severity of Arthritis—The severity of arthritis was analyzed on the basis of degree of inflammation scored as follows and the number of affected limbs. 0-No evidence of erythema and swelling, 1-Erythema & mild swelling confined to the tarsals or ankle joint, 2-Erythema & mild swelling extending from the ankle to the tarsals, 3-Erythema & moderate swelling extending from the ankle to metatarsal joints, 4-Erythema & severe swelling encompass the ankle, foot, and digits, or ankylosis of the joint.

As seen in the FIG. 2, differences between the two groups were clearly observed when analyzed as mean Severity Score/Mouse. While these data are weighted somewhat by the differences in arthritis incidence, the differences in the severity appear to be even greater than the differences in incidence. Data in FIG. 2 is from the same experiment described in FIG. 1.

Figure 3:
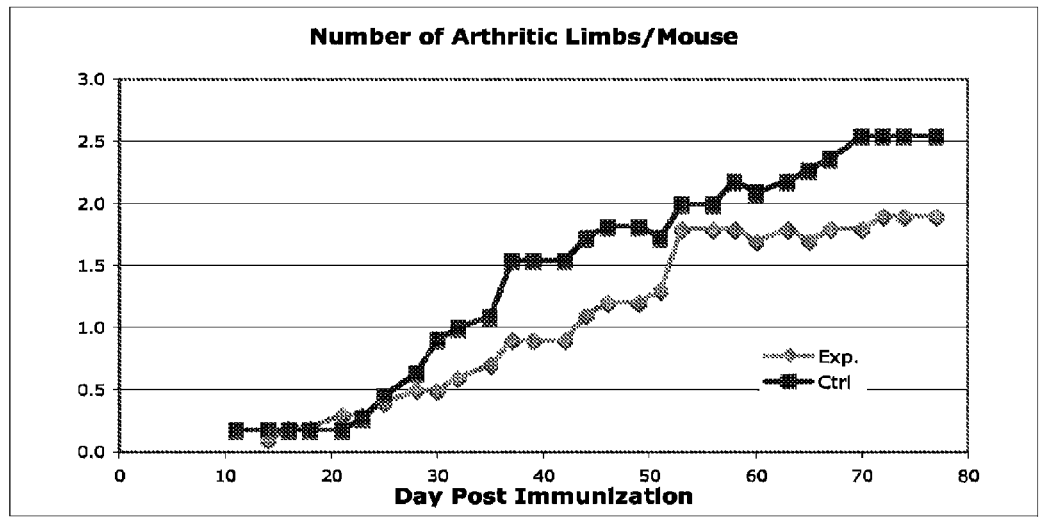

FIG. 3 is a graph depicting the number of Arthritic Limbs/Mouse. Similar to the Severity/Mouse score as in FIG. 2, the number of Arthritic Limbs/Mouse was also generally lower in the experimental group, although the appearance of arthritic limbs followed similar kinetics as the control group, but at a delayed incidence.

Figure 1:
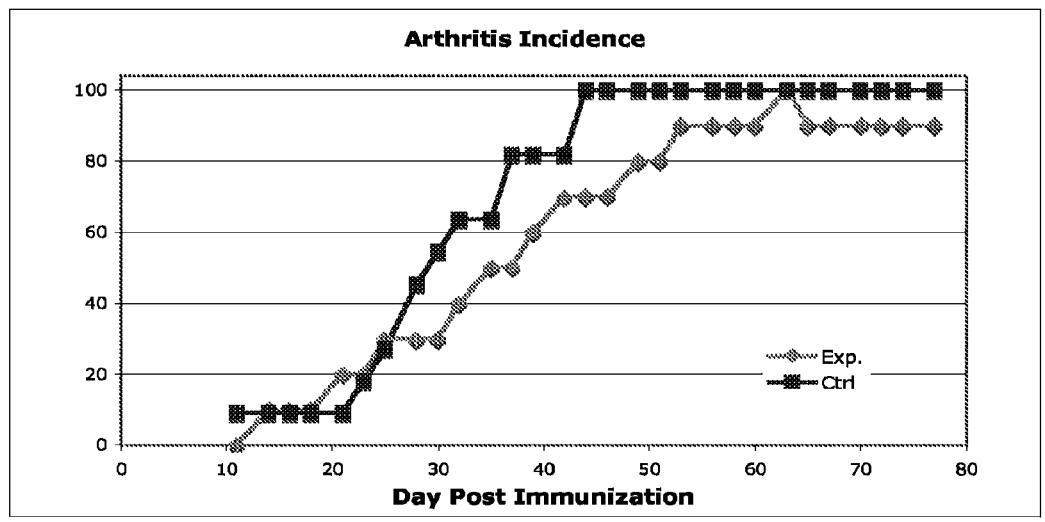
FIG. 1 is a graph depicting incidence of arthritis in mouse model of collagen induced arthritis. Treatment using cathelicidin 34a.a. mCRAMP peptide (experimental group) at a concentration of 1.5 mg/kg. Subsequently on days 2 and 4 post immunization, the dose was reduced to 1.0 mg/kg. Starting with day 7 and through day 72, a dose of 0.8 mg/kg was used. All treatments were performed 3 times per week, on a Monday, Wednesday, and Friday schedule, and the peptide or control vehicle was administered intraperitoneally for each treatment, rotating injection areas. All mice were weighed at the beginning of the experiment in order to calculate dosage administered. At day 49, the mice were again weighed (average of 1.6 gm increase) and dosages were adjusted accordingly.

Data in FIG. 3 is from the same experiment described in FIG. 1 and FIG. 2.

Figure 4:
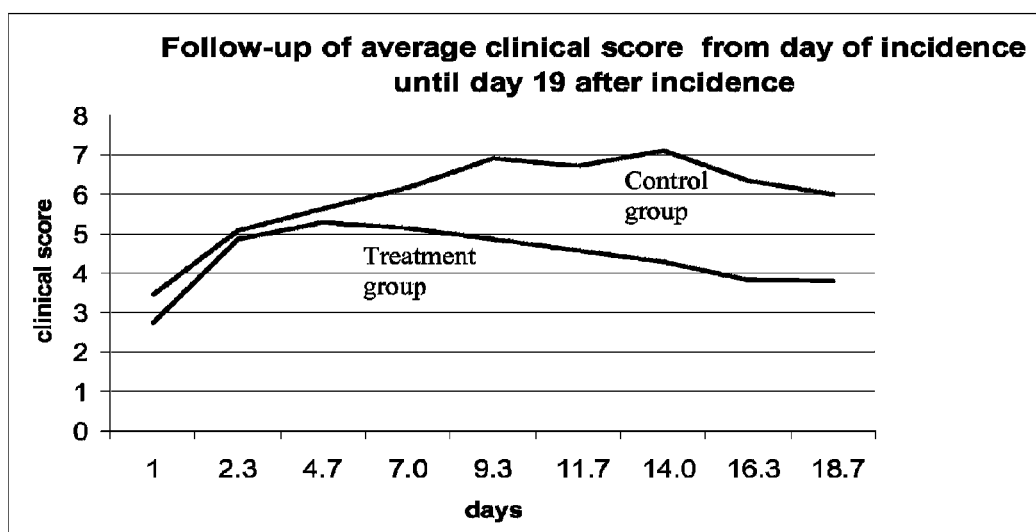

FIG. 4 is a graph showing a follow-up of clinical score from the day of incidence of arthritis until day 19 after incidence. This follow-up is required since each arthritic mouse develops an incidence of inflammation on any one of four paws at a varying number of days since the beginning of the experiment. Therefore in order to determine the significance level between the groups it is necessary to run a follow-up test statistic. Data in FIG. 4 is from the same experiment described in FIG. 1 and FIG. 2.

Figure 5:
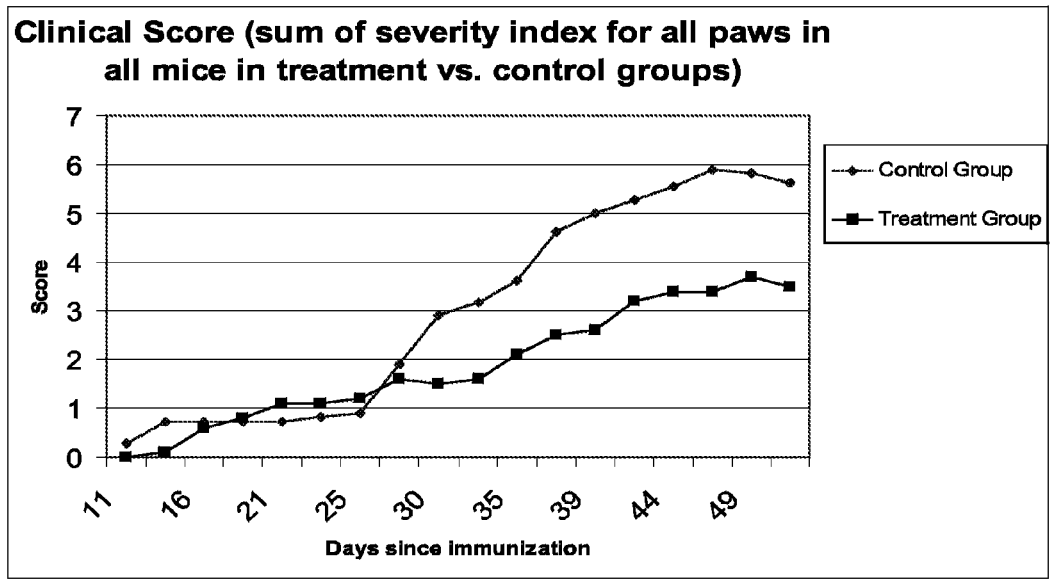

FIG. 5 is a graph showing the sum of the severity index of clinical score in all mice of control versus treatment group during the time in days since immunization.

A clear trend is shown of greater severity of disease in the control group from day 27 onwards. Data in FIG. 5 is from the same experiment described in FIG. 1 and FIG. 2.

FIG. 6 is a graph showing the incidence of arthritic paws in treatment versus control groups. Any one mouse may be included in this data up to four times corresponding to four different paws in any one mouse. A trend line is computed for each of the treatment and control groups using Microsoft excel technology. Data in FIG. 6 is from the same experiment described in FIG. 1 and FIG. 2.

Figures 7, 8:
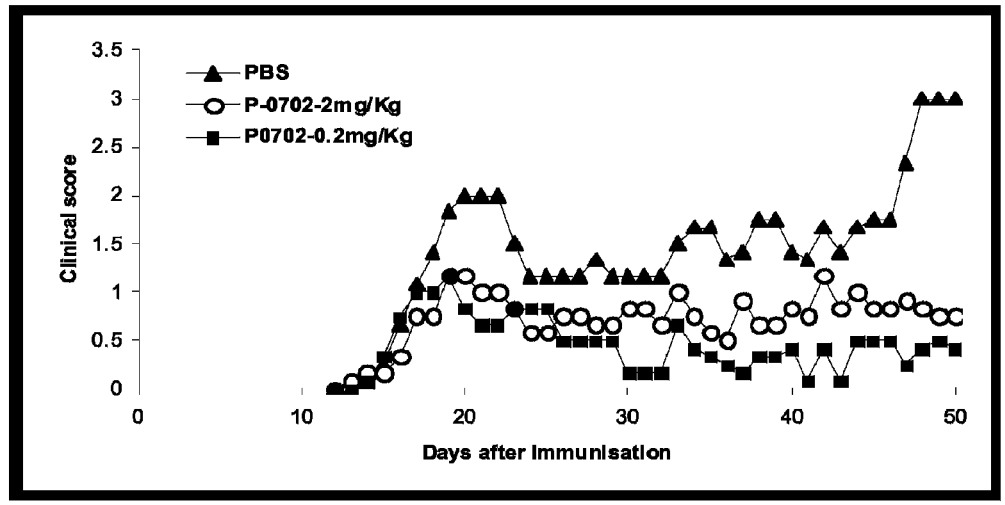

FIG. 7 shows a table listing the results of the mouse Experimental Autoimmune Encephalitis (EAE) model.

C57BL/6 (B6) mice were purchased from Harlan (Jerusalem, Israel). Female, 9 week old mice were used in the experiment. The mice were housed in the specific-pathogen free (SPF) animal facility of the Hebrew University and all experiments were approved by the institutional animal care and use committee (IACUC).

MOGB35-55B peptide (MEVGWYRSPFSRVVH-LYRNGK (SEQ ID NO: 62)) 1.25 mg/ml in PBS was emulsified in complete Freund's adjuvant (CFA) supplemented with 400 mM. tuberculosis (Mt) H37RA (Difco). Mice were immunized s.c. in the flank with 250 µg MOGB35-55B/CFA using a 25G needle. 200 ng Pertussis Toxin (Sigma) was injected i.v. at the time of immunization and 48 h later. EAE was scored on a scale of 0-6: 0, no impairment; 1, limp tail; 2, limp tail and hind limb paresis; 3, ≧1 hind limb paralysis; 4, full hind limb and hind body paralysis; 5, hind body paralysis and front limb paresis; 6, death. Mice were treated with the cathelicidin peptide supplied by Biosight Ltd. Karmiel, Israel diluted in PBS, vs. PBS as a control. Cathelicidin (GLL-RKGGEKIGEKLKKIGQKIKNFFQKLVPQPEQ (SEQ ID NO: 61)) was diluted in sterile PBS and divided to aliquots kept at −20° C. such that each aliquot was thawed once for use. Mice were treated by intraperitoneal (i.p.) injection of roughly 200 µl volume (adjusted for weight) 3 times a week (Sun-Tues-Thurs) starting the day of immunization with MOG/CFA and through day 48. Clinical EAE scores were evaluated through day 60. Dosage of Cathelicidin injections (IP) was 2 mg/Kg and 0.2 mg/Kg. There were six mice in each group (total of 18 mice).

Of particular note is the fact that all the mice who developed EAE eventually died by day 50 while none of the mice in either of the treatment groups died even by day 60.

There is a clear significant difference in average clinical score and in Average score at first peak of disease.

The lower dose of peptide, 0.2 mg/Kg was more protective than the higher 2 mg/Kg dose.

Figure 9A:
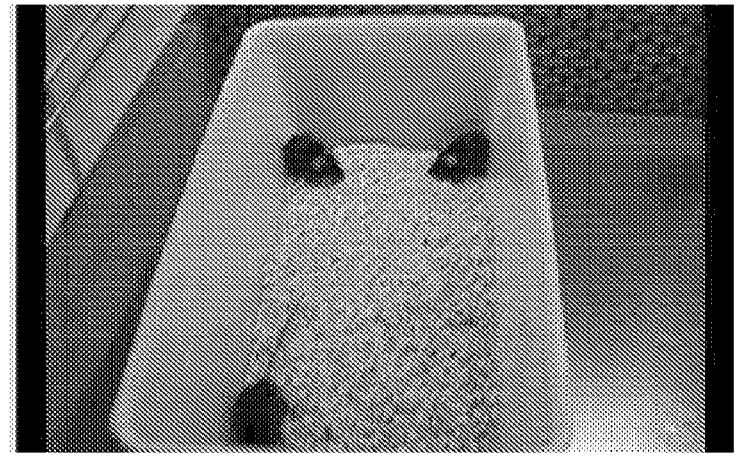
Figure 9B:
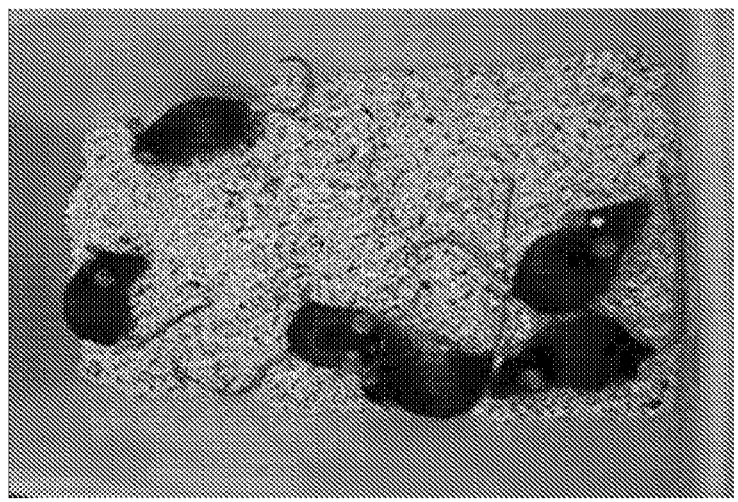

FIG. 8 shows a graph of the average clinical score for each day after immunization for the three groups in the EAE experiment as described in FIG. 7. FIG. 9 shows photographs taken on day 60 of the three remaining healthy mice in the control group, all six remaining live mice in the low dose group, and two examples of EAE affected mice having paralyzed hind legs and tail.

Figure 10:
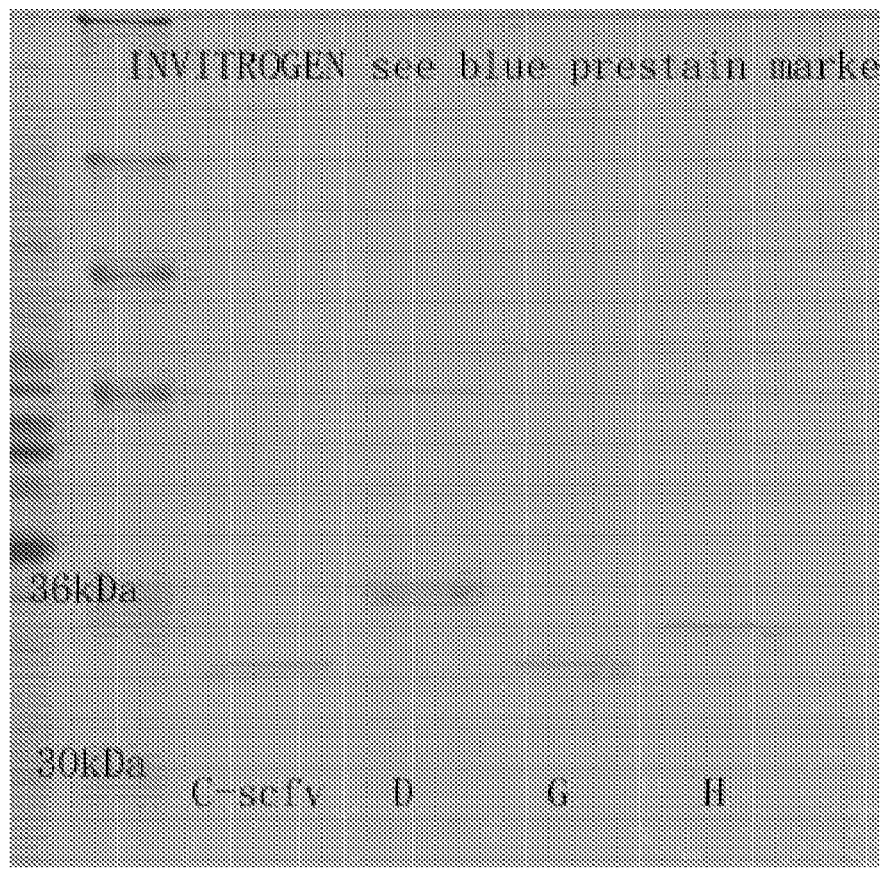

FIG. 10 shows a Western blot analysis of 4 different scFv developed that bind LL-37.

FIG. 11 shows the inhibitory effect of scFv on LL-37 in bacteria killing assays. In order to find out the concentration of LL37 at which 50% of the bacteria could be killed (called "IC50"). Basically the activity protocol follows the ability of the antibody to block the antimicrobial activity of LL-37. The bacteria used were Pseudomonas that was isolated from a wound. The growth medium was LB. LL-37 was added at a concentration of 100 microgram/ml (the final volume or the reaction is 50 microliter). Blocking antibodies at 1 or 5 microliter of antibody (=1:50 or 1:10 dilutions respectively. Low antibody levels ensure a non-specific effect. Concentration of bacteria was estimated by optical density (OD) reading at 490.

Figure 12:
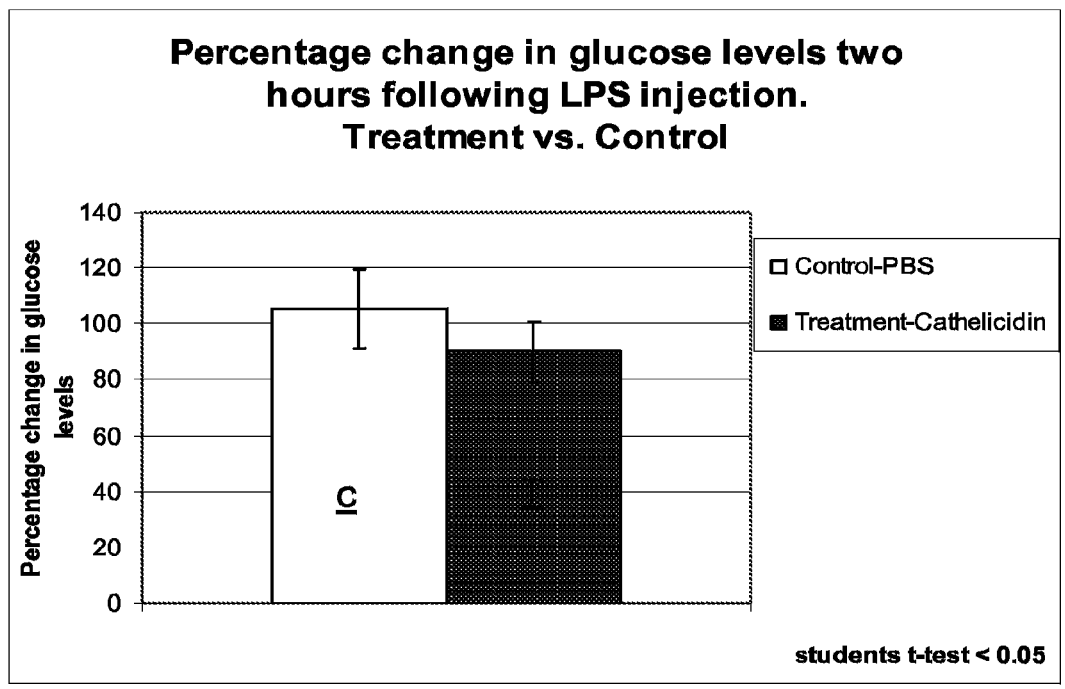

FIG. 12 shows the percentage change in glucose levels two hours following an LPS injection in treatment vs. control. LPS was administered to C57BL/6 mice at 0.2 mg/kg. Mice were bled approximately 2 h after LPS injection (T=0). Changes in glucose levels were examined.

Figure 13:
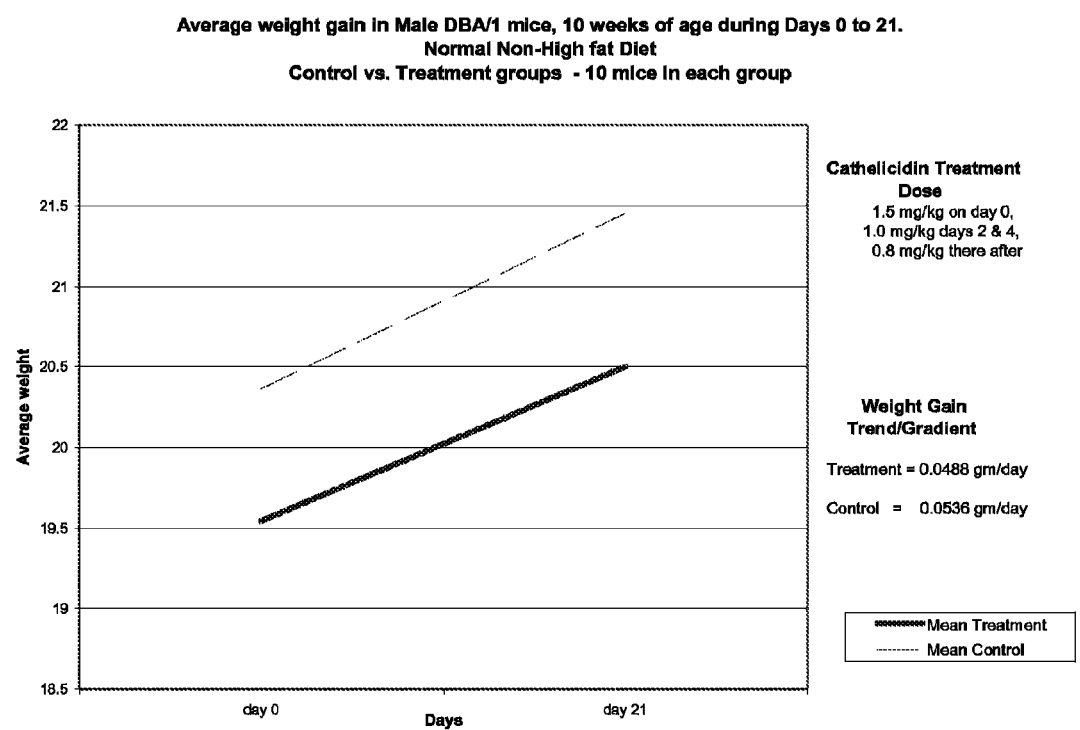

FIG. 13 shows the average weight gain in male DBA/1 mice about ten weeks of age being fed on a normal no-high fat diet for 21 days. Two groups of mice, 10 in each group were weighed. The control increased in weight at an average of 0.0536 gms per day whereas the treatment (cathelicidin mCRAMP at 0.8 ug/ml) increased at 0.0488 per day.

Figure 14:
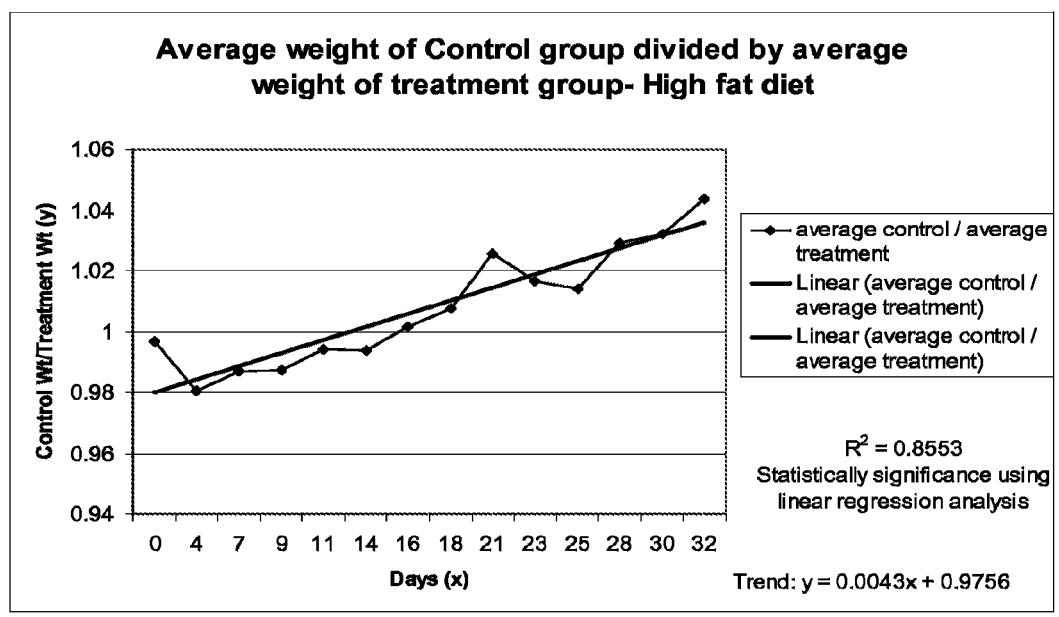

FIG. 14 shows a similar experiment as in FIG. 13 only that the mice were given 0.4 ug/ml and were weighed 3 times a week while being fed a high fat diet of 60% Kcal.

FIG. 15 shows a list of mouse paws selected for analysis for bone resorption, deformation, immunohistology and osteoclast analysis and counting. Mouse paws were obtained from experiment in example 1.

FIG. 16 to FIG. 19 shows the histology analysis showing a beneficial effect of cathelicidin on bone with reduced bone resorption in treatment group even the inflamed treatment group had less osteoclast than the non-inflamed control. Staining was done with H&E and for tartrate-resistant acid phosphatase (TRAP).

Figure 20:
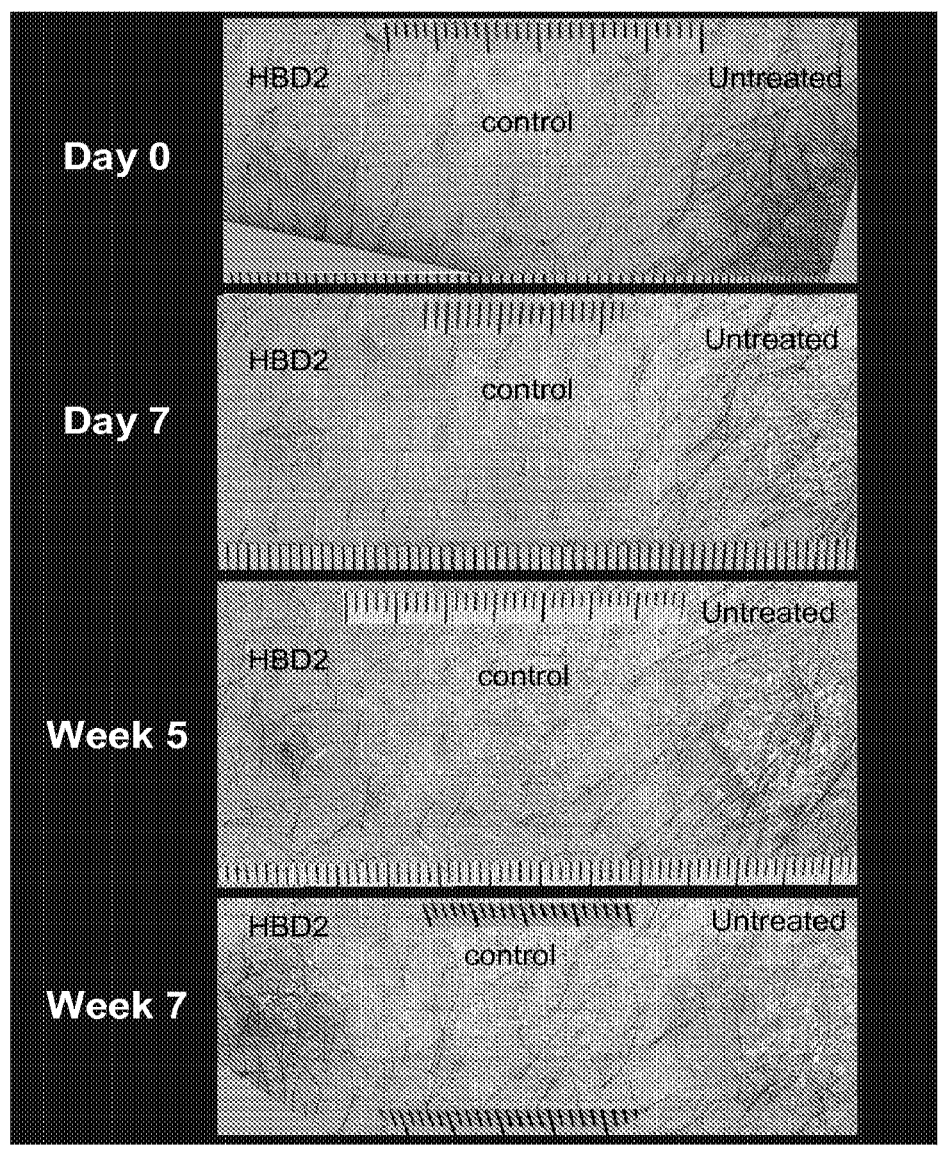
Figure 21:
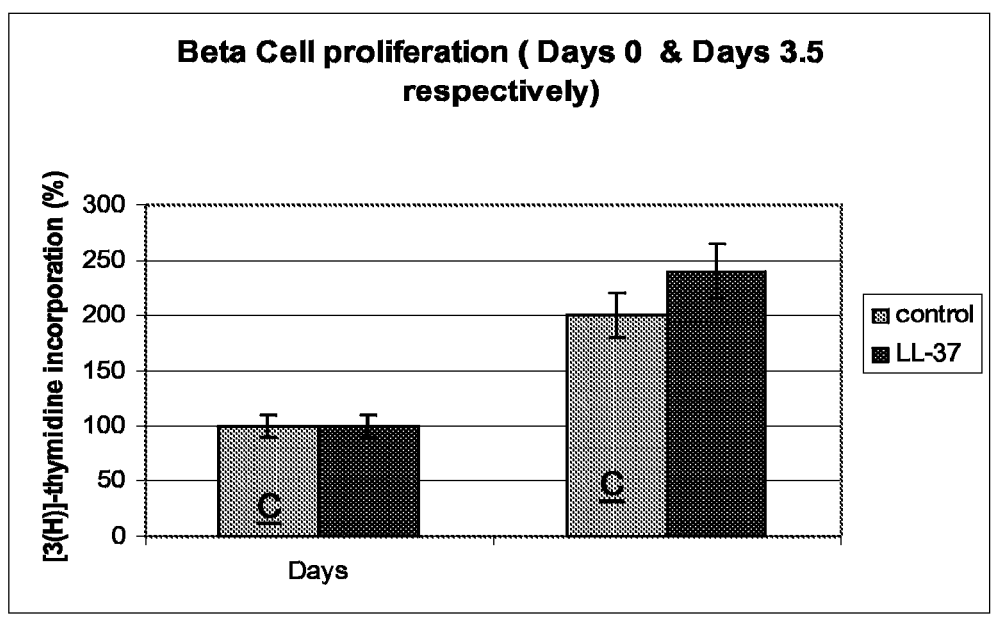

FIG. 20 shows the effect of human beta defensin 2 given for a duration of 7 weeks on human psoriatic skin Inhibition by dominant negative peptide analogues or fragments is suggested as a viable mode of treatment for this disease FIG. 21 shows a histogram depicting significant BETATC beta cell line proliferation brought about by cathelicidin LL-37. Murine beta cell line were treated for 3.5 days with LL-37 at 2 microgram/ml (red/dark bars) and compared to PBS control (red/dark bars). Cell proliferation was estimated by measuring [3(H)]-thymidine incorporation and was expressed as percent of control untreated cells. A representative experiment is shown.

DETAILED DESCRIPTION

The present invention provides methods of using compounds capable of increasing activities/levels of antimicrobial peptides (AMP)/antimicrobial peptide-like molecules (AMLs) and/or of decreasing activities/levels of antimicrobial peptides, (AMP)/antimicrobial peptide-like molecules (AMLs) and/or of using AMPs/AMLs or analogs or fragments thereof for regulating in cells/tissues biological processes such as growth, differentiation, growth/differentiation balance, of methods of using such molecules for treating diseases associated with such biological processes and/or which are amenable to treatment via regulation of such biological processes; for treating autoimmunity, inflammation, metastasis and angiogenesis; of articles of manufacture which include such molecules and which are labeled as being for use in treating such diseases; and of methods of identifying such compounds capable of regulating or increasing or decreasing activities/levels of AMPs/AMLs and/or of identifying such AMPs/AMLs. Specifically, the present invention can be used to optimally treat a vast range of diseases associated with such biological processes, including inflammatory diseases/diseases associated with cellular proliferation/differentiation imbalance, autoimmune and inflammatory diseases such as multiple sclerosis, arthritis, obesity, insulin resistance, osteoporosis, periodontitis, and other diseases associated with autoimmunity and/or cellular proliferation/differentiation imbalance.

Specifically the AMP involved is endogenous cathelicidin or its analogs or fragments thereof.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Diseases which are associated with autoimmunity, inflammation, and dysregulated cell/tissue proliferation/differentiation, dysregulated cell/tissue proliferation/differentiation balance, include a multitude of diseases which are of great medical and/or economic impact and for which no satisfactory treatment methods are available. While conceiving the present invention, the present inventors have hypothesized that AMPs/AMLs are involved in the pathogenesis of such diseases, and/or and hence that methods of regulating or increasing or decreasing activities/levels and/or administering such molecules and in particular, cathelicidins or analogs or fragments of cathelicidin could be used for treating such diseases.

The prior art approach relating to such methods involves the invention of the current inventors in WO 2004-056307 incorporated by reference herein.

The prior art approach, however, relates to autoimmune diseases in general and provides in-vivo data on psoriasis showing that cathelicidin is indeed an immune regulator in psoriasis. The present invention therefore, a continuation in part to the previous invention of the current inventors, shows in-vivo data for various specific diseases associated with autoimmunity, inflammation including low grade inflammation found in metabolic diseases as well as bone cell differentiation/proliferation leading to bone degradation.

While reducing the present invention to practice, it was also uncovered that cathelicidin and therefore AMPs could be used to significantly regulate growth of cultured mouse beta-cells.

Hence, in sharp contrast to prior art techniques, the method according to the present invention enables use of compounds capable of regulating by either increasing or decreasing levels/activity of cathelicidin or of other AMPs/AMLs, and/or the use of such cathelicidins or analogs or fragments thereof or other AMPs/AMLs for regulating biological processes such as growth, differentiation, inflammation, and for the treatment of numerous specific diseases such as for example type 1 diabetes and other diseases such as those which are associated with inflammation, dysregulated cell proliferation/differentiation, chronic inflammatory diseases and autoimmune diseases.

Thus, the present invention provides a method of regulating a biological process in a cell and/or tissue associated with a disease. The method is effected by exposing the cell and/or tissue to: an AMP and in particular a cathelicidin peptide, an analog of a cathelicidin peptide, an analog of a cathelicidin peptide that has been designed to be more stable in-vivo so as not to break down into pro-inflammatory fragments of itself, a cathelicidin analog functioning as a dominant negative or a cathelicidin peptide that competes on binding to cognate receptors with an AMP without inducing disease, a compound being capable of decreasing or increasing an activity and/or level of an antimicrobial peptide (AMP) and/or AMP-like molecule (AML).

The method can be used to regulate in a cell/tissue a biological process such as growth, differentiation, autoimmunity and inflammation. By virtue of enabling regulation of such a biological process in a cell/tissue, the method can be used for treating a disease which is associated with such a biological process, and can be used for identifying the regulator, as described in further detail herein below. Diseases associated with such biological processes include, for example, autoimmune diseases, diseases associated with dysregulated cell/tissue growth/proliferation balance, wound-associated diseases, and tumors.

As used herein, the term "regulator" refers to the compound which is capable of decreasing an activity and/or level of an AMP/AML, increasing an activity and/or level of an AMP/AML, and/or to an AMP which is used for practicing any aspect of the present invention.

As used herein, the phrases "the compound", "compound of the present invention", and "AMP/AML inhibitor" interchangeably refer to the compound which is capable of regulating, decreasing or increasing an activity/level of an AMP/AML.

Any of various types of AMP/AML or AMP/AML inhibitors may be employed according to the teachings of the present invention for regulating the biological process, depending on the application and purpose.

As used herein, the term "AMP" includes any cathelicidin, and/or including any naturally occurring variant of such a molecule, such as a natural mutant/polymorphic variant/allele of such a molecule, or any synthetic variant of such a molecule.

As used herein, the term "AML" includes any molecule having a biological activity which is substantially similar to that of a cathelicidin, includes any molecule which substantially promotes the biological activity of a cathelicidin, and/or includes any molecule which is substantially structurally homologous to a cathelicidin. In such case, homology implied may, for example, vary between 50% to 60%, 60% to 70%, 70% to 80%, 80% to 90%, 90% to 99%, 90%-100%, or at least 95%.

The method may be effected using a single regulator of the present invention, or using any combination of multiple regulators of the present invention.

The AMP/AML inhibitor may be: a molecule capable of binding the AMP/AML; an enzyme capable of cleaving the AMP/AML; an siRNA molecule capable of inducing degradation of an mRNA encoding the AMP/AML; a DNAzyme capable of cleaving an mRNA or DNA encoding the AMP/AML; an antisense polynucleotide capable of hybridizing with an mRNA encoding the AMP/AML; a ribozyme capable of cleaving an mRNA encoding the AMP/AML; a non-functional analog of at least a functional portion of the AMP/AML; a molecule capable of inhibiting activation or ligand binding of the AMP/AML; and a triplex-forming oligonucleotide capable of hybridizing with a DNA encoding the AMP/AML.

Ample guidance for obtaining and utilizing such AMP/AML inhibitors is provided herein below and in the literature of the art (for example, refer to U.S. Patent Application Pub. No. 20030044907 which is incorporated herein by reference).

The AMP/AML inhibitor may be any small molecule, AMP/AML dominant negative, or polypeptide that competes with the AMPs for cognate cell receptors without inducing disease. For example, the AMP/AML inhibitor may be a topological analog of an AMP/AML that has been engineered to remain anti microbial yet lose its chemoattracting ability. Engineering of disulfide bridges to dissect antimicrobial and chemotactic activities of AMPs/AMLs such as human beta-defensin-3 can be performed as previously described (Wu Z. et al., 2003. Proc. Natl. Acad. Sci. U. S. A. 100:8880-5).

The term "dominant negative mutant" as used herein refers to a polypeptide or a nucleic acid coding region sequence which has been changed with regard to at least one position in the sequence, relative to the corresponding wild type native version at a position which changes an amino acid residue position at an active site required for biological and/or pharmacological activity of the native peptide. Accordingly, dominant negative mutants or fragments of the cathelicidin peptide as listed below and contemplated herein include, but are not limited to, polypeptide species which manifest any change (substitution and/or deletion) with regard to at least one amino acid of the AMP or cathelicidin peptide. Dominant negative mutant embodiments of the invention are moreover nucleic acids which encode peptides, as well as the peptides themselves, which comprise fragments of the AMP or more specifically of the cathelicidin hCAP-18 and are listed as in (SEQ. ID NOS: 1-59).

The AMP/AML inhibitor may be a synthetic antibody mimic in which multiple peptide loops are attached to a molecular scaffold (described in U.S. Pat. No. 5,770,380).

Such an AMP/AML mimic can be obtained, for example, by molecule imprinting. This technique may be performed by preparing a polymer by cross-linking a monomer around a "template molecule" (the AMP/AML). This template molecule is removed after the polymerization of the monomer and its size, shape and chemical functions are recorded in the polymer. The sites of the removed template molecule are named "imprint sites". These sites allow the recognition of the template molecule or close structural molecules. Molecularly imprinted polymers can serve as artificial binding mimics as do natural antibodies.

The molecule capable of inhibiting activation or ligand binding of the AMP/AML may advantageously inhibit binding of a receptor expressed on cell, such as a leukocyte, which binds the AMP/AML to inhibit a biological process mediated by binding of the AMP/AML to the receptor. Examples of such AMPs/AMLs and cognate receptors thereof are shown in Table 1.

TABLE 1

AMPs/AMLs and cognate cell receptors, and diseases associated with interaction therebetween

| AMP/AML | Receptor | Receptor-expressing cells | Disease |
|---|---|---|---|
| LL-37 | EGFR, FPRL1 | Monocyte, dendritic cell, T cell, neutrophils, eosinophils, leukocytes, epithelial cell, endothelial cells | Psoriasis, rheumatoid arthritis (RA), atopic dermatitis, contact dermatitis, chronic hepatitis, inflammatory bowel disease (IBD), allergy, B cell malignancies, hepatocellular carcinoma, pancreatic adenocarcinoma and others |
| beta-defensin-2 | Toll 1-like receptor-4 | Dendritic cells | |
| beta-defensin-2 | Toll-like receptor-2 | | |
| beta-defensin-1 beta defensin-2 | CC-chemokine receptor-6 (CCR6) | Hematopoietic cells, dendritic cells, | Psoriasis, RA, atopic dermatitis, contact dermatitis, chronic hepatitis, IBD, allergy, B cell malignancies, hepatocellular carcinoma, pancreatic adenocarcinoma and more |
| defensin-5 | | Intestinal mucosa | Crohn's disease |
| adrenomedullin | L1 and calcitonin receptor-like receptor (CRLR) | gastric epithelial cells | IBD, allergy, hepatocellular carcinoma, and more |

Of particular note is that cathelicidin antimicrobial peptides block dendritic cell TLR4 activation (J Immunol. 2007 Feb. 1; 178(3):1829-34) and therefore cathelicidins would act as inhibitors to beta-defensin activation of TLR4.

Further examples of receptors of AMPs/AMLs such as chemokines, the cells in which such receptors are expressed, and the diseases in which the interaction between such AMPs/AMLs and such receptors are involved are provided in D'Ambrosio et al., 2003. J. Immunol. Methods 273 3-13.

The activity of LL-37 (Weiner, D J. et al., 2003. Am. J. Respir. Cell Mol. Biol. 28:738-745), defensin-3, lactoferrin and IL-8 (Perks, B. et al., 2000. Am. J. Respir. Crit Care Med. 162:1767-1772) is inhibited by F-actin, further inhibitors therefore the AMP/AML inhibitor may be F-actin. F-actin forms bundles in the presence of the polycationic interleukin IL-8, therefore F-actin is an inhibitor of downstream elements of the ligand-receptor connectivity of both LL-37 and interleukin IL-8. LL-37 and defensin-3 are inhibited by gelsolin, therefore the AMP/AML inhibitor may be gelsolin. Serpins and their analogs or fragments are inactivators of AMP by formation of complexes with AMP (Panyutich, A V. et al., 1995. Am. J. Respir. Cell Mol. Biol. 12:351-357; alpha-1 antichymotrypsin, the antimicrobial proteins alpha PI, SLPI and elafin are serpins that form complexes with other AMPs) thereby reducing specific types of inflammation (Hiemstra, P S, 2002. Biochem. Soc. Trans. 30:116-120), therefore the AMP/AML inhibitor may be serpins and their analogs or fragments. The AMP/AML inhibitor may be SIC, a secreted protein of streptococcus pyogenes that inactivates antibacterial peptides.

Other AMP inhibitors or specifically cathelicidin inhibitors include, Alpha 2-Macroglobulin-Proteinase Complexes (Patrik Nyberg et al THE JOURNAL OF BIOLOGICAL CHEMISTRY Vol. 279, No. 51, Issue of December 17, pp. 52820-52823, 2004), aureolysin production by S. aureus and taphylococcus and aureus-Derived Proteinases (Antimicrobial agents and chemotherapy, December 2004, p. 4673-4679), Elastolytic Cathepsins (Journal of Immunology, 2003, 170: 931-937), SufA—a novel subtilisin-like serine proteinase of Finegoldia magna (Microbiology (2007), 153, 4208-4218).

Preferably, the molecule capable of binding the AMP/AML is an antibody or an antibody fragment.

Alternately, the molecule capable of binding the AMP/AML may be any of various type of molecule, including non-immunoglobulin peptides and polypeptides, Preferably, the antibody fragment is selected from the group consisting of a single-chain Fv, an Fab, an Fab', and an F(ab')2.

As used herein, the term "antibody" refers to a substantially intact antibody molecule. The antibody may, for example, be an IgG, IgA or IgM. Antibodies used according to the invention may be monoclonal antibodies or polyclonal antibodies. The antibodies may, for example, be non-human, human or humanized antibodies.

As used herein, the phrase "antibody fragment" refers to a functional fragment of an antibody that is capable of binding to an AMP/AML.

Suitable antibody fragments for practicing the present invention include a complementarity-determining region (CDR) of an immunoglobulin light chain (referred to herein as "light chain"), a CDR of an immunoglobulin heavy chain (referred to herein as "heavy chain"), a variable region of a light chain, a variable region of a heavy chain, a light chain, a heavy chain, an Fd fragment, and antibody fragments comprising essentially whole variable regions of both light and heavy chains such as an Fv, a single chain Fv, an Fab, an Fab', and an F(ab')$_2$.

Functional antibody fragments comprising whole or essentially whole variable regions of both light and heavy chains are defined as follows:

(i) Fv, defined as a genetically engineered fragment consisting of the variable region of the light chain and the variable region of the heavy chain expressed as two chains;

(ii) single chain Fv ("scFv"), a genetically engineered single chain molecule including the variable region of the light chain and the variable region of the heavy chain, linked by a suitable polypeptide linker.

(iii) Fab, a fragment of an antibody molecule containing a monovalent antigen-binding portion of an antibody molecule which can be obtained by treating whole antibody with the enzyme papain to yield the intact light chain and the Fd fragment of the heavy chain which consists of the variable and $C_H 1$ domains thereof;

(iv) Fab', a fragment of an antibody molecule containing a monovalent antigen-binding portion of an antibody molecule which can be obtained by treating whole antibody with the enzyme pepsin, followed by reduction (two Fab' fragments are obtained per antibody molecule); and (v) F(ab')$_2$, a fragment of an antibody molecule containing a monovalent antigen-binding portion of an antibody molecule which can be obtained by treating whole antibody with the enzyme pepsin (i.e., a dimer of Fab' fragments held together by two disulfide bonds).

Methods of generating antibodies (i.e., monoclonal and polyclonal) are well known in the art. Antibodies may be generated via any one of several methods known in the art, which methods can employ induction of in-vivo production of antibody molecules, screening of immunoglobulin libraries (Orlandi D. R. et al., 1989. Proc. Natl. Acad. Sci. U.S.A. 86:3833-3837; Winter G. et al., 1991. Nature 349:293-299) or generation of monoclonal antibody molecules by continuous cell lines in culture. These include, but are not limited to, the hybridoma technique, the human B-cell hybridoma technique, and the Epstein-Barr virus (EBV)-hybridoma technique (Kohler G. et al., 1975. Nature 256:495-497; Kozbor D. et al., 1985. J. Immunol. Methods 81:31-42; Cote R J. et al., 1983. Proc. Natl. Acad. Sci. U.S.A. 80:2026-2030; Cole S P. et al., 1984. Mol. Cell. Biol. 62:109-120).

In cases where target antigens are too small to elicit an adequate immunogenic response when generating antibodies in-vivo, such antigens (haptens) can be coupled to antigenically neutral carriers such as keyhole limpet hemocyanin (KLH) or serum albumin [e.g., bovine serum albumin (BSA)] carriers (see, for example, U.S. Pat. Nos. 5,189,178 and 5,239,078]. Coupling a hapten to a carrier can be effected using methods well known in the art. For example, direct coupling to amino groups can be effected and optionally followed by reduction of the imino linkage formed. Alternatively, the carrier can be coupled using condensing agents such as dicyclohexyl carbodiimide or other carbodiimide dehydrating agents. Linker compounds can also be used to effect the coupling; both homobifunctional and heterobifunctional linkers are available from Pierce Chemical Company, Rockford, Ill. The resulting immunogenic complex can then be injected into suitable mammalian subjects such as mice, rabbits, and the like. Suitable protocols involve repeated injection of the immunogen in the presence of adjuvants according to a schedule which boosts production of antibodies in the serum. The titers of the immune serum can readily be measured using immunoassay procedures which are well known in the art.

The antisera obtained can be used directly or monoclonal antibodies may be obtained as described hereinabove.

Antibody fragments can be obtained using methods well known in the art. [(see, for example, Harlow and Lane, "Antibodies: A Laboratory Manual", Cold Spring Harbor Laboratory, New York, (1988)]. For example, antibody fragments according to the present invention can be prepared by proteolytic hydrolysis of the antibody or by expression in *E. coli* or mammalian cells (e.g., Chinese hamster ovary cell culture or other protein expression systems) of DNA encoding the fragment.

Alternatively, antibody fragments can be obtained by pepsin or papain digestion of whole antibodies by conventional methods. As described hereinabove, an (Fab')$_2$ antibody fragments can be produced by enzymatic cleavage of antibodies with pepsin to provide a 5S fragment. This fragment can be further cleaved using a thiol reducing agent, and optionally a blocking group for the sulfhydryl groups resulting from cleavage of disulfide linkages to produce 3.5S Fab' monovalent fragments. Alternatively, enzymatic cleavage using pepsin produces two monovalent Fab' fragments and an Fc fragment directly. Ample guidance for practicing such methods is provided in the literature of the art (for example, refer to: Goldenberg, U.S. Pat. Nos. 4,036,945 and 4,331,647; Porter, R R., 1959. Biochem. J. 73:119-126). Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

As described hereinabove, an Fv is composed of paired heavy chain variable and light chain variable domains. This association may be noncovalent (see, for example, Inbar et al., 1972. Proc. Natl. Acad. Sci. USA. 69:2659-62). Alternatively, as described hereinabove, the variable domains can be linked to generate a single chain Fv by an intermolecular disulfide bond, or alternately, such chains may be cross-linked by chemicals such as glutaraldehyde.

Preferably, the Fv is a single chain Fv.

Single chain Fv's are prepared by constructing a structural gene comprising DNA sequences encoding the heavy chain variable and light chain variable domains connected by an oligonucleotide encoding a peptide linker. The structural gene is inserted into an expression vector, which is subsequently introduced into a host cell such as *E. coli*. The recombinant host cells synthesize a single polypeptide chain with a linker peptide bridging the two variable domains. Ample guidance for producing single chain Fv's is provided in the literature of the art (for example, refer to: Whitlow and Filpula, 1991. Methods 2:97-105; Bird et al., 1988. Science 242:423-426; Pack et al., 1993. Bio/Technology 11:1271-77; and Ladner et al., U.S. Pat. No. 4,946,778).

Isolated complementarity determining region peptides can be obtained by constructing genes encoding the complementarity determining region of an antibody of interest. Such genes may be prepared, for example, by RT-PCR of mRNA of an antibody-producing cell. Ample guidance for practicing such methods is provided in the literature of the art (for example, refer to Larrick and Fry, 1991. Methods 2:106-10).

It will be appreciated that for human therapy or diagnostics, humanized antibodies are preferably used. Humanized forms of non human (e.g., murine) antibodies are genetically engineered chimeric antibodies or antibody fragments having—preferably minimal—portions derived from non human antibodies. Humanized antibodies include antibodies in which complementary determining regions of a human antibody (recipient antibody) are replaced by residues from a complementarity determining region of a non human species (donor antibody) such as mouse, rat or rabbit having the desired functionality. In some instances, Fv framework residues of the human antibody are replaced by corresponding non human residues. Humanized antibodies may also comprise residues which are found neither in the recipient antibody nor in the imported complementarity determining region or framework sequences. In general, the humanized antibody will comprise substantially all of at least one, and typically two, variable domains, in which all or substantially all of the complementarity determining regions correspond to those of a non human antibody and all, or substantially all, of the framework regions correspond to those of a relevant human consensus sequence. Humanized antibodies optimally also include at least a portion of an antibody constant region, such as an Fc region, typically derived from a human antibody (see, for example, Jones et al., 1986. Nature 321:522-525; Riechmann et al., 1988. Nature 332:323-329; and Presta, 1992. Curr. Op. Struct. Biol. 2:593-596).

Methods for humanizing non human antibodies are well known in the art. Generally, a humanized antibody has one or more amino acid residues introduced into it from a source which is non human. These non human amino acid residues are often referred to as imported residues which are typically taken from an imported variable domain. Humanization can be essentially performed as described (see, for example: Jones et al., 1986. Nature 321:522-525; Riechmann et al., 1988. Nature 332:323-327; Verhoeyen et al., 1988. Science 239:1534-1536; U.S. Pat. No. 4,816,567) by substituting human complementarity determining regions with corresponding rodent complementarity determining regions. Accordingly, such humanized antibodies are chimeric antibodies, wherein substantially less than an intact human variable domain has been substituted by the corresponding sequence from a non human species. In practice, humanized antibodies may be typically human antibodies in which some complementarity determining region residues and possibly some framework residues are substituted by residues from analogous sites in rodent antibodies.

Thus, for example, antibodies used in the treatments of the invention may be humanized antibodies against LL-37 or against an epitope of hCAP-18.

Human antibodies can also be produced using various techniques known in the art, including phage display libraries [see, for example, Hoogenboom and Winter, 1991. J. Mol. Biol. 227:381; Marks et al., 1991. J. Mol. Biol. 222:581; Cole et al., "Monoclonal Antibodies and Cancer Therapy", Alan R. Liss, pp. 77 (1985); Boerner et al., 1991. J. Immunol. 147:86-95). Humanized antibodies can also be made by introducing sequences encoding human immunoglobulin loci into transgenic animals, e.g., into mice in which the endogenous immunoglobulin genes have been partially or completely inactivated. Upon antigenic challenge, human antibody production is observed in such animals which closely resembles that seen in humans in all respects, including gene rearrangement, chain assembly, and antibody repertoire. Ample guidance for practicing such an approach is provided in the literature of the art (for example, refer to: U.S. Pat. Nos. 5,545,807, 5,545,806, 5,569,825, 5,625,126, 5,633,425, and 5,661,016; Marks et al., 1992. Bio/Technology 10:779-783; Lonberg et al., 1994. Nature 368:856-859; Morrison, 1994. Nature 368:812-13; Fishwild et al., 1996. Nature Biotechnology 14:845-51; Neuberger, 1996. Nature Biotechnology 14:826; Lonberg and Huszar, 1995. Intern. Rev. Immunol. 13:65-93; Kellermann, S A. et al., 2002. Curr. Op. Biotechnol. 13:593-597).

Once antibodies are obtained, they may be tested for activity, for example via ELISA.

Suitable antibodies may in many cases be purchased ready for use from commercial suppliers, such as Pharmingen, Dako, Becton-Dickinson, Sigma-Aldrich, and the like. Algae can be used to industrially mass-produce antibodies (Proc Natl Acad Sci USA. 2003, 100:438-42).

As described hereinabove, the AMP/AML inhibitor may be a small interfering RNA (siRNA) molecule. RNA interference is a two step process. the first step, which is termed as the initiation step, input dsRNA is digested into 21-23 nucleotide (nt) small interfering RNAs (siRNA), probably by the action of Dicer, a member of the RNase III family of dsRNA-specific ribonucleases, which processes (cleaves) dsRNA (introduced directly or via a transgene or a virus) in an ATP-dependent manner. Successive cleavage events degrade the RNA to 19-21 bp duplexes (siRNA), each with 2-nucleotide 3' overhangs [Hutvagner and Zamore Curr. Opin. Genetics and Development 12:225-232 (2002); and Bernstein Nature 409: 363-366 (2001)].

In the effector step, the siRNA duplexes bind to a nuclease complex to from the RNA-induced silencing complex (RISC). An ATP-dependent unwinding of the siRNA duplex is required for activation of the RISC. The active RISC then targets the homologous transcript by base pairing interactions and cleaves the mRNA into 12 nucleotide fragments from the 3' terminus of the siRNA [Hutvagner and Zamore Curr. Opin. Genetics and Development 12:225-232 (2002); Hammond et al. (2001) Nat. Rev. Gen. 2:110-119 (2001); and Sharp Genes. Dev. 15:485-90 (2001)]. Although the mechanism of cleavage is still to be elucidated, research indicates that each RISC contains a single siRNA and an RNase [Hutvagner and Zamore Curr. Opin. Genetics and Development 12:225-232 (2002)].

Because of the remarkable potency of RNAi, an amplification step within the RNAi pathway has been suggested. Amplification could occur by copying of the input dsRNAs which would generate more siRNAs, or by replication of the siRNAs formed. Alternatively or additionally, amplification could be effected by multiple turnover events of the RISC [Hammond et al. Nat. Rev. Gen. 2:110-119 (2001), Sharp Genes. Dev. 15:485-90 (2001); Hutvagner and Zamore Curr. Opin. Genetics and Development 12:225-232 (2002)]. For more information on RNAi see the following reviews Tuschl ChemBiochem. 2:239-245 (2001); Cullen Nat. Immunol. 3:597-599 (2002); and Brantl Biochem. Biophys. Act. 1575: 15-25 (2002).

Synthesis of RNAi molecules suitable for use with the present invention can be effected as follows. First, the AMP/AML mRNA sequence is scanned downstream of the AUG start codon for AA dinucleotide sequences. Occurrence of each AA and the 3' adjacent 19 nucleotides is recorded as potential siRNA target sites. Preferably, siRNA target sites are selected from the open reading frame, as untranslated regions (UTRs) are richer in regulatory protein binding sites. UTR-binding proteins and/or translation initiation complexes may interfere with binding of the siRNA endonuclease complex [Tuschl ChemBiochem. 2:239-245]. It will be appreciated though, that siRNAs directed at untranslated regions may also be effective, as demonstrated for GAPDH wherein siRNA directed at the 5' UTR mediated about 90% decrease in cellular GAPDH mRNA and completely abolished protein level (www.ambion.com/techlib/tn/91/912.html).

As used herein the term "about" refers to plus or minus 10%. Wherever the term "about" occurs, it should be understood that the invention also provides corresponding embodiments wherein the degree of variation is plus or minus 5%.

Second, potential target sites are compared to an appropriate genomic database (e.g., human, mouse, rat etc.) using any sequence alignment software, such as the BLAST software available from the NCBI server (www.ncbi.nlm.nih.gov/BLAST/). Putative target sites which exhibit significant homology to other coding sequences are filtered out.

Qualifying target sequences are selected as template for siRNA synthesis. Preferred sequences are those including low G/C content as these have proven to be more effective in mediating gene silencing as compared to those with G/C content higher than 55%%. Several target sites are preferably selected along the length of the target gene for evaluation. For better evaluation of the selected siRNAs, a negative control is preferably used in conjunction. Negative control siRNA preferably include the same nucleotide composition as the siRNAs but lack significant homology to the genome. Thus, a scrambled nucleotide sequence of the siRNA is preferably used, provided it does not display any significant homology to any other gene.

As described hereinabove, the AMP/AML inhibitor may be a DNAzyme molecule capable of specifically cleaving an mRNA transcript or DNA sequence of the AMP/AML. DNAzymes are single-stranded polynucleotides which are capable of cleaving both single and double stranded target sequences (Breaker, R. R. and Joyce, G. Chemistry and Biology 1995; 2:655; Santoro, S. W. & Joyce, G. F. Proc. Natl, Acad. Sci. USA 1997; 943:4262). A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine: pyrimidine junctions (Santoro, S. W. & Joyce, G. F. Proc. Natl, Acad. Sci. USA 199; for rev of DNAzymes see Khachigian, L M [Curr Opin Mol Ther 4:119-21 (2002)].

Examples of construction and amplification of synthetic, engineered DNAzymes recognizing single and double-stranded target cleavage sites have been disclosed in U.S. Pat. No. 6,326,174 to Joyce et al.

As described hereinabove, the AMP/AML inhibitor may be an antisense polynucleotide capable of specifically hybridizing with an mRNA transcript encoding the AMP/AML.

Design of antisense molecules which can be used to efficiently decrease levels/activity of an AMP/AML must be effected while considering two aspects important to the antisense approach. The first aspect is delivery of the oligonucleotide into the cytoplasm of the appropriate cells, while the second aspect is design of an oligonucleotide which specifically binds the designated mRNA within cells in a way which inhibits translation thereof.

The prior art teaches of a number of delivery strategies which can be used to efficiently deliver oligonucleotides into a wide variety of cell types [see, for example, Luft J Mol Med 76: 75-6 (1998); Kronenwett et al. Blood 91: 852-62 (1998); Rajur et al. Bioconjug Chem 8: 935-40 (1997); Lavigne et al. Biochem Biophys Res Commun 237: 566-71 (1997) and Aoki et al. (1997) Biochem Biophys Res Commun 231: 540-5 (1997)].

In addition, algorithms for identifying those sequences with the highest predicted binding affinity for their target mRNA based on a thermodynamic cycle that accounts for the energetics of structural alterations in both the target mRNA and the oligonucleotide are also available [see, for example, Walton et al. Biotechnol Bioeng 65: 1-9 (1999)].

Such algorithms have been successfully used to implement an antisense approach in cells. For example, the algorithm developed by Walton et al. enabled scientists to successfully design antisense oligonucleotides for rabbit beta-globin (RBG) and mouse tumor necrosis factor-alpha (TNF alpha) transcripts. The same research group has more recently reported that the antisense activity of rationally selected oligonucleotides against three model target mRNAs (human lactate dehydrogenase A and B and rat gp130) in cell culture as evaluated by a kinetic PCR technique proved effective in almost all cases, including tests against three different targets in two cell types with phosphodiester and phosphorothioate oligonucleotide chemistries.

In addition, several approaches for designing and predicting efficiency of specific oligonucleotides using an in vitro system were also published (Matveeva et al., Nature Biotechnology 16: 1374-1375 (1998)].

Several clinical trials have demonstrated safety, feasibility and activity of antisense oligonucleotides. For example, antisense oligonucleotides suitable for the treatment of cancer have been successfully used [Holmund et al., Curr Opin Mol Ther 1:372-85 (1999)], while treatment of hematological malignancies via antisense oligonucleotides targeting c-myb gene, p53 and Bc1-2 had entered clinical trials and had been shown to be tolerated by patients [Gerwitz Curr Opin Mol Ther 1:297-306 (1999)].

More recently, antisense-mediated suppression of human heparanase gene expression has been reported to inhibit pleural dissemination of human cancer cells in a mouse model [Uno et al., Cancer Res 61:7855-60 (2001)].

Thus, the current consensus is that recent developments in the field of antisense technology which, as described above, have led to the generation of highly accurate antisense design algorithms and a wide variety of oligonucleotide delivery systems, enable an ordinarily skilled artisan to design and implement antisense approaches suitable for downregulating expression of known sequences without having to resort to undue trial and error experimentation.

As described hereinabove, the AMP/AML inhibitor may be a ribozyme molecule capable of specifically cleaving an mRNA transcript encoding the AMP/AML. Ribozymes are being increasingly used for the sequence-specific inhibition of gene expression by the cleavage of mRNAs encoding proteins of interest [Welch et al., Curr Opin Biotechnol. 9:486-96 (1998)]. The possibility of designing ribozymes to cleave any specific target RNA has rendered them valuable tools in both basic research and therapeutic applications. In the therapeutics area, ribozymes have been exploited to target viral RNAs in infectious diseases, dominant oncogenes in cancers and specific somatic mutations in genetic disorders [Welch et al., Clin Diagn Virol. 10:163-71 (1998)]. Most notably, several ribozyme gene therapy protocols for HIV patients are already in Phase 1 trials. More recently, ribozymes have been used for transgenic animal research, gene target validation and pathway elucidation. Several ribozymes are in various stages of clinical trials. ANGIOZYME was the first chemically synthesized ribozyme to be studied in human clinical trials. ANGIOZYME specifically inhibits formation of the VEGF-r (Vascular Endothelial Growth Factor receptor), a key component in the angiogenesis pathway. Ribozyme Pharmaceuticals, Inc., as well as other firms have demonstrated the importance of anti-angiogenesis therapeutics in animal models. HEPTAZYME, a ribozyme designed to selectively destroy Hepatitis C Virus (HCV) RNA, was found effective in decreasing Hepatitis C viral RNA in cell culture assays (Ribozyme Pharmaceuticals, Incorporated—WEB home page).

As described hereinabove, the AMP/AML inhibitor may be a triplex forming oligonucleotides (TFOs). TFOs can be used for regulating the expression of an AMP/AML gene in cells. Recent studies have shown that TFOs can be designed which can recognize and bind to polypurine/polypyrimidine regions in double-stranded helical DNA in a sequence-specific manner. These recognition rules are outlined by Maher III, L. J., et al., Science, 1989; 245:725-730; Moser, H. E., et al., Science, 1987; 238:645-630; Beal, P. A., et al, Science, 1992; 251:1360-1363; Cooney, M., et al., Science, 1988;

241:456-459; and Hogan, M. E., et al., EP Publication 375408. Modification of the oligonucleotides, such as the introduction of intercalators and backbone substitutions, and optimization of binding conditions (pH and cation concentration) have aided in overcoming inherent obstacles to TFO activity such as charge repulsion and instability, and it was recently shown that synthetic oligonucleotides can be targeted to specific sequences (for a recent review see Seidman and Glazer, J Clin Invest 2003; 112:487-94).

In general, the triplex-forming oligonucleotide has the sequence correspondence: oligo, 3'—A G G T; duplex, 5'—A G C T; and duplex, 3'—T C G A.

However, it has been shown that the A-AT and G-GC triplets have the greatest triple helical stability (Reither and Jeltsch, BMC Biochem, 2002, Sep. 12, Epub). The same authors have demonstrated that TFOs designed according to the A-AT and G-GC rule do not form non-specific triplexes, indicating that the triplex formation is indeed sequence specific.

Thus for any given sequence in the AMP/AML gene a triplex forming sequence may be devised. Triplex-forming oligonucleotides preferably are at least 15, more preferably 25, still more preferably 30 or more nucleotides in length, up to 50 or 100 bp.

Transfection of cells (for example, via cationic liposomes) with TFOs, and formation of the triple helical structure with the target DNA induces steric and functional changes, blocking transcription initiation and elongation, allowing the introduction of desired sequence changes in the endogenous DNA and resulting in the specific downregulation of gene expression. Examples of such suppression of gene expression in cells treated with TFOs include knockout of episomal supFG1 and endogenous HPRT genes in mammalian cells (Vasquez et al., Nucl Acids Res. 1999; 27:1176-81, and Puri, et al, J Biol Chem, 2001; 276:28991-98), and the sequence— and target specific downregulation of expression of the Ets2 transcription factor, important in prostate cancer etiology (Carbone, et al, Nucl Acid Res. 2003; 31:833-43), and the pro-inflammatory ICAM-1 gene (Besch et al, J Biol Chem, 2002; 277:32473-79). In addition, Vuyisich and Beal have recently shown that sequence specific TFOs can bind to dsRNA, inhibiting activity of dsRNA-dependent enzymes such as RNA-dependent kinases (Vuyisich and Beal, Nuc. Acids Res 2000; 28:2369-74).

Additionally, TFOs designed according to the abovementioned principles can induce directed mutagenesis capable of effecting DNA repair, thus providing both downregulation and upregulation of expression of endogenous genes (Seidman and Glazer, J Clin Invest 2003; 112:487-94). Detailed description of the design, synthesis and administration of effective TFOs can be found in U.S. Patent Application Nos. 2003 017068 and 2003 0096980 to Froehler et al, and 2002 0128218 and 2002 0123476 to Emanuele et al, and U.S. Pat. No. 5,721,138 to Lawn.

Techniques for administering such molecules to a cell or cellular structure are routinely practiced by the ordinarily skilled artisan, and ample guidance is provided in the literature of the art for such administration (refer, for example, to the references relevant to such molecules cited hereinabove and to U.S. Patent Application No. 2003/0044907 which is incorporated herein by reference).

As described hereinabove, the method of regulating the biological process of the present invention comprises the step of exposing the cell/tissue to the regulator.

Exposing the cell/tissue to the regulator may be effected in various ways depending on the application and purpose. In cases where the cell/tissue form part of a human or an animal subject, exposing the cell/tissue to the regulator is preferably effected by providing the regulator to the subject.

Administering the regulator to a subject may be effected via any suitable route facilitating exposure of the cell/tissue with the regulator, including a route selected from the group consisting of the topical, intravenous, intranasal, transdermal, intradermal, oral, buccal, parenteral, rectal and inhalation route.

Preferably, subcutaneous and/or local injection of the regulator in saline solution is used for treating a disease such as arthritis.

Preferably, oral delivery in combination with aspirin or with NSAID of the regulator (such as for example cathelicidin or its analog or fragments or analogs of its fragments) in tablet form is used for treating a disease such as arthritis or other inflammatory diseases regularly treated by NSAID or aspirins such as for example atherosclerosis, osteoarthritis, or rheumatic diseases.

Preferably, topical application of the regulator in lipid or saline solution, or in a cream on the skin is used for treating a cutaneous disease such as a psoriasis legion.

Preferably, for treating respiratory diseases such as cystic fibrosis and asthma or COPD, the regulator is dissolved in a solution or provided in an inhalable powder form and administered using an inhaler.

Alternately, the cells may be exposed to regulator by expressing the regulator in the human or animal. In cases where the cell/tissue is a cultured cell/tissue, exposing the regulator to the cell/tissue is preferably effected by providing the regulator to the cell/tissue in-vitro using standard tissue culture methods. Preferably, providing the regulator to the cell/tissue in-vitro is effected as described in the Examples section which follows.

The regulator can be expressed in a subject by directly administering to the subject a nucleic acid construct configured so as to suitably express the regulator in-vivo. Alternatively, a nucleic acid construct for expressing the regulator may be introduced into a suitable cell ex-vivo via an appropriate gene delivery vehicle/method (transfection, transduction, homologous recombination, etc.), and using a suitable genetic expression system as needed. The modified cells may be expanded in culture and administered to the subject where they will produce the regulator in-vivo. To enable cellular expression of the regulator, a nucleic acid construct which encodes the regulator preferably includes at least one cis acting regulatory element, most preferably a promoter which is active in the specific cell population transformed. The nucleic acid construct can further include an enhancer, which can be adjacent or distant to the promoter sequence and can function in up regulating the transcription there from.

Suitable in vivo nucleic acid transfer techniques include transfection with viral or non-viral constructs, such as adenovirus, lentivirus, Herpes simplex I virus, or adeno-associated virus (AAV) and lipid-based systems, polylysine based systems and dendrimers. Useful lipids for lipid-mediated transfer of the gene are, for example, DOTMA, DOPE, and DC-Chol [Tonkinson et al., Cancer Investigation, 14(1): 54-65 (1996)]. The most preferred constructs for use in gene therapy are viruses, most preferably adenoviruses, AAV, lentiviruses, or retroviruses. A viral construct such as a retroviral construct includes at least one transcriptional promoter/enhancer or locus-defining element(s), or other elements that control gene expression by other means such as alternate splicing, nuclear RNA export, or post-translational modification of messenger. Such vector constructs also include a packaging signal, long terminal repeats (LTRs) or portions thereof, and positive and negative strand primer binding sites appropriate to the virus used, unless it is already present in the viral construct. The construct may include a signal that directs polyadenylation, as well as one or more restriction sites and a translation termination sequence. By way of example, such a constructs will typically include a 5' LTR, a tRNA binding site, a packaging signal, an origin of second-strand DNA synthesis, and a 3' LTR or a portion thereof.

The various aspects of the present invention may be practiced by using, increasing or by decreasing the activity/level, of any of various types of AMPs/AMLs, depending on the application and purpose. For example in the experimental data use of cathelicidin peptide or its analog or its fragment is shown for treating disease.

Preferably, the AMP/AML is a cationic and/or hydrophobic peptide.

As used herein, the term "peptide" (with the exception of the term in the context of the phrases "antimicrobial peptide" or "antimicrobial-like peptide", refers to a polypeptide which is composed of less than 51 amino acid residue.

Alternatively, a cathelidin may be more that 51 a.a. such as for example hCAP-18 which contains and includes the pro-region of the LL-37 peptide.

Preferably, the AMP/AML is a cathelicidin.

Preferably, the cathelicidin is LL-37.

Preferably, the AMP/AML is of human origin. Alternately, it may be of non-human origin, in which case it is preferably of mammalian origin.

Numerous examples of AMPs/AMLs which may be used, and/or whose activity/levels may be decreased, for practicing the various aspects of the present invention are described in further detail herein below.

The method may be practiced so as to regulate the biological process in any of various cells/tissues of the present invention.

The cell/tissue is preferably from bone, synovial fluid or beta cells.

The method may be used to regulate the biological process in any of various types of cells/tissues involved in disease included in the present invention.

The method may be affected by exposing the cell/tissue to the regulator at any of various concentrations, depending on the application and purpose.

Preferably, when using an AMP/AML inhibitor of the present invention for regulating the biological process, exposing the cell/tissue to the AMP/AML inhibitor is effected by exposing the cell/tissue to the AMP/AML inhibitor at a concentration selected from a range of about 50 nanograms per milliliter to about one milligram per milliliter.

Exposing the cell/tissue to the AMP/AML inhibitor may advantageously be effected, depending on the application and purpose, by exposing the cell/tissue to the AMP/AML inhibitor at a concentration selected from a range of about 50 ng/ml to about 100 micrograms/ml, from a range of about 100 micrograms/ml to about 200 micrograms/ml, from a range of about 200 micrograms/ml to about 300 micrograms/ml, from a range of about 300 micrograms/ml to about 400 micrograms/ml, from a range of about 400 micrograms/ml to about 500 micrograms/ml, from a range of about 500 micrograms/ml to about 600 micrograms/ml, from a range of about 600 micrograms/ml to about 700 micrograms/ml, from a range of about 700 micrograms/ml to about 800 micrograms/ml, from a range of about 800 micrograms/ml to about 900 micrograms/ml, and from a range of about 900 micrograms/ml to about 1 mg/ml.

Preferably, when using an AMP/AML of the present invention for regulating the biological process, exposing the cell/tissue to the AMP/AML is effected by exposing the cell/tissue to the AMP/AML at a concentration selected from a range of about 2 ng/ml to about 50 micrograms/ml or from 50 micrograms/ml to 100 micrograms/ml. Exposing the cell/tissue to the AMP/AML and in particular to cathelicidin may advantageously be effected, depending on inhibitor at a concentration selected from a range of about 2 ng/ml to about 1 micrograms/ml, from a range of about 1 micrograms/ml to about 2 micrograms/ml, from a range of about 2 micrograms/ml to about 3 micrograms/ml, from a range of about 3 micrograms/ml to about 4 micrograms/ml, from a range of about 4 micrograms/ml to about 5 micrograms/ml, from a range of about 5 micrograms/ml to about 6 micrograms/ml, from a range of about 6 micrograms/ml to about 7 micrograms/ml, from a range of about 7 micrograms/ml to about 8 micrograms/ml, from a range of about 8 micrograms/ml to about 9 micrograms/ml, from a range of about 9 micrograms/ml to about 10 mg/ml, from a range of about 10 micrograms/ml to about 11 micrograms/ml, from a range of about 11 micrograms/ml to about 12 mg/ml, from a range of about 12 micrograms/ml to about 13 micrograms/ml, from a range of about 13 micrograms/ml to about 17 mg/ml, from a range of about 17 micrograms/ml to about 20 micrograms/ml, from a range of about 20 micrograms/ml to about 25 mg/ml.

The method can be used to regulate in the cell/tissue a biological process such as growth, differentiation, inflammation or autoimmunity.

For regulating growth in an epithelial, skin and/or gastrointestinal cell/tissue, the regulator may advantageously be an AMP/AML inhibitor of the present invention and/or an AMP/AML (in particular, a cathelicidin or a cathelicidin analog) of the present invention.

As used herein, the phrase "cathelicidin inhibitor" refers to a compound of the present invention which is capable of decreasing an activity and/or level of a cathelicidin.

As described hereinabove, the present invention can be used for regulating biological processes such as growth, differentiation, inflammation, chronic inflammation and autoimmunity. It will be appreciated that such biological processes are associated with the pathogenesis of numerous diseases, and that regulation of such biological processes according to the teachings of the present invention can be used for treating such diseases.

As used herein, the term "disease" refers to any medical disease, disorder, condition, or syndrome, or to any undesired and/or abnormal physiological morphological, cosmetic and/or physical state and/or condition.

Herein, the term "treating" includes abrogating, substantially inhibiting, slowing or reversing the progression of a disease, substantially ameliorating clinical symptoms of a disease or substantially preventing the appearance of clinical symptoms of a disease.

The method can be used for treating any of various diseases.

In particular, the method can be used for treating any of various diseases which are associated with: (i) inflammation; (ii) dysregulation of growth/differentiation of a cell/tissue; (iv) dysregulation of growth/differentiation balance in bone (v) dysregulation of growth/differentiation balance in beta cell function and insulin production (iii) dysregulation of growth/differentiation balance of a cell/tissue; and (iv) autoimmunity.

Examples of such diseases, and others, which are amenable to treatment via the present invention are listed hereinbelow.

One of ordinary skill in the art, such as a physician, most preferably a physician specialized in the disease, will possess the necessary expertise for treating a disease according to the teachings of the present invention.

As used herein, the phrase "subject in need thereof" refers to a subject having the disease.

Preferably, the subject is a mammal, most preferably a human.

By virtue of demonstrably enabling regulation of growth of a pancreatic beta cell cell/tissue, the method described above for inducing or inhibiting such growth is particularly suitable for treating any of various diseases associated with dysregulated/diminished growth of insulin producing cells, and hence can be used for treating any of various diseases associated with insulin depletion. Such diseases notably include diabetes mellitus type 1 or insulin dependant diabetes or type 2 diabetes, and other metabolic diseases including low grade inflammatory diseases. In addition, the method of cell growth regulation as required in the treatment of cancer is also demonstrated.

By virtue of demonstrably enabling inhibition of Experimental Autoimmune Encephalitis (EAE) inflammation in an in-vivo mouse model, the method described above for inhibiting such inflammation is particularly suitable for treating any of various diseases associated with such inflammation. Such diseases notably include inflammatory or autoimmune diseases, such as neurodegenerative disease, central nervous system diseases, multiple sclerosis, Alzheimer's disease, Parkinson's disease, myasthenia gravis, motor neuropathy, Guillain-Barre syndrome, autoimmune neuropathy, Lambert-Eaton myasthenic syndrome, paraneoplastic neurological disease, paraneoplastic cerebellar atrophy, non-paraneoplastic stiff man syndrome, progressive cerebellar atrophy, Rasmussen's encephalitis, amyotrophic lateral sclerosis, Sydeham chorea, Gilles de la Tourette syndrome, autoimmune polyendocrinopathy, dysimmune neuropathy, acquired neuromyotonia, arthrogryposis multiplex, optic neuritis, spongiform encephalopathy, migraine, headache, cluster headache, and stiff-man syndromeautoimmune diseases.

By virtue of demonstrably enabling inhibition of Collagen induced arthritis (CIA) inflammation in an in-vivo mouse model for rheumatic diseases including rheumatoid arthritis, the method described above for inhibiting such inflammation is particularly suitable for treating any of various diseases associated with such inflammation or autoimmunity and particularly in rheumatic diseases. Such diseases notably include inflammatory or autoimmune diseases, such as arthritis, rheumatic diseases and connective tissue/inflammatory diseases include arthritis, rheumatoid arthritis, pyogenic arthritis, mixed connective tissue disease, cholesteatoma, lupus, relapsing polychondritis, autoimmune myositis, primary Sjogren's syndrome, smooth muscle autoimmune disease, myositis, tendinitis, a ligament inflammation, chondritis, a joint inflammation, a synovial inflammation, carpal tunnel syndrome, osteoarthritis, ankylosing spondylitis, a skeletal inflammation, an autoimmune ear disease, osteoporosis, fibromyalgia, periodontitis, and an autoimmune disease of the inner ear, Diseases diagnosed or managed by the rheumatologist include, Rheumatic diseases such as systemic Lupus Erythematosus, scleroderma (systemic sclerosis), dermatomyositis, polymyositis, polymyalgia rheumatica, osteoarthritis, septic arthritis, sarcoidosis, gout, pseudogout spondyloarthropathies, ankylosing spondylitis, reactive arthritis, psoriatic arthropathy, enteropathic spondylitis, reactive arthropathy vasculitis, polyarteritis nodosa, Henoch-Schönlein purpura, serum sickness, Wegener's granulomatosis, giant cell arteritis, temporal arteritis, Takayasu's arteritis, Behcet's syndrome, Kawasaki's disease (mucocutaneous lymph node syndrome), Buerger's disease (thromboangiitis obliterans), Juvenile Idiopathic Arthritis(JIA).

By virtue of demonstrably enabling inhibition of weight gain and nutritional and Metabolic Diseases and low grade inflammation in an in-vivo mouse model that uses a high fat diet and LPS injections (IP) in order to induce disease, the method described above for inhibiting such inflammation is particularly suitable for treating any of various diseases associated with such inflammation. Such diseases notably include inflammatory or autoimmune diseases, such as obesity, diabetes, insulin resistance, type 2 diabetes, Phenylketonuria (PKU), Metabolic syndrome, Sodium metabolism disorders, Calcium metabolism disorders, Hypercalcemia, Hypocalcemia, Potassium metabolism disorders, Hyperkalemia, Hypokalemia, Phosphate metabolism disorders, Magnesium metabolism disorders, Acid-Base metabolism disorders, atherosclerosis, cardio vascular diseases including; Aneurysm, Angina, Arrhythmia, Atherosclerosis, Cardiomyopathy, Cerebrovascular Accident (Stroke), Cerebrovascular disease, Congenital heart disease, Congestive Heart Failure, Myocarditis, Valve Disease, Coronary Artery Disease, Dilated cardiomyopathy, Diastolic dysfunction, Endocarditis, High Blood Pressure (Hypertension), Hypertrophic cardiomyopathy, Mitral valve prolapse, Myocardial infarction (Heart Attack), Venous Thromboembolism.

By virtue of demonstrably enabling prevention of insulin resistance and Metabolic Diseases and low grade inflammation in an in-vivo mouse model that uses LPS injections (IP) in order to induce disease, the method described above for inhibiting such inflammation is particularly suitable for treating any of various diseases associated with such inflammation. Such diseases notably include inflammatory or autoimmune diseases, such as Fatigue, Intestinal bloating, Sleepiness, Weight gain, Increased blood triglyceride levels, Increased blood pressure, depression, Hyperglycemia, hyperglycaemia, or high blood sugar, diabetes mellitus, type 1 diabetes, type 2 diabetes, Polycystic ovarian syndrome (PCOS), Hypertension, Dyslipidemia that includes high triglyceride levels, glandular/inflammatory diseases that include type B insulin resistance, Schmidt's syndrome, Cushing's syndrome, thyrotoxicosis, benign prostatic hyperplasia, pancreatic disease, Hashimoto's thyroiditis, idiopathic adrenal atrophy, Graves' disease, androgenic alopecia, thyroid disease, thyroiditis, spontaneous autoimmune thyroiditis, idiopathic myxedema, ovarian autoimmunity, autoimmune antisperm infertility, autoimmune prostatitis, Addison's disease, and Type I autoimmune polyglandular syndrome.

By virtue of demonstrably enabling prevention of synovial pathology and bone resorption and degradation or deformation and low grade inflammation in an in-vivo mouse model, the method described above for inhibiting such inflammation is particularly suitable for treating any of various diseases associated with such inflammation. Such diseases notably include inflammatory or autoimmune diseases, such as osteoporosis, Osteogenesis imperfecta, Paget's disease, Osteochondroma, Osteomalacia, Osteomyelitis, Osteopetroses, Renal Osteodystrophy, Unicameral Bone Spurs, Bone Tumor, Craniosynostosis, Enchondroma, Fibrous Dysplasia, Giant Cell Tumor of Bone, Infectious Arthritis, Osteomyelitis, Klippel-Feil Syndrome, Limb Length Discrepancy, Osteochondritis Dissecans, periodontitis, bone loss in periodontitis, connective tissue/inflammatory diseases which include arthritis, rheumatoid arthritis, pyogenic arthritis, mixed connective tissue disease, cholesteatoma, relapsing polychondritis, autoimmune myositis, primary Sjogren's syndrome, smooth muscle autoimmune disease, myositis, tendinitis, a ligament inflammation, chondritis, a joint inflammation, a synovial inflammation, carpal tunnel syndrome, osteoarthritis, ankylosing spondylitis, a skeletal inflammation, an autoimmune ear disease, osteoporosis, fibromyalgia, periodontitis, and an autoimmune disease of the inner ear.

By virtue of demonstrably enabling improvement of psoriasis and/or skin inflammation in an in-vivo model, the method described above for inhibiting such inflammation is particularly suitable for treating any of various diseases associated with such inflammation or for wound healing. Such diseases notably include inflammatory or autoimmune diseases, such as cutaneous/inflammatory diseases include psoriasis, rosacea, dandruff, pemphigus vulgaris, lichen planus, atopic dermatitis, excema, scleroderma, dermatomyositis, alopecia, blepharitis, skin carcinoma, melanoma, squamous cell carcinoma, acne vulgaris, erythema toxicum neonatorum, folliculitis, skin wrinkles, autoimmune bullous skin disease, bullous pemphigoid, pemphigus foliaceus, dermatitis, and drug eruption.

For treating the disease, the regulator such as for example an AMP/AML or the cathelicidin peptide or cathelicidin peptide analog or a cathelicidin protein or a cathelicidin dominant negative analog or a cathelicidin fragment or inhibitor may be administered via any of various suitable regimens.

Depending on the application and purpose, each inter dose interval of the plurality of doses may advantageously be selected from a range of about 2.4 hours to about 3 days, from a range of about 3 days to about 6 days, from a range of about 6 days to about 9 days, from a range of about 9 days to about 12 days, from a range of about 12 days to about 15 days, from a range of about 15 days to about 18 days, from a range of about 18 days to about 21 days, from a range of about 21 days to about 24 days, from a range of about 24 days to about 27 days, or from a range of about 27 days to about 30 days.

Preferably, the inter dose interval of the plurality of doses is about 1 day. This bearing in mind that the half-life of LL-37 peptide in blood of humans is approximately 3.4 days during which the peptide is usually protected from degradation by LDL and HDL. (Infection and immunity, November 1999, p. 6084-6089).

If administered orally, the cathelicidin analog or peptide can be delivered to the gastro intestinal tract (GIT). Peptides are usually delivered by injection or infusion due to their limited bioavailability and stability when delivered by other routs. The major problems to overcome in the development of oral peptide delivery are enzymatic degradation and denatuartion in the GIT environment and their poor penetration through physiological barriers (E. C. Lavelle et al. Vaccine 15 (1997), pp. 1070-1078). However, microencapsulation technologies using synthetic polyesters such as poly(L-lactide) (L.PLA) and copolymers such as poly(D,L-lactide co-glycolide) (PLG), used for the delivery of drugs to humans and are now being considered for the delivery of oral vaccines and peptides (M. Manocha et al Vaccine 23 (2005) (48-49), pp. 5599-5617). The objective is an oral formulations for the delivery of a peptidic agent that needs to be delivered and act in the GIT. This objective is achieved by encapsulation of the peptide into nanoparticles made of PLA or other pharmaceutically acceptable carriers. These nanoparticles will protect the peptide from deterioration in the GIT and will allow adhesion and penetration to the GI mucosal tissue and being released in its active form. Such formulations should be in a nanometer scale where the peptide is fully protected when in the GI fluid but being able to release the peptide within the GI mucosal tissue after absorption.

Two types of systems has been developed, encapsulation in PLA based polymer using the Liposphere technology and stereointeraction of the peptide with stereoregular PLA. The first system is based on the formation of PLA nanoparticles coated with phospholipids by emulsion evaporation method. The second system is based on a physical interaction between the peptide and a common biodegradable stereoregular PLA. In both methods, PLA based polymers are used. These polymers are FDA approved for the delivery of drugs as well as peptides and proteins. In this technology, the peptide is dissolved in a safe solvent along with the polymer (D-PLA) which upon mixing the solution, a precipitate of the peptide-PLA sterocomplex is formed. The precipitate can be of nanometer scale and contain a high load of the peptide. The peptide is released from the streocomplex as a result of hydrolysis of the PLA chain that intertwined along the peptide chain. This system has been investigated extensively for the injectable delivery of insulin, somatostatin and LHRH for extended release of weeks after injection. (Macromol Biosci. 2006 Dec. 8; 6(12):1019-25, J Control Release 2005 Oct. 20; 107(3):474-83, Biomaterials. 2002 November; 23(22):4389-96, Macromol Biosci. 2006 Dec. 8; 6(12):977-90)

As is described in the examples section which follows, in vivo mouse models show by implication that administering 3 doses per week of a cathelicidin regulator of the present invention to the subject (IP) with an inter dose interval of about 2.5 days can be used for effectively treating a disease such as Collagen Induced arthritis or EAE or multiple sclerosis or obesity of insulin resistance in a human subject.

Disease treatment may be effected via polytherapy by administration of the regulator in conjunction with Vitamin D3, calcitriol analogs, or peptide inhibitors such as protease inhibitors, the serpin serine proteinase inhibitory components (alpha-1 PI) and alpha −1 antichymotrypsin (Panyutich, A V. et al., 1995. Am. J. Respir. Cell Mol. Biol. 12:351-357), BAPTA-AM (an intracellular Ca(2+) chelating agent), pertussis toxin and U-73122 (a phospholipase C inhibitor; Niyonsaba, F. et al., 2001. Eur. J. Immunol. 31:1066-1075), T-cell targeted therapies, monoclonal antibody against chemokine tumor necrosis factor and cytokine targeted therapies, fibroblast growth factor inhibitors. For example, topical treatments may advantageously include cell proliferation regulators such as retinoid—vitamin A—analog which modulates or changes the cellular differentiation of the epidermis. Such polytherapy may be effected using anti-inflammatory drugs/treatments as a precautionary measure against relapse of psoriasis or other auto-immune disease. Such drugs/treatments include tazarotene, methotrexate, acitretin, bexarotene, ploralem, etretinate, corticosteroid creams and ointments, synthetic vitamin D3, IL-10, IL-4 and IL-1RA (receptor antagonist).

A cathelicidin inhibitor/vitamin D combination is particularly claimed as a treatment modality for cancer. This is because whereas vitamin D pathway can skew cancer cells into a desired differenciating state, cathelicidin, which is also expressed via the vitamin D pathway, skews cancer cells into the undesired proliferative state. Thus the maximum desired differentiating non-proliferating pathway is achieved.

To enable treatment of the disease, the regulator is preferably included as an active ingredient in a pharmaceutical composition which includes a suitable carrier and which is suitably packaged and labeled for treatment of the disease.

The regulator according to the present invention can be administered to a subject per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of active ingredients to an organism.

Herein the term "active ingredients" refers to the regulator of the present invention accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered active ingredients. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, transnasal, intestinal or parenteral delivery, including intramuscular, subcutaneous and intramedullary injections as well as intrathecal, direct intraventricular, intravenous, inrtaperitoneal, intranasal, or intraocular injections.

Alternately, one may administer the pharmaceutical composition in a local rather than systemic manner, for example, via injection of the pharmaceutical composition directly into a tissue region of a patient.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated as described above using PLA based polymers or can be formulated readily by combining the active ingredients with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active ingredient doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the active ingredients and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions. Cream solutions can include any lipids or organic alcohols or chemicals including for example benzyl alcohol, macrogol, hexylene glycol, carbomer, ascorbic acid, butyl hydroxyainisole, butyl hydroxytoluene, disodium edentate, water, trometamol, poxoamer.

Alternatively, the active ingredients may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

It should be understood that by administering a peptide of the invention it is meant administering a peptide of the invention or a pharmaceutically acceptable salt thereof or other pharmaceutically acceptable form thereof.

Pharmaceutical compositions suitable for use in context of the present invention include compositions wherein the active ingredients are contained in an amount effective to achieve the intended purpose. More specifically, a therapeutically effective amount means an amount of active ingredients (regulator of the present invention) effective to prevent, alleviate or ameliorate symptoms of a disorder (e.g., psoriasis or a carcinoma) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide plasma or brain levels of the active ingredients which are sufficient to achieve a desired therapeutic effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredients. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as if further detailed above.

Thus, the present invention provides an article of manufacture which comprises packaging material identified for treatment of the disease, and a pharmaceutical composition which includes a pharmaceutically acceptable carrier and, as an active ingredient, the regulator.

Preferably, the pharmaceutical composition is formulated as a solution, suspension, emulsion or gel.

Preferably, the pharmaceutically acceptable carrier is selected so as to enable administration of the pharmaceutical composition via a route selected from the group consisting of the topical, intravenous, intranasal, transdermal, intradermal, oral, buccal, parenteral, rectal and inhalation route.

Preferably, the pharmaceutical composition is composed so as to enable exposure of an affected cell/tissue of the subject having the disease, to the regulator at a suitable concentration, as described hereinabove, for treating the disease.

Preferably, the pharmaceutical composition is further identified for administration to the subject according to a suitable regimen, as described hereinabove.

Thus, the present invention provides a method of identifying a compound capable of treating autoimmune or inflammatory diseases by using a method of regulating the biological process in a cell/tissue involved in disease. The method is effected in a first step by exposing the cell/tissue to a test compound which is: a compound capable of decreasing or increasing an activity and/or level of an antimicrobial peptide (AMP) and/or AMP-like molecule (AML); and/or which is itself the AMP and/or AML. In a second step, the method is effected by evaluating a capacity of the test compound to regulate the biological process in the cell and/or tissue. In particular, the method involves the regulation of the AMP cathelicidin or by using the cathelicidin peptide or its analog or fragments.

It will be appreciated that the method of identifying the compound can be used for screening a plurality of compounds so as to identify a compound having a desired capacity for regulating a biological process.

The method is preferably used to identify a compound capable of regulating a biological process as described hereinabove with respect to the method of the present invention of regulating a biological process.

Preferably, the test compound is a regulator as described hereinabove with respect to the method of the present invention of regulating a biological process.

The method is preferably used to identify a compound capable of regulating the biological process in the cell/tissue as described hereinabove with respect to the method of the present invention of regulating a biological process, and as described in the Examples section which follows. As is described hereinabove with respect to the method of regulating the biological process, and in the Examples section which follows, the method is preferably employed for identifying a compound which is capable of: inducing growth in an epithelial, bone cells, osteoclasts or osteoblasts, nerve, synovial cell/tissue, beta cell, skin, keratinocytic and/or gastrointestinal cell/tissue; inhibiting growth in a tumor, epithelial, skin, keratinocytic and/or bone cells, osteoclasts or osteoblasts, nerve, synovial cell/tissue, beta cell, gastrointestinal cell/tissue; inhibiting angiogenesis/endothelial cell/tissue growth; inhibiting metastasis in a tumor cell/tissue; correcting dysregulated balance of proliferation/differentiation in an epithelial, keratinocytic and/or skin cell/tissue; and/or inhibiting inflammation in an epithelial, keratinocytic an/or skin cell/tissue.

The identification method may advantageously be performed using high-throughput methodology. Ample guidance for practicing relevant high-throughput methods is provided in the literature of the art (refer, for example, to U.S. Patent Application No. 20030044907).

The test compound may be exposed to the cell/tissue in any of various ways. Preferably, the test compound is exposed to the cell/tissue in-vitro as described in the Examples section which follows. Alternately, the test compound may be exposed to the cell/tissue by exposing the test compound to a cultured cell/tissue.

Preferably, the cell which produces the test compound is a B-cell hybridoma. Alternately, the cell which produces the test compound may be of any of various types, depending on the application and purpose.

It will be appreciated that a B-cell hybridoma is an antibody producing cell, and hence that exposing the cell/tissue to a B-cell hybridoma can be used for identifying a B-cell hybridoma which expresses an antibody which is capable of regulating the biological process.

Exposing the cell/tissue to the test compound may be effected by providing the test compound to a subject which includes the cell/tissue (in-vivo model). Preferably providing the test compound to the test subject is effected as described hereinabove with respect to providing the regulator to a subject.

The identification method may be effected by exposing the test compound to: lesions of any of various diseases associated with bone resorption, CNS disease including multiple sclerosis, arthritis, fat cells of the obeseepithelial wounds included in the present invention; a lesion in an animal model as included in the examples of this invention; or a lesion in a human having the associated disease; a human biopsy of a normal or pathological involved lesion maintained in an organotypic culture containing plasma and lymphocytes of patients suffering from the disease having and not having polymorphism on AMPs or their genes and promoters or that are induced to express an AMP (and in particular a cathelicidin) using known technologies such as transfection (Graham F L Virology 52 (2): 456-67 m, Bacchetti S Proc Natl Acad Sci USA 74 (4): 1590-4); and/or to a cell/tissue of a disease in which the disease inductive isoforms are ApoE4 and the non inductive isoform is ApoE3.

The identification method may be effected by exposing the test compound to a human lesion biopsy grafted onto an animal (xenograft model), whereby the biopsy is taken with informed consent. The biopsy may be transplanted onto an immunodeficient mouse (for example, NIHS-bg-nu-xid or BNX). For establishing such a xenograft model, PBMCs may be isolated from the blood obtained from the biopsy donor and activated (for example, using a superantigen), and the animals injected with the activated PBMCs. Ample guidance for practicing the identification method using such animal models is provided in Examples 6-8 of the Examples section below and in the literature of the art (refer, for example, to U.S. Patent Application No. 20030044907).

Evaluation of the regulation of the biological processes encompassed by the identification method may be effected using any of various suitable methods known to the ordinarily skilled artisan. Preferably, such evaluation is performed, where relevant, as described in the Examples section which follows.

Evaluating regulation of the biological process may be effected using quantitative evaluation or lessional thickness when using an in-vivo model, cell count or histological evaluation.

Preferably, data obtained from the evaluation is processed using statistical analysis and ANOVA for maximum informativity.

According to one embodiment, exemplified by Example 3, the identification method may involve exposing the test compound to cultured microbes/bacteria and evaluating regulation of the biological process is effected by measuring survival of the microbes/bacteria. This may be effected by a colony-forming unit assay performed with *Staphylococcus aureus* (isolated from clinical sample), GAS (NZ131), and enteroinvasive *Escherichia coli* O29 as described (Porter et al, 1997). Before analysis, the concentration of the bacteria in culture will be determined by plating different bacterial dilutions. The protocol may be performed as follows. Cells are washed twice with 10 mM sodium phosphate buffer (20 mM $NaH_2PO_4.H_2O$, 20 mM $Na_2HPO_4.7H_2O$) and diluted to a concentration of 2,000,000 cells per milliliter (*S. aureus*, GAS) or 200,000 cells per milliliter (*E. coli*) in phosphate buffer. *S. aureus* and *E. coli* are incubated for 4 hours at 37 degrees centigrade with various concentrations of an AMP/AML in the presence of various concentrations of the test compound to be examined, in 50 microliters of buffer in 96 well round bottom tissue culture plates (Costar 3799, Corning inc., NY). GAS are incubated for 1 hour due to the poor ability of GAS to grow in such buffers. After incubation, the cells are diluted from 10× to 100,000×, and each of 20 ml of those solutions are plated in triplicate on tryptic soy broth (for *S. aureus*) and Todd Hewitt broth (for GAS and *E. coli*), and the mean number of colonies is determined. The number of cfu per ml is calculated, and the blocking activity of the examined test compounds to block the bactericidal activities of the AMP/AML will be calculated as follows: (cell survival after AMP/AML incubation)/(cell survival after incubation without AMP/AML)×100, which represents the percentage of cells that are alive, as compared to those which are not (cell survival after AMP/AML+test compound incubation)/(cell survival after incubation with test compound alone)×100.

All compounds identified will be screened for one or all of the following effects: their ability to inhibit or regulate the antimicrobial activity of the AMP (cathelicidin in particular) or to which they were raised against; their ability to affect the proliferation or differentiation or other cellular processes of cultured cells of the affected target tissue, originally isolated from normal or diseased individuals or models, for example HaCaT, primary human or murine keratinocytes or fibroblasts for screening for psoriasis; nerve cells, bone cells or osteoclasts or osteoblasts and the effects of the inhibitors on activation of the immune system.

Identified compounds may be further screened for their effects on organotypic cocultures and animal models so as to identify inhibitors that will be able to effectively inhibit a desired biological effect or combination of biological effects. This may include, where suitable, identifying compounds that will inhibit or regulate the effects of AMPs/AMLs on proliferation/differentiation balance but which maintain their antibacterial/antimicrobial activity.

The test compound or regulator may be any of various type of molecule, such as a small synthetic/non-polypeptidic molecule.

The test compound or regulator may advantageously be a peptide, a protein or a glycosylated protein.

Test compounds and regulators of the present invention of any of various suitable types may be obtained from a commercial chemical library such as, for example, one held by a large chemical company such as Merck, Glaxo Welcome, Bristol Meyers Squib, Monsanto/Searle, Eli Lilly, Novartis, Pharmacia UpJohn, and the like. Test compounds and regulators of the present invention of any of various suitable types may also be ordered via the World Wide Web (Internet) via companies such as Chemcyclopedia (http://www.mediabrains.com/client/chemcyclop/BG1/search.asp). Alternatively, test compounds and regulators of the present invention of any of various suitable types may be synthesized de novo using standard chemical and/or biological synthesis techniques. Ample guidance for synthesis of molecules suitable for use as test compounds or regulators of the present invention of any of various suitable types is provided in the literature of the art. For biological synthesis of molecules, such as polypeptides and nucleic acids, refer, for example to: Sambrook et al., infra; and associated references in the Examples section which follows. For guidance regarding chemical synthesis of molecules, refer, for example to the extensive guidelines provided by The American Chemical Society (http://www.chemistry.org/portal/Chemistry). One of ordinary skill in the art, such as, for example, a chemist, will possess the required expertise for chemical synthesis of suitable test compounds.

In designing small molecules capable of binding the AMP/AML, several features, such as structures of antibody, receptors, ligands, and relevant biochemical and biological data may be considered. Such features may include de novo folding design using energy minimization and molecular dynamics, and comparative modeling followed by energy minimization and molecular dynamics. These two approaches differ only in developing the trial or initial structures. The folding patterns are studied using energy minimization and molecular dynamics.

Cathelicidins or cathelicidin peptides include the hCAP-18 pro-peptide and its following fragments and/or analogs of these fragments sequences (SEQ ID NOs: 1-59) listed in order as follows:

SEQ ID 1:
fdiscdkdnkrfallgdffrkskekigkefkrivqrikdflrnlvprtes

SEQ ID 2:
discdkdnkrfallgdffrkskekigkefkrivqrikdflrnlvprtes

SEQ ID 3:
iscdkdnkrfallgdffrkskekigkefkrivqrikdflrnlvprtes

SEQ ID 4:
scdkdnkrfallgdffrkskekigkefkrivqrikdflrnlvprtes

SEQ ID 5:
cdkdnkrfallgdffrkskekigkefkrivqrikdflrnlvprtes

SEQ ID 6:
dkdnkrfallgdffrkskekigkefkrivqrikdflrnlvprtes

SEQ ID 7:
kdnkrfallgdffrkskekigkefkrivqrikdflrnlvprtes

SEQ ID 8:
dnkrfallgdffrkskekigkefkrivqrikdflrnlvprtes

SEQ ID 9:
nkrfallgdffrkskekigkefkrivqrikdflrnlvprtes

SEQ ID 10:
krfallgdffrkskekigkefkrivqrikdflrnlvprtes

SEQ ID 11:
rfallgdffrkskekigkefkrivqrikdflrnlvprtes

SEQ ID 12:
fallgdffrkskekigkefkrivqrikdflrnlvprtes

SEQ ID 13:
allgdffrkskekigkefkrivqrikdflrnlvprtes

SEQ ID 14:
llgdffrkskekigkefkrivqrikdflrnlvprtes

SEQ ID 15:
lgdffrkskekigkefkrivqrikdflrnlvprtes

SEQ ID 16:
gdffrkskekigkefkrivqrikdflrnlvprtes

SEQ ID 17:
dffrkskekigkefkrivqrikdflrnlvprtes

SEQ ID 18:
ffrkskekigkefkrivqrikdflrnlvprtes

SEQ ID 19:
frkskekigkefkrivqrikdflrnlvprtes

SEQ ID 20:
rkskekigkefkrivqrikdflrnlvprtes

SEQ ID 21:
kskekigkefkrivqrikdflrnlvprtes

SEQ ID 22:
skekigkefkrivqrikdflrnlvprtes

SEQ ID 23:
llgdffrkskekigkefkrivqrikdflrnlvprte

SEQ ID 24:
llgdffrkskekigkefkrivqrikdflrnlvprt

SEQ ID 25:
llgdffrkskekigkefkrivqrikdflrnlvpr

SEQ ID 26:
llgdffrkskekigkefkrivqrikdflrnlvp

SEQ ID 27:
llgdffrkskekigkefkrivqrikdflrnlv

SEQ ID 28:
llgdffrkskekigkefkrivqrikdflrnl

SEQ ID 29:
llgdffrkskekigkefkrivqrikdflrn

SEQ ID 30:
llgdffrkskekigkefkrivqrikdflr

SEQ ID 31:
llgdffrkskekigkefkrivqrikdfl

SEQ ID 32:
llgdffrkskekigkefkrivqrikdf

SEQ ID 33:
llgdffrkskekigkefkrivqrikd

SEQ ID 34:
llgdffrkskekigkefkrivqrik

SEQ ID 35:
llgdffrkskekigkefkrivqri

SEQ ID 36:
llgdffrkskekigkefkrivqr

SEQ ID 37:
llgdffrkskekigkefkrivq

SEQ ID 38:
llgdffrkskekigkefkriv

-continued

SEQ ID 39:
llgdffrkskekigkefkri

SEQ ID 40:
efkriv

SEQ ID 41:
kefkrivq

SEQ ID 42:
gkefkrivqr

SEQ ID 43:
igkefkrivqri

SEQ ID 44:
kigkefkrivqrik

SEQ ID 45:
ekigkefkrivqrikd

SEQ ID 46:
kekigkefkrivqrikdf

SEQ ID 47:
skekigkefkrivqrikdfl

SEQ ID 48:
skekigkefkrivqrikdflrnlvprtes

SEQ ID 49:
kskekigkefkrivqrikdflr

SEQ ID 50:
rkskekigkefkrivqrikdflrn

SEQ ID 51:
frkskekigkefkrivqrikdflrnl

SEQ ID 52:
ffrkskekigkefkrivqrikdflrnlv

SEQ ID 53:
dffrkskekigkefkrivqrikdflrnlvp

SEQ ID 54:
gdffrkskekigkefkrivqrikdflrnlvpr

SEQ ID 55:
lgdffrkskekigkefkrivqrikdflrnlvprt

In accordance with the instant invention, AMPs, compositions comprising the same, and methods of use thereof are provided. In a particular embodiment, the antimicrobial peptide has at least 90% homology with amino acid sequence fallgdffrksk.$X_1$ (SEQ ID NO: 56), wherein $X_1$ is selected from the group consisting of 0, 1, 2, 3, 4, 5, 6, 7, 8, 9, 10, 11, 12, 13, 14, 15, or 16 amino acids. The amino acid sequence of the peptides may also be in reverse orientation. In another embodiment, the antimicrobial peptide has at least 90% homology with amino acid sequence X.sub.ligkefkrivq.sub.2 (SEQ ID NO: 57), wherein $X_1$ is 0, 1, 2, 3, 4, 5, 6, 7, 8, 9, 10, 11, 12, 13, 14, 15, or 16 amino acids and $X_2$ is 0, 1, 2, 3, 4, 5, 6, 7, or 8 amino acids. In yet another embodiment, the antimicrobial peptide has at least 90% homology with amino acid sequence $X_1$ffrkskekigk$X_2$ (SEQ ID NO: 57), wherein $X_1$ is 0, 1, 2, 3, 4, 5, 6, 7, 8, 9, 10, 11, 12, 13, 14, 15, or 16 amino acids and $X_2$ is 0, 1, 2, 3, 4, 5, 6, 7, or 8 amino acids. In yet another embodiment, the antimicrobial peptide has at least 90% homology with amino acid sequence $X_1$vqrikdflrn $X_2$ (SEQ ID NO: 58) where $X_2$ is 0, 1, 2, 3, 4, 5, 6, 7 amino acids and $X_1$ is 0, 1, 2, 3, 4, 5, 6, 7, 8, 9, 10, 11, 12, 13, 14, 15, 16, 17, 18,or 19 amino acids. In yet another embodiment, the antimicrobial peptide has at least 90% homology with amino acid sequence $X_1$ gkefkrivqrikdflrn$X_2$ (SEQ ID NO: 59) where $X_2$ is 0, 1, 2, 3, 4, 5, 6, 7 amino acids and $X_1$ is 0, 1, 2, 3, 4, 5, 6, 7, 8, 9, 10, 11, 12, 13, 14, 15, 16, 17, 18 or 19 amino acids.

In another embodiment, the antimicrobial peptide has at least 60%, 70%, 80%, 90% or 95% homology (or identity) with amino acids in cathelicidin peptides from mammals as described in (Curr Issues Mol Biol. 2005 July; 7(2):179-96) namely:

RL-37: RLGNFFRKVKEKIGGGLKKVGQKIKD-FLGNLVPRTAS (SEQ ID NO: 63) Rhesus monkey, CAP18: GLRKRLRKFRNKIKEKLKKIGQKIQGLLPKLAPRTDY (SEQ ID NO: 64) Rabbit, CRAMP: GLLRKGGEKIGEK-LKKIGQKIKNFFQKLVPQPE (SEQ ID NO: 65) Mouse, rCRAMP: GLVRKGGEKFGEKLRKIGQKIKEF-FQKLALEIEQ (SEQ ID NO: 65) rat, CAP11: (GL-RKKFRKTRKRIQKLGRKIGKT-GRKVWKAWREYGQIPYPCRI (SEQ ID NO: 67)) Guinea, Canine cathelicdin: KKIDRLKELITTGGQKIGEKIRRI-GQRIKDFFKNLQPREEKS (SEQ ID NO: 68), BacS: RFRPPIRRPPIRPPFYPPFRPPIRPPIF-PPIRPPFRPPLGPFP-NH$_2$ (SEQ ID NO: 69) Cow, Bac7: RRIRPRPPRLPRPRPRPLPFPRPG-PRPIPRPLPFPRPGPRPIPRPLPFPRPGPRPIPRPL (SEQ ID NO: 70) Cow, BMAP-27: GRFKRFRKKFKKLFKKL-SPVIPLLHL-NH$_2$ (SEQ ID NO: 71) Cow, BMAP-28: GGLRSLGRKILRAWKKYGPIIVPIIRI-NH$_2$ (SEQ ID NO: 72) Cow, BMAP-34: GLFRRLRDSIRRGQQKILEKARRI-GERIKDIFR-NH$_2$ (SEQ ID NO: 73) Cow, Indolicidin: ILPWKWPWWPWRR-NH$_2$ (SEQ ID NO: 74) Cow, Dodecapeptide: RLCRIVVIRVCR (SEQ ID NO: 75) Cow, Water buffalo cath GLPWILLRWLFFR-NH$_2$ (SEQ ID NO: 76) Water buffalo, OADode: RYCRIIFLRVCR (SEQ ID NO: 77) Sheep, SMAP-29: RGLRRLGRKIAH-GVKKYGPTVLRIIRIA-NH$_2$ (SEQ ID NO: 78) Sheep, SMAP-34: GLFGRLRDSLQRGGQKILEKAERIWCK-IKDIFR-NH$_2$ (SEQ ID NO: 79) Sheep, OaBacS RFRPPIRRPPIRPPFRPPFRPPVRPPIR-PPFRPPFRPPIGPFP-NH$_2$ (SEQ ID NO: 80) Sheep, OaBac6: RRLRPRHQHFPSERPWPKPLPLPLPRPG-PRPWPKPLPLPLPRPGLRPWPKPL-NH$_2$ (SEQ ID NO: 81) Sheep, OaBac7.5: RRLRPRRPRL-PRPRPRPRPRPRSLPL-PRPQPRRIPRPILLPWRPPRPIPRPQIQPIPRWL (SEQ ID NO: 82) Sheep, OaBac11: RRLRPRRPRL-PRPRPRPRPRPRSLPLPRPK-PRPIPRPLPLPRPRPKPIPRPLPLPRPRPRRIP RPLPL-PRPRPRPIPRPLPLPQPQPSPIPRPL (SEQ ID NO: 83)

ChBac5: RFRPPIRRPPIRPPFNPPFRPPVRPPFR-PPFRPPFRPPIGPFP-NH$_2$ (SEQ ID NO: 84) Goat, eCATH-1: KRFGRLAKSFLRMRILLPRRKILLAS (SEQ ID NO: 85), eCATH-2: KRRHWFPLSFQEFLEQLRRFRDQLPFP (SEQ ID NO: 86) Horse, eCATH-3 KRFHS-VGSLIQRHQQMIRDKSEATRHGIRIITRPKLLLAS (SEQ ID NO: 87), PR-39: RRRPRPPYLPRPRPPPFFP-PRLPPRIPPGFPPRFPPRFP-NH$_2$ (SEQ ID NO: 88) Pig, AFPPPNVPGPRFPPPNFPGPRFPPPNF-PGPRFPPPNFPGPRFPPPNFPGPPFPPPIFPGPWF PPPP-PFRPPPFGPPRFP-NH$_2$ (SEQ ID NO: 89) Pig, Sheep, Prophenin-2: AFPPPNVPGPRFPPPNVPGPRFPPPNF-PGPRFPPPNFPGPRFPPPNFPGPPFPPPIFPGPWF PPPP-PFRPPPFGPPRFP-NH$_2$ (SEQ ID NO: 90) Pig, Protegrin-1: RGGRLCYCRRRFCVCVGR-NH$_2$ (SEQ ID NO: 91) Pig, RGGRLCYCRRRFCICV-NH$_2$ (SEQ ID NO: 92) Pig, Protegrin-3: RGGGLCYCRRRFCVCVGR-NH$_2$ (SEQ ID NO: 93) Pig, Protegrin-4: RGGRLCYCRGWICFCVCVGR-NH$_2$ (SEQ ID NO: 94) Pig, Protegrin-5: RGGRLCYCRPRFCVCVGR-NH$_2$ (SEQ ID NO: 95) Pig, PMAP-23: RIIDLLWRVRRPQKPKFVTVWVR (SEQ ID NO: 96) Pig, PMAP-36: GRFRRLRKKTRKRLKKIGKVLKWIP-PIVGSIPLGC-NH$_2$ (SEQ ID NO: 97) Pig,

PMAP-37: GLLSRLRDFLSDRGRRLGEKIERI-GQKIKDLSEFFQS (SEQ ID NO: 98)

chCATH-B1: (Proc Natl Acad Sci USA. 2007 Sep. 18; 104(38):15063-8) chicken,

Canine cathelicidin (K9CATH): (Dev Comp Immunol. 2007; 31(12):1278-96),

Fowlicidin-3: (FEBS J. 2007 January; 274(2):418-28.), (J Biol Chem. 2006 Feb. 3; 281(5):2858-67), (Immunogenetics. 2004 June; 56(3):170-7.) chicken, CMAP27: (Vet Immunol Immunopathol. 2005 Jul. 15; 106 (3-4):321-7), Fish (cathelicidin from Atlantic cod and Atlantic salmon) Maier V H et al. Mol Immunol. 2008 Jul. 7.

Peptides with enhanced LPS neutralization and reduced pro-inflammatory activity are also included. Such peptides, for example 18-mer LLKKK or GKE and P60, P60.4, P60.4-Ac, CAP11 (cationic antibacterial polypeptide of 11 kDa), CAP18, GSLL-39, SMAP-29, and others as well as methods of discovering such peptides are disclosed in CLINICAL AND DIAGNOSTIC LABORATORY IMMUNOLOGY September 2002, p. 972-982 (18-mer LLKKK),ANTIMICROBIAL AGENTS AND CHEMOTHERAPY, September 2006, p. 2983-2989 Vol. 50, No. 9 (GKE), Laryngoscope. 2008 May; 118(5):816-20, Inflamm Res. 2004 November; 53(11):609-22, Antimicrob Agents Chemother. 2005 July; 49(7):2845-50, Protein Expr Purif. 2004 September; 37(1): 229-35, Int J Antimicrob Agents. 2004 June; 23(6):606-12, Am J Respir Crit Care Med. 2004 Jan. 15; 169(2):187-94, Eur J Biochem. 2002 February; 269(4):1181-9, Surgery. 1995 June; 117(6):656-62, Prog Clin Biol Res. 1995; 392:317-26, p e p t i d e s 27(2006) 649-660 (P60, P60.4, P60.4-Ac), and P18 as in Biotechnol Lett (2008) 30:1183-1187 and are all incorporated by reference herein. In particularly, such peptides having LPS neutralizing activity are included for the treatment of metabolic diseases, obesity and insulin resistance as is demonstrated with cathelicidin in example 4 below.

Treatment using analogs of these above peptides, peptide fragments and proteins can be formed by modification as described below so as to make the analog (modified cathelicidin peptide or modified peptide fragment) more stable in blood (as described below) while preventing their degradation into their pro-inflammatory fragments by extracellular endogenous protease. Methods of evaluating and discovering suitable analogs or fragments of cathelicidin and other AMPs can, for example, be through the use of assays as disclosed in example 9 below.

Many different analogs of the above fragments can be made as for example as described in U.S. Pat. No. 4,242,256. There Compounds being analogs of a dipeptide in which the nitrogen atom of the linking amide group of the dipeptide is replaced by trivalent group and in which, optionally, the carbonyl function of this linking group is replaced by the divalent group—CH.sub.2—are of value in the synthesis of isosterically modified peptides.

As used herein, the term "peptide" includes native peptides (either degradation products, synthetically synthesized peptides or recombinant peptides) and peptidomimetics (typically, synthetically synthesized peptides), such as peptoids and semipeptoids which are peptide analogs, which may have, for example, modifications rendering the peptides more stable while in a body or more capable of penetrating into target cells. Such modifications include, but are not limited to N terminus modification, C terminus modification, peptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992).

Peptide bonds (—CO—NH—) within the peptide may be substituted, for example, by N-methylated bonds (—N(CH3)-CO—), ester bonds (—C(R)H—C—O—O—C(R)—N—), ketomethylen bonds (—CO—CH2-), α-aza bonds (—NH—N(R)—CO—), wherein R is any alkyl, e.g., methyl, carba bonds (—CH2-NH—), hydroxyethylene bonds (—CH(OH)—CH2-), thioamide bonds (—CS—NH—), olefinic double bonds (—CH=CH—), retro amide bonds (—NH—CO—), peptide derivatives (—N(R)—CH2-CO—), wherein R is the "normal" side chain, naturally presented on the carbon atom.

These modifications can occur at any of the bonds along the peptide chain and even at several (2-3) at the same time.

Natural aromatic amino acids, Trp, Tyr and Phe, may be substituted for synthetic non-natural acid such as TIC, naphthylelanine (Nol), ring-methylated derivatives of Phe, halogenated derivatives of Phe or o-methyl-Tyr.

In addition to the above, the peptides of the present invention may also include one or more modified amino acids or one or more non-amino acid monomers (e.g. fatty acids, complex carbohydrates etc).

As used herein in the specification and in the claims section below the term "amino acid" or "amino acids" is understood to include the 20 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids.

The peptides of the present invention can be utilized in a linear or cyclic form.

A peptide can be either synthesized in a cyclic form, or configured so as to assume a cyclic structure under suitable conditions.

For example, a peptide according to the teachings of the present invention can include at least two cysteine residues flanking the core peptide sequence. In this case, cyclization can be generated via formation of S-S bonds between the two Cys residues. Side-chain to side chain cyclization can also be generated via formation of an interaction bond of the formula —(—CH2-)n-S—CH-2-C—, wherein n=1 or 2, which is possible, for example, through incorporation of Cys or homoCys and reaction of its free SH group with, e.g., bromoacetylated Lys, Orn, Dab or Dap. Furthermore, cyclization can be obtained, for example, through amide bond formation, e.g., by incorporating Glu, Asp, Lys, Orn, di-amino butyric (Dab) acid, di-aminopropionic (Dap) acid at various positions in the chain (—CO—NH or —NH—CO bonds). Backbone to backbone cyclization can also be obtained through incorporation of modified amino acids of the formulas H—N((CH2)n-COOH)—C(R)H—COOH or H—N((CH2)n-COOH)—C (R)H—NH2, wherein n=1-4, and further wherein R is any natural or non-natural side chain of an amino acid.

Depending on the application and purpose, any of various AMPs/AMLs or combinations of different AMPs/AML may be employed and/or regulated so as to practice the various embodiments of the present invention. Numerous examples of AMPs/AMLs suitable for use in the present invention are listed on the Internet/World Wide Web at http://www.bbcm.units.it/~tossi/pag1.htm, and are described hereinbelow.

Examples of AMPs/AMLs include defensins, cathelicidins, and thrombocidins (alternately termed "platelet microbicidal proteins [PMPs]").

Examples of defensins include alpha-defensins, beta-defensins, and neutrophil defensins.

Examples of alpha-defensins include alpha-defensin-1 to -6 (Mol Immunol. 2003 November; 40(7):463-7; J Clin Invest. 1985 October; 76(4):1427-35).

Examples of beta-defensins include beta-defensin-1 (Genomics. 1997 Aug. 1; 43(3):316-20; Biochem Biophys Res Commun. 2002 Feb. 15; 291(1):17-22; FEBS Lett. 1995 Jul. 17; 368(2):331-5; Paulsen F et al., J Pathol. 2002 November; 198(3):369-77), beta-defensin-2 (Biochemistry. 2001 Apr. 3; 40(13):3810-6; Gene. 1998 Nov. 19; 222(2):237-44; Paulsen F et al., J Pathol. 2002 November; 198(3):369-77), beta-defensin-3 (Cell Tissue Res. 2001 November; 306(2):257-64; J Biol Chem. 2002 Mar. 8; 277(10):8279-89. Epub 2001 Dec. 11; J Biol Chem. 2001 Feb. 23; 276(8):5707-13; Paulsen F et al., J Pathol. 2002 November; 198(3):369-77), beta-defensin-4 (J Immunol. 2002 Sep. 1; 169(5):2516-23), beta-defensin-5 (Am J Pathol. 1998 May; 152(5):1247-58; J Biol Chem. 1992 Nov. 15; 267(32):23216-25), and beta-defensin-6 (FEBS Lett. 1993 Jan. 4; 315(2):187-92; Crit Care Med. 2002 February; 30(2):428-34).

Beta-defensins include those encoded by five conserved beta-defensin gene clusters identified using a computational search strategy (Schutte B C. et al., 2002. Proc Natl Acad Sci USA. Feb. 19; 99(4):2129-33).

Examples of neutrophil defensins include neutrophil alpha-defensins and neutrophil beta-defensins.

Examples of neutrophil alpha-defensins include neutrophil alpha-defensin-1/human neutrophil peptide (HNP)-1 (J Clin Invest. 1985 October; 76(4):1436-9; Paulsen F et al., J Pathol. 2002 November; 198(3):369-77), neutrophil alpha-defensin-2/HNP-2 (J Clin Invest. 1985 October; 76(4):1436-9; Paulsen F et al., J Pathol. 2002 November; 198(3):369-77), neutrophil alpha-defensin-3/HNP-3 (J Clin Invest. 1985 October; 76(4):1436-9; Paulsen F et al., J Pathol. 2002 November; 198(3):369-77), neutrophil alpha-defensin-4/HNP-4 (Mol Immunol. 2003 November; 40(7):463-7), human defensin-5 (HD-5; D. E. Jones and C. L. Bevins, J. Biol. Chem. 267 (1992), pp. 23216-23225; J Biol Chem. 1992 Nov. 15; 267(32):23216-25; Mol Immunol. 2003 November; 40(7):469-75; Quayle A J et al., Am. J. Pathol. 1998, 152:1247-1258; FEBS Lett. 1993 Jan. 4; 315(2):187-92; D. E. Jones and C. L. Bevins, FEBS Lett. 315 (1993); Paulsen F et al., J Pathol. 2002 November; 198(3):369-77), and human defensin-6 (HD-6; Mol Immunol. 2003 November; 40(7):463-7), human defensin-5 (HD-5; D. E. Jones and C. L. Bevins, J. Biol. Chem. 267 (1992), pp. 23216-23225; J Biol Chem. 1992 Nov. 15; 267(32):23216-25; Mol Immunol. 2003 November; 40(7):469-75; Quayle A J et al., Am. J. Pathol. 1998, 152:1247-1258; FEBS Lett. 1993 Jan. 4; 315(2):187-92; D. E. Jones and C. L. Bevins, FEBS Lett. 315 (1993); Paulsen F et al., J Pathol. 2002 November; 198(3):369-77).

Examples of cathelicidins include LL-37/hCAP18 (LL-37) in humans (Curr Drug Targets Inflamm Allergy. 2003 September; 2(3):224-31; Eur J Biochem. 1996 Jun. 1; 238(2): 325-32; Paulsen F et al., J Pathol. 2002 November; 198(3): 369-77). LL-37 is a 37 amino acid residue peptide corresponding to amino acid residue coordinates 134-170 of its precursor hCAP18/human cathelicidin antimicrobial peptide protein (GenBank: ACCESSION NP_004336; VERSION NP_004336.2 GI:39753970; REFSEQ: accession NM_004345.3). The proliferation and angiogenesis pathway of LL-37 can be inhibited using pertussis toxin, an inhibitor of G-protein coupled receptors (Koczulla, R. et al., 2003. J. Clin. Invest 111:1665-1672). Similar AMPs/AMLs are listed in the following patent applications: US 2003120037, US 200309626, US20020141620, US20020507, CA 2383172, US 20020072495 and are incorporated by reference herein. The human antibacterial cathelicidin precursor hCAP-18, is synthesized in myelocytes and metamyelocytes and localizes to specific granules in neutrophils (Blood. 1997 Oct. 1; 90(7): 2796-803).

Examples of AMP-like molecules include chemokines or fragments thereof.

Examples of such chemokines include CC chemokines and CXC chemokines Considerable overlap of chemokine and AMP functions has been demonstrated (Cole et al., 2001. J. Immunol. 167:623), and certain chemokines and defensins have actually been shown to bind to the same chemokine receptor, CCR6. Defensins and certain chemokines strikingly share similar characteristics, including size, disulfide bonding, interferon (IFN) inducibility, cationic charge, and more. Relevant similarities between chemokines and AMPs are described in the literature (refer, for example, to Durr and Peschel, 2002. Infection and Immunity 70:6515). As such various chemokines and antibodies specific for such chemokines may be employed in various applications of the present invention.

Examples of such CC chemokines include CCL1, CCL5/RANTES (Infect Immun. 2002 December; 70(12):6524-33; Eur J Biochem 1996 Apr. 1; 237(1):86-92), CCL8, CCL11, CCL17, CCL18, CCL19, CCL20/activation-regulated chemokine (LARC)/macrophage inflammatory protein-3alpha (MIP-3alpha)/Exodus-1/Scya20 (Yang D et al., Journal of Leukocyte Biology Volume 74, September 2003; 74(3): 448-55), CCL21, CCL22, CCL25, CCL27/CTACK, and CCL28 (J Biol Chem. 2000 Jul. 21; 275(29):22313-23; J Immunol. 2003 Feb. 1; 170(3):1452-61). CCL chemokines are described in Yang D et al., Journal of Leukocyte Biology Volume 74, September 2003; 74(3):448-55.

Examples of such CXC chemokines include CXCL1, CXCL2, CXCL3, CXCL4 (PF-4), CXCL7/NAP-2, CXCL8/IL-8, CXCL9 (MIG; Yang D et al., Journal of Leukocyte Biology Volume 74, September 2003; 74(3):448-55), CXCL10/IP-10 (The Journal of Immunology, 2001, 167: 623-627), CXCL11/IP-9/I-TAC (The Journal of Immunology, 2001, 167: 623-627), CXCL12/SDF-1 (Yang D et al., Journal of Leukocyte Biology Volume 74, September 2003; 74(3):448-55), CXCL13, CXCL14, connective tissue activating peptide 3 (CTAP-3; Infect Immun. 2002 December; 70(12):6524-33; Eur J Biochem 1996 Apr. 1; 237(1):86-92), and CTAP-3 precursor platelet basic protein. CXC chemokines are described in Yang D et al., Journal of Leukocyte Biology Volume 74, September 2003; 74(3):448-55.

Examples of fibrinopeptides include fibrinopeptide-A (Infect Immun. 2002 December; 70(12):6524-33; Eur J Biochem 1996 Apr. 1; 237(1):86-92), fibrinopeptide-B (Infect Immun. 2002 December; 70(12):6524-33; Eur J Biochem 1996 Apr. 1; 237(1):86-92).

Examples of AMPs/AMLs further include XCL1 (Yang D et al., Journal of Leukocyte Biology Volume 74, September 2003; 74(3):448-55), MIP-1beta (Yang D et al., Journal of Leukocyte Biology Volume 74, September 2003; 74(3):448-55).

Further examples of AMPs/AMLs include adrenomedullin (Regul Pept. 2003 Apr. 15; 112(1-3):147-52; J Biol Chem 1998 Jul. 3; 273(27):16730-8), alpha-melanocyte stimulating hormone (Cutuli M et al., J Leukoc Biol. 2000 February; 67(2):233-9; Neuroimmunomodulation-2002-2003; 10(4):208-16), an angiogenin (Nature Immunology, March 2003), angiogenin-4 (Nature Immunology, March 2003), antibacterial peptides B/enkelytin (Neuroimmunol 2000 Sep. 22; 109(2):228-35), antileukoprotease (ALP; Biochem Biophys Res Commun. 1998 Jul. 30; 248(3):904-9; Am J Respir Crit Care Med 1999 July; 160(1):283-90), a lymphokine-activated killer cell-derived antimicrobial peptide, a platelet-derived antimicrobial peptide, antimicrobial peptide PR39, an apolipoprotein, an apolipoprotein-C, apolipoprotein-C2 (Hypertens Pregnancy 2002; 21(3):199-204; Peptides. 2000 March; 21(3):327-30), apolipoprotein-C3 (Hypertens Pregnancy 2002; 21(3):199-204; Peptides. 2000 March; 21(3):327-30), an apolipoprotein-E (Hypertens Pregnancy 2002; 21(3):199-204; Peptides. 2000 March; 21(3):327-30), apolipoprotein-E2 (Brain Res 1997 Feb. 21; 749(1):135-8; Biochemistry 2002 Oct. 1; 41(39):11820-3; Eur J Clin Chem Clin Biochem 1997 August; 35(8):581-9), a bactericidal/permeability-increasing protein (Paulsen F et al., J Pathol. 2002 November; 198(3):369-77; Mol Microbiol 1995 Aug. 17: 523-31; J Biol Chem 1987 Nov. 5; 262(31):14891-4), a bone morphogenetic protein (BMP), BMP-2/4, BMP-5, buforin, calcitermin (FEBS Lett. 2001 Aug. 24; 504(1-2):5-10), a cathepsin, cathepsin B, cathepsin G, cathepsin K, a lysosomal cathepsin, a chromogranin (Blood 2002 Jul. 15; 100(2):553-9), chromogranin A (Blood 2002 Jul. 15; 100(2):553-9), chromogranin B (Blood 2002 Jul. 15; 100(2):553-9), chymase (Immunology 2002 April; 105(4):375-90), connective tissue activating peptide-3, cystatin (APMIS. 2003 November; 111(11):1004-1010; Biol Chem Hoppe Seyler 1988 May; 369 Supp1:191-7), DCD-1 (J Immunol Methods. 2002 Dec. 1; 270(1):53-62), dermicidin (Nat Immunol. 2001 December; 2(12):1133-7), elastase-specific inhibitor/SKALP (skin-derived antileucoproteinase)/elafin (Biochem Soc Trans. 2002 April; 30(2):111-5; J Invest Dermatol 2002 July; 119(1):50-5), eNAP-1, eosinophil cationic protein (Peptides. 2003 April; 24(4):523-30; J Immunol 2002 March 168:2356-64; Eur J Biochem 1996 Apr. 1; 237(1):86-92; Peptides. 2003 April; 24(4):523-30; J Exp Med 1989 Jul. 1; 170(1):163-76), ESC42, ESkine, FALL-39 (Proc Natl Acad Sci USA. 1995 Jan. 3; 92(1):195-9), Fas ligand (FasL; Berthou C et al., J Immunol. 1997 Dec. 1; 159(11):5293-300), fractalkine, a glycosaminoglycan, granulysin (Reprod Biol Endocrinol. 2003 Nov. 28; J Immunol. 2003 Mar. 15; 170(6):3154-61; Cancer Immunol Immunother. 2002 January; 50(11):604-14. Epub 2001 November; Expert Opin Investig Drugs. 2001 February; 10(2):321-9), granzyme B (Berthou C et al., J Immunol. 1997 Dec. 1; 159(11):5293-300), HAX-1, heparin binding protein/CAP37 (Paulsen F et al., J Pathol. 2002 November; 198(3):369-77; J Clin Invest 1990 May; 85(5): 1468-76), a hepcidin (J Biol Chem. 2001 Mar. 16; 276(11): 7806-10. Epub 2000 Dec. 11; Eur J Biochem 2002 April 269:2232-7), an HE2, HE2alpha (Biol Reprod. 2002 September; 67(3):804-13), an HE2alpha C-terminal fragment (Biol Reprod. 2002 September; 67(3):804-13), HE2beta1 (Biol Reprod. 2002 September; 67(3):804-13), an HE2-gene derived transcript, histatin (Antimicrob Agents Chemother 2001 December 45:3437-44; Biochem Cell Biol. 1998; 76(2-3):247-56), a histone, histone H2A, histone H-2b (Peptides. 2003 April; 24(4):523-30; J Immunol 2002 March 168:2356-64; Eur J Biochem 1996 Apr. 1; 237(1):86-92), HMG-17, HtpG, an HtpG homolog, HS1 binding protein, interleukin-8, lactoferrin (Eur J Nucl Med. 2000 March; 27(3):292-301; Paulsen F et al., J Pathol. 2002 November; 198(3):369-77; J Mammary Gland Biol Neoplasia 1996 July; 1(3):285-95), a lymphokine-activated killer (LAK) cell AMP (Hua Xi Yi Ke Da Xue Xue Bao 2002 January; 33(1):87-90), lysozyme (Paulsen F et al., J Pathol. 2002 November; 198(3):369-77; Anat Embryol (Berl) 2002 July; 205(4):315-23), a macrophage inflammatory protein (MIP), MIP-1alpha, MIP-1beta, MIP-3alpha, a mast cell granule serine proteinase (Immunology 2002 April; 105(4):375-90), a matrix metalloproteinase (MMP), MMP-2, MMP-7 (Paulsen F et al., J Pathol. 2002 November; 198(3):369-77), migration inhibitory factor (J Immunol. 1998 Sep. 1; 161(5):2383-90; Scand J Infect Dis. 2003; 35(9):573-6), MMP-9, MRP8 (Behring Inst Mitt. 1992 April; (91):126-37), MRP14 (Behring Inst Mitt. 1992 April; (91):126-37), neutrophil gelatinase-associated lipocalin (NGAL; Exp Dermatol. 2002 December; 11(6):584-91; Mol Cell. 2002 November; 10(5):1033-43), neutrophil lysozyme (Int J Antimicrob Agents. 1999 September; 13(1):47-51), an opioid peptide, perforin (Berthou C et al., J Immunol. 1997 Dec. 1; 159(11):5293-300), phospholipase A(2) (PLA(2); Peptides. 2003 April; 24(4):523-30; J Exp Med 1989 Jul. 1; 170(1):163-76), platelet basic protein (Infect Immun. 2002 December; 70(12):6524-33; Eur J Biochem 1996 Apr. 1; 237(1):86-92), platelet factor-4, psoriasin (J Histochem Cytochem. 2003 May; 51(5):675-85; Gläser R et al., J Invest Dermatol 117: 768(abstr 015)), retrocyclin (Proc Natl Acad Sci USA 2002 Feb. 19; 99(4):1813-8), secretory leukocyte proteinase inhibitor (SLPI; Shugars D C et al., Gerontology. 2001 September-October; 47(5):246-53; Biochem Soc Trans. 2002 April; 30(2):111-5; J Invest Dermatol 2002 July; 119(1):50-5), secretory phospholipase A(2) (Peptides. 2003 April; 24(4):523-30; J Immunol 2002 March 168:2356-64; Eur J Biochem 1996 Apr. 1; 237(1):86-92; Paulsen F et al., J Pathol. 2002 November; 198(3):369-77), substance P, an S100 calcium-binding protein, S100A7, S100A8, S100A9, a thymosin, thymosin beta-4 (Infect Immun. 2002 December; 70(12):6524-33; Eur J Biochem 1996 Apr. 1; 237(1):86-92; Infect Immun. 2002 December; 70(12):6524-33; Eur J Biochem 1996 Apr. 1; 237(1):86-92), thymus and activation-regulated chemokine (TARC), TL1A, tryptase (Immunology 2002 April; 105(4):375-90), ubiquicidin (Eur J Nucl Med. 2000 March; 27(3):292-301; Hiemstra P S, van den Barselaar M T et al., J Leukocyte Biol 1999; 66: 423-428; J Nucl Med 2001 May 42:788-94), and urokinase-type plasminogen activator.

The AMP/AML may any one of 28 potential candidates for defensin like peptides which were computationally discovered. (Am J Respir Cell Mol Biol. 2003 July; 29(1):71-80).

As described hereinabove, the present invention can be used to treat any of various diseases which are associated with: (i) a tumor; (ii) inflammation; (iii) a wound; (iv) autoimmunity; (v) dysregulation of growth/differentiation of a cell/tissue; (vi) dysregulation of growth/differentiation balance of a cell/tissue; and/or (vii) angiogenesis.

Examples of diseases which can be treated according to the present invention are listed in International Pub. No. WO 2004-056307.

Examples of diseases which can be treated according to the present invention are also as follows.

Examples of tumors include a skin tumor, Osteosarcoma, Ewing's sarcoma, Chondrosarcoma, Malignant fibrous histiocytoma, Fibrosarcoma, Chordoma, osteoid osteoma, osteoblastoma, osteochondroma, enchondroma, chondromyxoid fibroma, and giant cell tumor, lymphoma and multiple myeloma, a keratinocytic tumor, a gastrointestinal tumor, a carcinoma, a melanoma, a squamous cell tumor, oral squamous cell carcinoma, lymphoma, a malignant tumor, a benign tumor, a solid tumor, a metastatic tumor and a non-solid tumor.

The concentration of human beta-defensin-2 in oral squamous cell carcinoma is much higher than in normal oral epithelium (Sawaki, K. et al., 2002. Anticancer Res. 22:2103-2107). There is a genetic link between proliferation of cells and cancer. Impairment of regulation of proliferation and differentiation lead to cancer development. A developing tumor needs help from neighboring cells in order to become cancerous. Overexpression or overactivity of cytokines is involved in orchestrating these processes. Continuous assault by chronic inflammation contributes to the transformation of cells as well. Angiogenesis is an important process for cancer development. AMPs are inductors of angiogenesis (Koczulla, R. et al., 2003. J. Clin. Invest 111:1665-1672). Therefore inhibiting differentiation and proliferation as well as angiogenesis by antagonists to AMPs and cytokines can be used to treat cancer. Urokinase-type plasminogen activator (uPA), has antimicrobial properties (Gyetko, M R. et al., 2002. J. Immunol. 168:801-809) and is involved in metastatic spreading of malignant cells. The in vitro and in vivo findings suggest that alpha-defensins are frequent peptide constituents of malignant epithelial cells in renal cell carcinoma with a possible direct influence on tumor proliferation (Muller, C A. et al., 2002. Am. J. Pathol. 160:1311-1324). Certain anti-angiogenic compounds were found to have potent anticancer property in vivo experimental studies. Therefore inhibition of angiogenic AMPs such as LL-37 is one form of treatment for cancer. Matrix metalloproteinases (MMPs) are known to play an important role in extracellular matrix remodeling during the process of tumor invasion and metastasis. Overexpression of MMP-2 and MMP-9 proteins was observed in a large percentage of ESCC tumors, respectively localized in tumor cell cytoplasm and stromal elements (J Cancer Res Clin Oncol. 2003 Oct. 16).

BMP-2/4 and BMP-5 but not BMPR-IA might be involved in the metastasis of oral carcinoma cells (Overexpression of BMP-2/4, −5 and BMPR-IA associated with malignancy of oral epithelium Oral Oncol. 2001, 37:225-33.)

Examples of diseases include an idiopathic/inflammatory disease, a chronic/inflammatory disease, an acute/inflammatory disease, an inflammatory cutaneous disease, an inflammatory gastrointestinal disease, a tumor associated with inflammation, an allergic disease, an autoimmune disease, an infectious disease, a malignant disease, a transplantation related disease, an inflammatory degenerative disease, an injury associated with inflammation, a disease associated with a hypersensitivity, an inflammatory cardiovascular disease, an inflammatory glandular disease, an inflammatory hepatic disease, an inflammatory neurological disease, an inflammatory musculo-skeletal disease, an inflammatory renal disease, an inflammatory reproductive disease, an inflammatory systemic disease, an inflammatory connective tissue disease, an inflammatory neurodegenerative disease, necrosis, an inflammatory disease associated with an implant, an inflammatory hematological disease, an inflammatory eye disease, an inflammatory respiratory disease.

Examples of cutaneous/inflammatory diseases include psoriasis, dandruff, pemphigus vulgaris, lichen planus, atopic dermatitis, excema, scleroderma, dermatomyositis, alopecia, blepharitis, skin carcinoma, melanoma, squamous cell carcinoma, acne vulgaris, erythema toxicum neonatorum, folliculitis, skin wrinkles, autoimmune bullous skin disease, bullous pemphigoid, pemphigus foliaceus, dermatitis, and drug eruption.

Examples of gastrointestinal/inflammatory diseases include Crohn's disease, chronic autoimmune gastritis, autoimmune atrophic gastritis, primary sclerosing cholangitis, autoimmune achlorhydra, colitis, ileitis, chronic inflammatory intestinal disease, inflammatory bowel syndrome, chronic inflammatory bowel disease, celiac disease, an eating disorder, gallstones and a gastrointestinal ulcer.

Crohn's disease is an inflammatory bowel disease. Since the bowel is exposed to the outer environment, the importance of AMPs as part of its defense and normal cellular regulation is important, as in skin, and the activity of the AMPs plays an important role in the normal physiology as well as pathological conditions in these tissues. Abnormalities in the expression and/or activity of the AMPs will contribute to pathologies in these tissues. Paneth cells (a specific type of cell in the intestine) are required to help promote normal vessel formation in cooperation with bacteria—mice absent Paneth cells were incapable of appropriate blood vessel formation. Of note, colonization by one particular type of bacteria commonly found in normal mouse and human intestine, called Bacteroides thetaiotaomicron, or B. thetaiotaomicron, stimulated blood vessel development as efficiently as implantation of a whole microbial society. The conclusion, B. thetaiotaomicron and Paneth cells work together to stimulate postnatal blood vessel formation. The ability of AMPs to act as chemoattractants for cells of the innate- and adaptive-immune system plays an important role in perpetuating chronic inflammation in the gastrointestinal tract (Cunliffe, R N, Mahida, Y R., 2003. J Leukoc Biol. October 2 [Epub ahead of print]). The AMP LL-37, beta-defensins, human alpha-defensins, beta-defensins (including HD5), HN-6, lysozyme and secretory PLA2, TL1A, are expressed in Paneth cells and intestine, secretory epithelial cells in the small intestine (Ghosh, D. et al., 2002. Nat. Immunol. 3:583-590; Fellermann, K. et al., 2003. Eur. J. Gastroenterol. Hepatol. 15:627-634). Where alpha-defensins are overexpressed, they are chemoattract naive T and immature dendritic cells and dendritic cells and monocytes (Yang, D. et al., 2000. J. Leukoc. Biol. 68:9-14; Risso, A., 2000. J. Leukoc. Biol. 68:785-792; Territo, M C. et al., 1989. J. Clin. Invest 84:2017-2020). Human alpha-defensins as well as other AMPs contribute to local intestinal host defense as part of innate immunity and may be of major relevance in microbial infection and chronic inflammatory bowel disease (Wehkamp, J. et al., 2002. Dig. Dis. Sci. 47:1349-1355). The alpha-defensins convert an acute inflammation to a chronic inflammation by downregulating human polymorphonuclear leukocyte chemotaxis, for example, alpha-defensin-l/human neutrophil protein-1, acts as an antichemotactic agent for human polymorphonuclear leukocytes). It is known that chronic inflammation is commonly characterized by the presence of increased cell proliferation and connective tissue than exudate with the presence of lymphocytes and plasma cells rather than polymorphonuclear leukocytes. Thus, suitable regulation of such AMPs/AMLs can be used to treat diseases such as inflammatory bowel disease, Crohn's disease and ulcerative colitis.

Gastritis is an inflammatory condition of the stomach. There are two main forms of gastritis, A and B. Gastritis type A is considered to develop in an autoimmune process. In both types there is a role for infectious agents such as *Helicobacter pylori*. AMPs are involved in both processes. Defensins are involved in pathogenesis of gastritis (Bajaj-Elliott, M. et al., 2002. Gut 51:356-361). Thus, suitable regulation of such AMPs/AMLs can be used to treat diseases such as gastritis.

Examples of allergic/inflammatory diseases include asthma, hives, urticaria, a pollen allergy, a dust mite allergy, a venom allergy, a cosmetics allergy, a latex allergy, a chemical allergy, a drug allergy, an insect bite allergy, an animal dander allergy, a stinging plant allergy, a poison ivy allergy, anaphylactic shock, anaphylaxis, atopic allergy and a food allergy.

Examples of hypersensitivity include Type I hypersensitivity, Type II hypersensitivity, Type III hypersensitivity, Type IV hypersensitivity, immediate hypersensitivity, antibody mediated hypersensitivity, immune complex mediated hypersensitivity, T lymphocyte mediated hypersensitivity, delayed type hypersensitivity, helper T lymphocyte mediated hypersensitivity, cytotoxic T lymphocyte mediated hypersensitivity, TH1 lymphocyte mediated hypersensitivity, and TH2 lymphocyte mediated hypersensitivity.

Examples of cardiovascular/inflammatory and/or inflammatory hematological diseases include atherosclerosis, Takayasu's arteritis, polyarteritis nodosa, Raynaud's phenomenon, temporal arteritis, inflammatory anemia, inflammatory lymphopenia, pernicious anemia, occlusive disease, myocardial infarction, thrombosis, Wegener's granulomatosis, lymphoma, leukemia, Kawasaki syndrome, anti-factor VIII autoimmune disease, necrotizing small vessel vasculitis, microscopic polyangiitis, Churg and Strauss syndrome, pauci-immune focal necrotizing glomerulonephritis, crescentic glomerulonephritis, antiphospholipid syndrome, antibody induced heart failure, thrombocytopenic purpura, autoimmune hemolytic anemia, cardiac autoimmunity, Chagas' disease, iron-deficiency anemia, and anti-helper T lymphocyte autoimmunity.

Inflammation is part of the pathological process leading to the development of atherosclerosis. Chlamydia pneumonia as well as other various microorganisms serve as potential etiological factors, linking inflammation and atherosclerosis. Inflammation is a predisposing factor as well as a consequence of several CNS pathologies. Inflammation is part of the pathophysiologic processes occurring after the onset of cerebral ischemia in ischemic stroke, as well as other CNS pathologies such as head injury and subarachnoid hemorrhage. In addition, inflammation in the CNS or in the periphery by itself is considered as a risk factor for the triggering the development of cerebral ischemia. Endothelial cells express and secrete AMPs. Cationic antimicrobial protein of 37 kDa (CAP37) also termed heparin binding protein, originally isolated from human neutrophils, is an important multifunctional inflammatory mediator is expressed within the vascular endothelium associated with atherosclerotic plaques (Lee, T D. et al., 2002. Am. J. Pathol. 160:841-848). Human beta-defensin-2 is expressed by astrocytes and its expression is increased in response to cytokines and LPS (Hao, H N. et al., 2001. J. Neurochem. 77:1027-1035). Therefore, AMP regulation can be used for treatment or prevention of these conditions.

Anemia associated with inflammatory chronic diseases is one of the body's methods of fighting pathogens by reducing available inter cellular iron uptake of pathogens. Iron is absorbed by neutrophils. Sometimes chronic inflammation can occur without the presence of pathogens. Under chronic inflammatory conditions, cytokines induce a diversion of iron traffic leading to hypoferremia. Such as in chronic bacterial endocarditis, osteomyelitis, juvenile rheumatoid arthritis, rheumatic fever, Crohn's disease, and ulcerative colitis and Chronic renal failure. Transferrin bound iron transports to monocytes causing anemia. This "transport" is thought to be related to AMP activity. Cytokines IL-1, IL-6 and TNF-beta initiate defensin production and defensin initiate the cytokine production, the result being iron over absorption by monocytes. The regulation of iron transport by cytokines is a key mechanism in the pathogenesis of anemia of chronic disease (Ludwiczek, S. et al., 2003. Blood 101:4148-4154). Therefore, regulation of AMPs can be used to regulate iron level homeostasis. Hepcidin AMP is known to regulate iron uptake, therefore inhibiting hepcidin can be used to increase iron absorption (Nicolas, G. et al., 2002. Blood Cells Mol. Dis. 29:327-335). However, there are other AMPs indirectly involved in iron regulation such as defensin and LL-37. Since HNP-1 is a non-specific defensive peptide present in neutrophils, it plays an important role in the protection against diseases such as oral lichen planus, leukoplakia, and glossitis associated with iron deficiency (Mizukawa, N. et al., 1999. Oral Dis. 5:139-142). Likewise all cationic neutrophil derived AMPs would induce iron hypoferremia when over expressed. Therefore regulating of these AMPs can be used to treat such diseases.

Leukocyte SLPI (secretory leukocyte proteinase inhibitor (SLPI)) expression seems to be up-regulated in active Wegner's granulomatosis, therefore inhibiting its activity can be used to treat diseases such as Wegener's granulomatosis and other types of vasculitis Examples of glandular/inflammatory diseases include type I diabetes, type II diabetes, type B insulin resistance, Schmidt's syndrome, Cushing's syndrome, thyrotoxicosis, benign prostatic hyperplasia, pancreatic disease, Hashimoto's thyroiditis, idiopathic adrenal atrophy, Graves' disease, androgenic alopecia, thyroid disease, thyroiditis, spontaneous autoimmune thyroiditis, idiopathic myxedema, ovarian autoimmunity, autoimmune anti-sperm infertility, autoimmune prostatitis, Addison's disease, and Type I autoimmune polyglandular syndrome.

Diabetes mellitus is a systemic disease with several major complications affecting both the quality and length of life. One of these complications is periodontal disease (periodontitis). Periodontitis is much more than a localized oral infection. (Iacopino, A M., 2001. Ann. Periodontol. 6:125-137). When diabetes mellitus is under therapeutic control, periapical and other lesions heal as readily as in nondiabetics (Bender, I B, Bender, A B. et al., 2003. J. Endod. 29:383-389). Recent studies on diseases which involve insulin insensitivity (e.g. obesity, type 2 diabetes and atherosclerosis) also show increased cytokine production and markers of inflammation. Evidence at present favors chronic inflammation as a trigger for chronic insulin insensitivity, rather than the reverse situation. (Grimble, R F., 2002. Curr. Opin. Clin. Nutr. Metab Care 5:551-559). Recent human studies have established a relationship between high serum lipid levels and periodontitis. Possible causes are a high glucose levels (such as hyperglycemia of diabetics) with added LDL levels such as in high diabetic patients are prone to elevated low density lipoprotein cholesterol and triglycerides (LDL/TRG) even when blood glucose levels are well controlled, lead to LPS-like bondings that induce AMP overexpression. Thus, the present invention can be used to treat diabetes and diabetes related diseases such as periodontitis and diabetes associated healing deficiencies.

Proliferative retinopathy is one of the chronic complications of diabetes. The process includes the development of abnormal blood vessels that might lead to retinal detachment and blindness. LL37 and other AMPs are involved in angiogenesis (Koczulla, R. et al., 2003. J. Clin. Invest 111:1665-1672), therefore LL-37 regulation can be used to prevent the development of newly formed blood vessels and therefore for preventing diabetes related eye diseases.

Examples of hepatic inflammatory diseases include primary biliary cirrhosis, active chronic hepatitis, lupoid hepatitis, autoimmune hepatitis, and hepatic cirrhosis.

Examples of neurological inflammatory diseases include neurodegenerative disease, multiple sclerosis, Alzheimer's disease, Parkinson's disease, myasthenia gravis, motor neuropathy, Guillain-Barre syndrome, autoimmune neuropathy, Lambert-Eaton myasthenic syndrome, paraneoplastic neurological disease, paraneoplastic cerebellar atrophy, non-paraneoplastic stiff man syndrome, progressive cerebellar atrophy, Rasmussen's encephalitis, amyotrophic lateral sclerosis, Sydeham chorea, Gilles de la Tourette syndrome, autoimmune polyendocrinopathy, dysimmune neuropathy, acquired neuromyotonia, arthrogryposis multiplex, optic neuritis, spongiform encephalopathy, migraine, headache, cluster headache, and stiff-man syndrome.

With respect to multiple sclerosis (MS), defensins and lactoferrins exist in cerebrospinal fluid (CSF). These peptides have antimicrobial expression in some diseases like pneumonia and meningitis, which may trigger a pathway. It seems that pathways to MS are similar to rheumatoid arthritis where AMPs reside in the synovial fluid surrounding the joint. Peptides involved are amongst others: IP-10, defensins and lactoferrins, CAP37.

Examples of connective tissue inflammatory diseases include arthritis, rheumatoid arthritis, pyogenic arthritis, mixed connective tissue disease, cholesteatoma, relapsing polychondritis, autoimmune myositis, primary Sjogren's syndrome, smooth muscle autoimmune disease, myositis, tendinitis, a ligament inflammation, chondritis, a joint inflammation, a synovial inflammation, carpal tunnel syndrome, osteoarthritis, ankylosing spondylitis, a skeletal inflammation, an autoimmune ear disease, osteoporosis, fibromyalgia, periodontitis, and an autoimmune disease of the inner ear.

With respect to diseases such as arthritis, AMPs are expressed and produced in healthy and inflamed human synovial membranes. Deposition of the AMPs lysozyme, lactoferrin, secretory phospholipase A(2) (sPA(2)), matrilysin (MMP7), human neutrophil alpha-defensin-1,-2, and -3, human beta-defensin-1, and human beta-defensin-2 was determined by immunohistochemistry. Expression of mRNA for the AMPs bactericidal permeability-increasing protein (BPI), heparin binding protein, LL37, human alpha-defensin-5, human alpha-defensin-6, and human beta-defensin-1,-2, and -3 was analyzed by reverse transcription-polymerase chain reaction (RT-PCR). RT-PCR revealed CAP37 and human beta-defensin-1 mRNA in samples of healthy synovial membrane. Additionally, human beta-defensin-3 and/or LL37 mRNA was detected in synovial membrane samples from patients with pyogenic arthritis (PA), osteoarthritis (OA) or rheumatoid arthritis (RA). Immunohistochemistry has identified lysozyme, lactoferrin, sPA(2), and MMP7 in type A synoviocytes of all samples. Human beta-defensin-1 was only present in type B synoviocytes of some of the samples. Immunoreactive human beta-defensin-2 peptide was only visible in some inflamed samples. HNP1-3 was detected in both healthy and inflamed synovial membranes. The data suggest that human synovial membranes produce a broad spectrum of AMPs. Under inflammatory conditions, the expression pattern changes, with induction of human beta-defensin-3 in PA (LL37 in RA; human beta-defensin-3 and LL37 in OA) as well as down-regulation of human beta-defensin-1 (Paulsen, F. et al., 2002. J. Pathol. 198:369-377; Cunliffe, R N, Mahida, Y R., 2003. J Leukoc Biol. October 2 [Epub ahead of print]). Thus regulating one or more of these AMPs or their activity will inhibit the pathological process in a disease such as arthritis.

Microbial mixed keratin-biofilms in cholesteatomas are caused by AMPs which are overexpressed (Jung, H H. et al., 2003. Laryngoscope 113:432-435; Chole, R A, Faddis, B T., 2002 Arch. Otolaryngol. Head Neck Surg. 128:1129-1133), AMPs such as LL-37 or other defensins or other AMPs are involved. Therefore, suitable regulation of such AMPs can be used for treating diseases such as cholesteatomas.

Examples of inflammatory renal diseases include diabetic nephropathy.

Examples of inflammatory reproductive diseases include repeated fetal loss, ovarian cyst, or a menstruation associated disease.

Examples of inflammatory systemic diseases include systemic lupus erythematosus, systemic sclerosis, septic shock, toxic shock syndrome, Reiter's syndrome, and cachexia.

Examples of inflammatory infectious diseases include candidiasis, a fungal infection, mycosis fungoides, a chronic infectious disease, a subacute infectious disease, an acute infectious disease, a viral disease, a bacterial disease, a protozoan disease, a parasitic disease, a mycoplasma disease, gangrene, sepsis, a prion disease, influenza, tuberculosis, bacterial pneumonia, malaria, acquired immunodeficiency syndrome, chronic fatigue syndrome, and severe acute respiratory syndrome.

Examples of transplantation related/inflammatory diseases include graft rejection, chronic graft rejection, subacute graft rejection, acute graft rejection hyperacute graft rejection, rejection of an implant and graft versus host disease.

Examples of implants include a prosthetic implant, a breast implant, a silicone implant, a dental implant, a penile implant, a cardiac implant, an artificial joint, a bone fracture repair device, a bone replacement implant, a drug delivery implant, a catheter, a pacemaker, an artificial heart, an artificial heart valve, a drug release implant, an electrode, and a respirator tube.

Examples of injuries associated with inflammation include a skin wound, an abrasion, a bruise, a cut, a puncture wound, a laceration, an impact wound, a concussion, a contusion, a thermal burn, frostbite, a chemical burn, a sunburn, a desiccation, a radiation burn, a radioactivity burn, a smoke inhalation, a torn muscle, a pulled muscle, a torn tendon, a pulled tendon, a pulled ligament, a torn ligament, a hyperextension, a torn cartilage, a bone fracture, a pinched nerve and a gunshot wound.

Examples of inflammatory respiratory diseases include asthma, allergic asthma, diffuse panbronchiolitis, emphysema, idiopathic pulmonary fibrosis, cystic fibrosis, influenza, sinusitis, sinusitis and chronic obstructive pulmonary disease.

Examples of inflammatory eye diseases include dry-eye disease, phacogenic uveitis, blepharitis and sympathetic ophthalmia.

Dry eye disease is a chronic inflammatory eye disease. Is particularly an issue for post-menopausal women, the elderly, and patients with systemic diseases such as Sjogren's syndrome, rheumatoid arthritis, lupus and diabetes (37% of people with diabetes suffer from the disease and 28% of adults having the disease). Defensins act as chemokines to T-cells (Stern, M E, et al., 2002. Invest Ophthalmol. Vis. Sci. 43:2609-2614).

For identifying and classifying disease, a kit comprising a reagent useful for identifying the level of cathelicidin in blood for identifying diseases types is included. The kit is compartmentalized to receive one or more of (i) an oligonucleotide for detection of a cathelicidin or fragment thereof; or (ii) an antibody for detection of cathelicidin or a fragment thereof.

As described above, preventing binding of AMPs/AMLs to cognate receptors by using ananlogues of same AMPs that compete with binding to same receptors without inducing the disease may be used to inhibit a biological process mediated by binding of the AMP/AML to the receptor. Over 50 AMPs/AMLs and over 20 receptors thereof are involved disease pathogenesis, therefore inhibiting correct target combinations of ligand and receptors is essential for treatment of such diseases. Examples of such AMPs/AMLs and cognate receptors thereof, and examples of the types of diseases which can be treated using this approach are shown in Table 1.

Ample guidance for practicing methods and techniques of the present invention, and for obtaining and utilizing materials employed for practicing the present invention is provided in the literature of the art (refer, for example, to U.S. Patent Application No. 20030044907).

Thus, the present invention enables for the first time relative to the prior art, treatment of any of various diseases by AMPs in particular by cathelicidin. The present invention clearly shows how cathelicidin is associated with biological processes in cells/tissues such as dysregulated growth/differentiation, dysregulated growth/differentiation balance, inflammation, and angiogenesis and autoimmunity. Using AMPs/AMLs, and/or inhibitors of pro-inflammatory fragments thereof is needed for treatment of disease.

Further, in addition to treatment with AMPs, such as cathelicidin, and functional fragments and analogs thereof, the invention also provides a new medical use for the treatment of obesity and/or excess body weight that includes the administration of a therapeutically effective amount of one or more LPS neutralizing compounds selected from the group consisting of: BPI (bactericidal/permeability-increasing protein) and fragments and variations thereof such as Neuprex™ (rBPI21, opebacan) a modified recombinant fragment of BPI and Mycoprex™ (both Xoma Corporation); protegrins such as protegrin-1; lactoferrins such as lactoferricin; Nisin(s) and their variants (Mol Microbiol. 2008 July; 69(1):218-30); Heliomicin and its variants (e.g., ETD151) (International Journal of Antimicrobial Agents 25 (2005) 448-452; Biochemistry. 2001 Oct. 9; 40(40):11995-2003); magainin (Biochemistry. 2003 Oct. 28; 42(42):12251-9); Colistin (polymyxin E), Polymyxin b(polymyxin b sulfate) and polymyxin derivatives (Antimicrobial Agents Chemother. 2008 Jun. 30); Antiendotoxin antibody; Curcumin and lipopolysaccharide binding peptides; Lipid A analogs; phospholipid emulsion; and ethyl pyruvate (Curr Opin Anaesthesiol. 2008 April; 21(2):98-104). Therefore, with regards to treating obesity, diabetes and overweight, the term "cathelicidin" and the use thereof will include any of the above LPS neutralizing antimicrobials.

It is expected that during the life of this patent many relevant drug screening techniques will be developed and the scope of the phrase "method of identifying a compound" is intended to include all such new technologies a priori.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

In the examples that follow, all animal work was performed under guidelines approved by either the Hebrew University of Jerusalem Animal Care and Ethics Committee (EAE model, obesity model, insulin resistance and periodontitis model) and the University of Tennessee USA (CIA model and osteoporosis model).

Example 1

Use of cathelicidins for optimal treatment of arthritis and rheumatic diseases such as rheumatoid arthritis which are associated with inflammation, autoimmunity.

Background:

Diseases associated with inflammation, autoimmunity and/or skin cell/tissue proliferation/differentiation imbalance include numerous diseases, such as arthritis, for which no optimal therapy exists. Cathelicidin hCAP-18 pro-sequence and its active form (LL-37) is expressed in the bone marrow.

The present inventors have hypothesized that regulating such AMPs/AMLs as cathelicidin may be used for treating diseases such as arthritis. While reducing the present invention to practice, a method of using the 34a.a. cathelicidin (mCRAMP) (GLLRKGGEKIGEKLKKIGQKIKN-FFQKLVPQPEQ (SEQ ID NO: 61)) for optimal treatment in an Collagen induced arthritis mouse model of the human disease associated with inflammation, autoimmunity such as in rheumatoid arthritis, Sjogren's, scleroderma, dermatomyositis, Systemic Lupus Erythematosus, sarcoidosis was demonstrated for the first time, as described below, thereby overcoming the limitations of the prior art.

The present in-vivo experiment uses a mouse model of collagen induced arthritis.

Materials:

Antimicrobial peptides (AMPs): Synthetic peptides for the Mouse Cathelicidin mCRAMP 34a.a. was purchased from Biosight Ltd (Israel). Chick native CII purchase from Sigma or Chondrex), a1 (II) chains or CB11 fragment of CII. 10 mM acetic acid, filter sterilized with 0.2-um filter Incomplete Freund's adjuvant (IFA; e.g., Difco). Mycobacterium tuberculosis (strain H37Ra; heat-killed; available by writing to Ministry of Agriculture, Fisheries, and Food, Central Veterinary Laboratory, Weybridge, Surrey, United Kingdom). DBA/1JLacJ mice (Jackson Labs)

Methods:

The Protocol for this model is described in the publication Nature Protocols (Brand D D et al. 2007; 2(5):1269-75).

Briefly, Male DBA/1 mice, 9-11 weeks of age were used in these experiments. Mice were divided into two groups, experimental and control, and each mouse was immunized at the base of the tail with 50 μl containing 100 μg of bovine CII emulsified in complete Freund's supplemented to 4 mg/ml of heat killed mycobacterium. Mice were anesthetized during the immunization by inhaled isofluorane. On the same day as the immunization, mice also received their first injection of the vehicle (150 mM saline, control group) or experimental peptide (experimental group) at a concentration of 1.5 mg/kg. Subsequently on days 2 and 4 post immunization, the dose was reduced to 1.0 mg/kg. Starting with day 7 and through day 72, a dose of 0.8 mg/kg was used. All treatments were performed 3 times per week, on a Monday, Wednesday, and Friday schedule, and the peptide or control vehicle was administered intraperitoneally for each treatment, rotating injection areas. All mice were weighed at the beginning of the experiment in order to calculate dosage administered. Mice were weighed on days 0, 21 and 46. At day 4946, the mice were again weighed (average of 1.6 gm increase and control group had a significantly greater increase in weight than did treatment group) and dosages were adjusted accordingly.

Starting on day 11, all mice were examined 3 times per week for incidence and severity of arthritis and each arthritic limb was assigned a numerical score based on the degree of inflammation observed according to the scale below.

Severity scoring system is as described in the publication (Rosleniec E et al. Current protocols in immunology, 1997). Briefly, Score 0 No evidence of erythema or swelling. Score 1 Erythema and mild swelling confined to the tarsals or ankle joint. Score 2 Erythema and mild swelling extended from the ankle to the tarsals. Score 3 Erythema and moderate swelling extended from the ankle to the metatarsal joints. Score 4 Erythema and severe swelling encompass the ankle, foot and digits or ankylosis of the joint. In this experiment, two groups of mice (10 in treatment and 11 in control) were compared. The control group received saline in parallel with treatment group on same days as the treatment group received mCRAMP (0.8 mg/Kg) intraperitoneuly 3 times a week.

Experimental Results and Statistical Analysis:

Results of statistical analysis: A very significant difference ($p=0.0037$) between treatment and control groups in the progression of arthritis (t-test difference between mean severity score from day one since incidence until day 19 since incidence).

Arthritis Incidence—In the control group, autoimmune arthritis developed a rate and incidence considerable normal for this strain of mouse (DBA/1). The control group achieved a 100% incidence by day 44. The incidence of arthritis in the experimental group (peptide treated) was somewhat lower than the control group, and the rate of arthritis development appeared to be delayed.

Likewise, the number of paws per mouse in the treatment group was significantly lower than control at a 95% confidence limit.

Severity of Arthritis—The severity of arthritis was analyzed on the basis of degree of inflammation (scored as described above) and the number of affected limbs. As seen in the figure below, differences between the two groups were clearly observed when analyzed as mean Severity Score/Mouse. While these data are weighted somewhat by the differences in arthritis incidence, the differences in the severity appear to be even greater than the differences in incidence.

Confidence limits were drawn using a 95% t-statistic on the residual distributions obtained by subtracting Actual-Expected readings. Expected readings were obtained using a linear regression model of the true data.

Weight loss is normally found in CIA and can therefore be a factor in determining severity of disease. The weight gain of the control group was less than that of the treatment group. Therefore weight measurement were compared between days 21 and day 46 and a Mann-Witney significance test showed that the weight difference between the two samples (control vs. treatment) marked as weight on day 46 divided by weight on day 21, is marginally significant ($P<0.05$, two-tailed test). Mean weight gain (day 21 to 46) in control was 2.1% and in treatment group was 5.4%.

Results of the statistical analysis for arthritis paw severity and incidence are shown in FIGS. 1 to 6.

Conclusion and discussion: The above-described results in FIGS. 1-6 clearly demonstrate for the first time relative to the prior art, treatment of a disease using AMPs and in particular, cathelicidin. Specifically, the above described results clearly demonstrate for the first time relative to the prior art optimal in-vivo treatment in a mouse model for arthritis, which is associated with inflammation and an autoimmune disease.

Cathelicidin significantly lowers incidence rate as well as severity of arthritis in model for Collagen induced arthritis ($p=0.025$).

This experiment shows that intravenous or subcutaneous or IP injection of cathelicidin is a viable mode of treatment for arthritis, rheumatic diseases and connective tissue/inflammatory diseases include arthritis, rheumatoid arthritis, pyogenic arthritis, mixed connective tissue disease, cholesteatoma, relapsing polychondritis, autoimmune myositis, primary Sjogren's syndrome, smooth muscle autoimmune disease, myositis, tendinitis, a ligament inflammation, chondritis, a joint inflammation, a synovial inflammation, carpal tunnel syndrome, osteoarthritis, ankylosing spondylitis, a skeletal inflammation, an autoimmune ear disease, osteoporosis, fibromyalgia, periodontitis, and an autoimmune disease of the inner ear.

This experiment also shows that oral, intravenous or subcutaneous or IP injection of cathelicidin forms a viable mode of treatment for the related inflammatory systemic diseases include systemic lupus erythematosus, systemic sclerosis, septic shock, toxic shock syndrome, Reiter's syndrome, and cachexia.

Example 2

Cathelicidin for the treatment of Multiple sclerosis and CNS inflammatory disease Multiple sclerosis (MS) is an immune-mediated demyelinating disease of the central nervous system (CNS) of unknown etiology.

Cathelicidin is expressed in the CNS. In this experiment delivery of the cathelicidin was made by injection (IP).

Materials and Methods:

Protocol for Myelin Oligodendrocyte Protein (MOG)-peptide induced EAE in C57BL/6 mice.

Mice.

C57BL/6 (B6) mice were purchased from Harlan (Jerusalem, Israel). Female, 9 week old mice were used in the experiment. The mice were housed in the specific-pathogen free (SPF) animal facility of the Hebrew University and all experiments were approved by the institutional animal care and use committee (IACUC).

Induction of EAE

Emulsion preparation: MOGB35-55B peptide (MEVGW-YRSPFSRVVHLYRNGK (SEQ ID NO: 62)) 1.25 mg/ml in PBS was emulsified in complete Freund's adjuvant (CFA) supplemented with 400 µg M. tuberculosis (Mt) H37RA (Difco). Mice were immunized s.c. in the flank with 250 µg MOGB35-55B/CFA using a 25G needle.

200 ng Pertussis Toxin (Sigma) was injected i.v. at the time of immunization and 48 h later.

EAE score

EAE was scored on a scale of 0-6: 0, no impairment; 1, limp tail; 2, limp tail and hind limb paresis; 3, ≧1 hind limb paralysis; 4, full hind limb and hind body paralysis; 5, hind body paralysis and front limb paresis; 6, death.

EAE treatment

Mice were treated with cathelicidin peptide of sequence GLLRKGGEKIGEKLKKIGQKIKNFFQKLVPQPEQ (SEQ ID NO: 61) was purchased and supplied by Biosight Ltd of Karmiel, Israel and diluted in PBS, vs. PBS as a control. The cathelicidin was diluted in sterile PBS and divided to aliquots kept at −20° C. such that each aliquot was thawed once for use. Mice were treated by intraperitoneal (i.p.) injection of roughly 200 µl volume (adjusted for weight) 3 times a week (Sun-Tues-Thurs) starting the day of immunization with MOG/CFA and through day 48. Clinical EAE scores were evaluated through day 60.

Results:

Results are displayed in FIGS. 7, 8, 9,

A graph showing clinical score up to day 50 is shown as graph in FIG. 8.

Conclusion:

Cathelicidin peptide treatment lowered EAE severity and protected mice from fatal EAE observed at a late stage of the disease in control animals. The lower dose of peptide, 0.2 mg/Kg was more protective than the higher 2 mg/Kg dose.

Cathelicidin or its analogs or fragments can therefore be used as a drug for the treatment of neurological and CNS inflammatory diseases.

These include neurological/inflammatory diseases include neurodegenerative disease, multiple sclerosis, Alzheimer's disease, Parkinson's disease, myasthenia gravis, motor neuropathy, Guillain-Barre syndrome, autoimmune neuropathy, Lambert-Eaton myasthenic syndrome, paraneoplastic neurological disease, paraneoplastic cerebellar atrophy, non-paraneoplastic stiff man syndrome, progressive cerebellar atrophy, Rasmussen's encephalitis, amyotrophic lateral sclerosis, Sydeham chorea, Gilles de la Tourette syndrome, autoimmune polyendocrinopathy, dysimmune neuropathy, acquired neuromyotonia, arthrogryposis multiplex, optic neuritis, spongiform encephalopathy, migraine, headache, cluster headache, and stiff-man syndrome.

Example 3

Development of a Fully Humanized Antibody to LL-37

A fully humanized antibody Single Chain Variable Fragment (scFv) to the cathelicidin LL-37 was developed using the two-hybrid system in yeast, a technology as described in U.S. Pat. No. 6,610,472.

Briefly, a library of expression vectors was generated in yeast cells through homologous recombination; and the encoded proteins complexes with high binding affinity to their target molecule LL-37 was selected by high throughput screening in vivo or in vitro. Testing for ability to inhibit LL-37 in-vivo was performed by measuring the ability of the humanized antibody to inhibit bacterial killing by LL-37.

FIG. 10 shows a Western blot analysis of 4 different scFv developed that bind LL-37.

FIG. 11 shows the inhibitory effect of scFv on LL-37 in a bacterial killing assays. In order to find out the concentration of LL37 at which 50% of the bacteria could be killed (called "IC50"). Basically the activity protocol follows the ability of the antibody to block the antimicrobial activity of LL-37. The bacteria used was Pseudomonas that was isolated from a wound. The growth medium was LB. LL-37 was added at a concentration of 100 microgram/ml (the final volume or the reaction is 50 microliter). Blocking antibodies at 1 or 5 microliter of antibody (=1:50 or 1:10 dilutions respectively. Low antibody levels ensure a non-specific effect. A 2nd fraction from the elution with 100 mM imidazole was used.

The antibody and LL-37 mixture was incubated at room temperature for 30 minutes.

The bacteria were added (volume of 40 microliters). The mixture was incubated shaking for 3 hours at 37 degrees. At that point LB was added to maintain the growth since the volumes we used were so small in order to grow the bacteria for longer incubation times, the mixture was further incubated for additional 2-3 hours. Concentration of bacteria was estimated by optical density (OD) reading at 490.

Example 4

Cathelicidin in the treatment, diabetes and related diseases including Hyperglycemia or Hypoglycemia, hypotension, hypertension, glandular/inflammatory diseases obesity, atherosclerosis and diabetes related diseases such as periodontitis and diabetes associated healing deficiencies or wounds.

Background:

TLR4 and CD14 are the receptor for LPS and play a critical role in innate immunity. Stimulation of TLR4 activates pro-inflammatory pathways and induces cytokine expression in a variety of cell types. Inflammatory pathways are activated in tissues of obese animals and humans and play an important role in obesity-associated insulin resistance. TLR4 and CD14 are a molecular link among nutrition, lipids, and inflammation and that the innate immune system participates in the regulation of energy balance and insulin resistance in response to changes in the nutritional environment. (Hang Shi et al. The Journal of Clinical Investigation Volume 116 Number 11 November 2006) In a paper published (Diabetes 56:1761-1772, 2007), It was shown that metabolic Endotoxemia Initiates Obesity and Insulin and it was suggested that lowering plasma LPS concentration could be a potent strategy for the control of metabolic diseases including insulin resistance. Therefore, the present experiment shows that insulin resistance and thereby glucose levels can be controlled using cathelicidin and is therefore a novel drug for the treatment of diabetes and diabetes related diseases. The in-vivo mouse model used is as described in Biochemical and Biophysical Research Communications 361 (2007) 140-145, "LPS-induced biomarkers in mice: A potential model for identifying insulin sensitizers". Lipopolysaccharide (LPS)-mediated inflammatory response may modulate pathways implicated in insulin resistance (J Clin Endocrinol Metab 85: 3770-3778, 2000).

Materials and Methods:

Two groups of 6 mice were used. One group was treated with PBS and the other group with the mCRAMP cathelicidin peptide at 0.4 mg/Kg, both groups injected (IP) three times a week on Sunday Tuesday and Thursday. Both groups were fed on a high fat diet of 60% Kcal fat diet (Research Diets Inc. New Brunswick USA) for a four week period by which time under normal circumstances they would be insulin resistant. At the end of four weeks blood glucose was determined using a glucometer on blood drawn by tail-nicking of mice.

LPS was administered to C57BL/6 mice at 0.2 mg/kg. Mice were bled approximately 2 h after LPS injection (T=0). Changes in insulin dependent (or non-insulin dependent) sensitivity in regulating the glucose uptake were examined by calculating the linear slope of the fall or gain in glucose. Such a slope/gradient shows the rate of decrease of glucose over time.

(SEQ ID NO: 61)
mCRAMP sequence:
GLLRKGGEKIGEKLKKIGQKIKNFFQKLVPQPEQ.

In calculating the statistics, for each individual mouse, the glucose level at time T=2 hrs. was divided by the glucose level at time T=0 to obtain a ratio at T=2 hrs for each mouse. An average was calculated for all the ratios and a students t-test was performed.

Results:

A significant difference rate of change in glucose levels was noted (students t-test <0.05). Two hours following LPS administration, average glucose levels in the control mice rose by 5.31% whereas average glucose levels in the cathelicidin treated mice came down to 90.05% of their initial level of 2 hours previously.

The treatment group was protected from insulin insensitivity thereby leading to a reduction of glucose levels during the two hour period as compared to the control group. The control group being insulin resistant due to the high fat diet remained at high glucose level. Cathelicidin protected the treatment group mice from insulin resistance normally developed as by the control group over the four week period of high fat diet. A graphic representation of the data is shown in FIG. 12. A graphic representation of the data is shown in FIG. 12

Conclusion:

This experiment shows that intravenous or subcutaneous or IP injection of Cathelicidin, its analogs or fragments inhibits insulin resistance and hyperglacemia, as well as LPS induced disregulation of glucose levels in blood, and can therefore be used for the treatment of diseases such as metabolic diseases or a glandular/inflammatory diseases including: type I diabetes, type II diabetes, type B insulin resistance, Schmidt's syndrome, Cushing's syndrome, thyrotoxicosis, benign prostatic hyperplasia, pancreatic disease, Hashimoto's thyroiditis, idiopathic adrenal atrophy, Graves' disease, androgenic alopecia, thyroid disease, thyroiditis, spontaneous autoimmune thyroiditis, idiopathic myxedema, ovarian autoimmunity, autoimmune anti-sperm infertility, autoimmune prostatitis, Addison's disease, and Type I autoimmune polyglandular syndrome Diabetes mellitus and Type II diabetes, obesity, Hyperglycemia or Hypoglycemia, complications of diabetes including skin ulcerations, and diabetes related eye diseases such as Proliferative retinopathy Example 5

Cathelicidin in the treatment of obesity and overweight as well as related diseases such as periodontitis and diabetes associated diseases and healing deficiencies.

Background:

A high-fat diet chronically increased insulin resistance, obesity and metabolic diseases. Diabetes and obesity are two metabolic diseases characterized by insulin resistance and low-grade inflammation.

The present experiment shows that obesity can be controlled using cathelicidin or cathelicidin fragments or analogues and is therefore a novel drug for the treatment of obesity and obesity related diseases. The in-vivo mouse model used is as described in (Diabetes 56:1761-1772, 2007).

Materials and Methods:

Two experiments were performed, one on a regular diet and one on a high-fat diet:

In the First Experiment:

Briefly, mice were fed on a normal non-high-fat diet for 21 days and their average weight was monitored. Two groups of Male DBA/1 mice, 10 mice in each group (treatment & Control) with an average age of 10 weeks in each group.

Control group were injected with vehicle (150 mM saline) whilst the experimental group were injected with the cathelicidin mCRAMP at a concentration of 1.5 mg/kg on day 0. Subsequently on days 2 and 4, the dose was reduced to 1.0 mg/kg. Starting with day 7 and through to day 21, a dose of 0.8 mg/kg was used. All treatments were performed 3 times per week, on a Monday, Wednesday, and Friday schedule, and the peptide or control vehicle was administered intraperitoneally for each treatment, rotating injection areas. Results shown in FIG. 13.

(SEQ ID NO: 61)
mCRAMP sequence is:
GLLRKGGEKIGEKLKKIGQKIKNFFQKLVPQPEQ

In the Second Experiment:

Briefly, Experimental obesity was induced in C57BL/6 mice by maintaining them on a 60% Kcal fat diet (Research Diets Inc. New Brunswick USA) for a six week period.

The experiment contained 2 groups of 6 mice: Group 1: PBS, Group 2: mCRAMP cathelicidin 0.2 mg/Kg for 3 weeks and then 0.4 mg/Kg for another 3 weeks. Mice were treated by intraperitoneal injection of PBS vs. peptide (200 µl per injection) on Sunday, Tuesday, and Thursday of each week. Mice were weighed at baseline and three times a week on each day of treatment.

Results:

In the first experiment using a non-high-fat diet, and as shown in FIG. 13, mice in treatment group increased in weight at a rate of 0.0536 gm/day while in the treatment the weight gain was 0.0488 gm/day.

In the second experiment using a high-fat diet the average weight in the control was divided by the average weight in the treatment groups for each of the readings (three per week). A trend was seen in the graph plotted as seen in FIG. 14. This trend is significant when analyzing using a statistical test of linear regression and residual analysis.

Continuing the treatment to day 50, a statistically significant difference between the two groups was noted by using a students t-test (<0.05) after comparing the weights of the two groups on day 50.

Therefore, treatment over long term using cathelicidin at a normally endogenous level would significantly reduce weight in obese mice.

Conclusion:

This experiment shows that intravenous or subcutaneous or IP injection of cathelicidin is a viable mode of treatment for obesity. At a 60% Kcal diet, a dosage of 0.4 mg/Kg three times a week was enough to significantly reduce weight in obese mice and prevent obesity.

Conclusion:

This experiment shows that intravenous or subcutaneous or IP injection of cathelicidin is a viable mode of treatment for obesity and that its effect is dose dependant. At a 60% Kcal diet, a dosage of 0.4 mg/Kg three times a week was enough to significantly reduce weight in obese mice and prevent obesity.

Example 6

Use of Cathelicidin for treating osteoporosis, ankylosing spondylitis, osteoarthritis and periodontitis by preventing bone erosion or resorption.

Background: Vitamin D3, a commonly used medication for osteoporosis also induces the expression of cathelicidin through the calcitriol/VDRE. For this reason cathelicidin was studied on its effect on bone resorption, degradation or formation.

Bone erosion or degradation in rheumatoid arthritis, periodontitis and osteoarthritis is a result of persistent chronic inflammation. Likewise, in osteoporosis there exists an imbalance between bone resorption and bone formation. This imbalance is due to process by which osteoclast cell activity, the process that breaks down bone, dominates osteoblast cell activity, the process by which bone formation is performed.

Therefore the present experiment tested to see if there was any difference in the bone degradation, inflammation or resorption status between arthritic paws of control versus cathelicidin treated mice in the mouse model of collagen induced arthritis as well as between the treatment and control groups of LPS induced bone loss in periodontitis (J Clin Periodontol 2004; 31: 596-603). Also tested and observed were non-inflamed joints and bone of control versus non-inflamed treatment joints and bone.

Cathelicidin was injected (IP) into treatment mice and compared with control. Histological samples of bone taken from the ankle joints of mice paws were analyzed and osteoclasts were counted using the H&E (hematoxylin and eosin stain) Immunohistochemical staining and with TRAP staining technique (Acid Phosphatase, Leukocyte—Procedure No, 387 A from Sigma-Aldrich).

Eight groups were analyzed according to their inflammatory status:

Two groups: control and treatment groups had induced inflammation in their paws but their inflammation levels were similar.

Two further groups: control and treatment groups had no inflammation in their paws.

Two further groups: control and treatment groups had induced inflammation in their paws but their inflammation levels were dissimilar.

Two further groups: control and treatment groups having induced low grade inflammation via LPS injections (IP) were studied for bone morphology differences in mandibles.

By this method, it was possible to observe bone degradation, inflammation or resorption by monitoring osteoclast and immune or inflammatory cell activity.

Materials and Methods:

Paws from the Collagen induced arthritis (CIA) experiment were studied. In all 80 paws from 20 mice were available for study and of those, only 15 were studied according to their inflammation/arthritic severity score. The protocol for induction of the CIA is reported in experiment 1 above.

Histology:

For the detection of TRAP+ cells in histological slides of joints, amputated limbs were fixed in 1% paraformaldehyde for several weeks and washed with PBS. The tissues were decalcified by incubation in 0.5 M EDTA/PBS, pH 7.4, for 10 days, in which the EDTA solution was changed every day. Tissues were embedded in paraffin and 6 µm sections were made. Deparaffinised, rehydrated sections were either stained with haematoxylin and eosin or preincubated for 2.5 hours at 37° C. in a 12.5 mM sodium tartrate solution in 100 mM acetate buffer, pH 5.5.

Subsequently, sections were incubated for 1 hour at 37° C. in acid phosphatase substrate solution (0.05% naphthol AS-BI phosphate 50 mM sodium tartrate, 0.16% p-rosanilin, 0.16% $NaNO_2$, 25% Michaelis' 0.14 M acetate/barbital buffer, pH 5.0, in distilled water). Sections were washed with distilled water, counterstained with 0.15% Lightgreen SF Yellowish in 0.2% acetic acid, incubated for 10 s in 1% acetic acid and dried at 37° C. Red-staining cells were considered to contain TRAP, and TRAP+ multinucleated cells (three or more nuclei) were regarded as osteoclasts.

Paws having similar arthritic scores for equal lengths of time were compared for bone resorption and degradation in cathelicidin treatment group versus control group. This type of comparison rules out any influence of inflammation as a determinant of bone degradation or ankylosis leaving the differentiation status of osteoblasts and osteoclasts as the main influence.

The materials and methods used for inducing arthritic bone degradation are described for the mouse model in example 1 above. The arthritic paws of grade 3 severity index and above were obtained from this same experiment and placed in fixative for histology measurements.

Experimental Results

For observation of Osteoclasts and Inflammatory bone degradation including periodontitis, arthritis osteoarthritis, slides are stained with H&E and with TRAP. Several paws having similar severity index at equal duration were histologically examined (see table of FIG. 15. In addition, non-inflamed paws in cotrol and treatment groups were also studies (FIG. 15). Other paws having different severity index and durations were also studied. In the figures, LF=Left Front paw, RF=Right Front paw, LH=Left Hind paw, and RH=Right Hind paw.

A clear difference in erosion and resorption between treatment and control groups was noted with less degradation and less resorption observed in treatment group. Degradation or deformation was mainly seen in control group. Likewise for mice chosen as having no difference in severity index and duration of arthritic paws, there was a similar distinct difference in bone resorption/erosion between the two groups.

Figure 16:
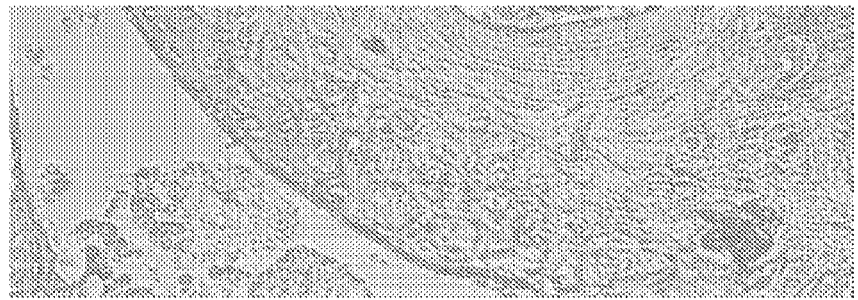
Figure 17:
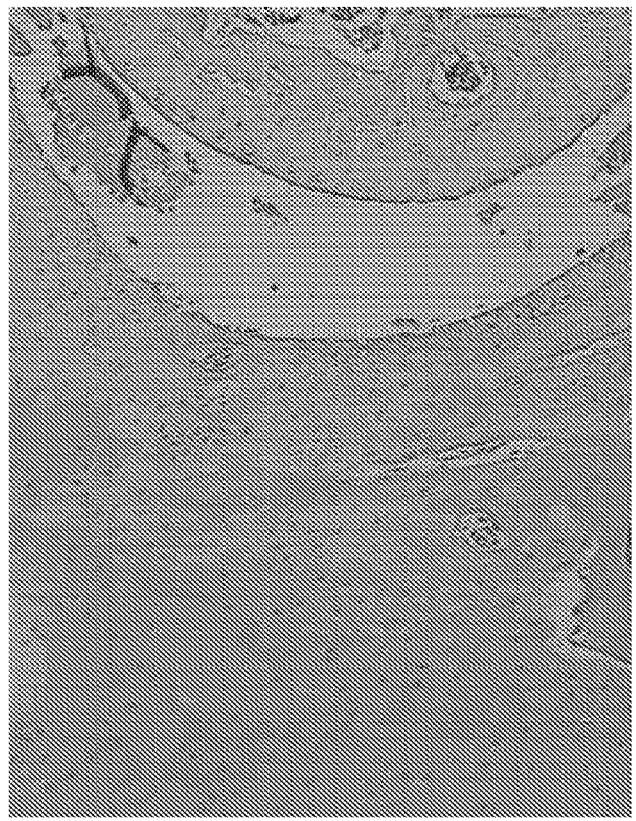

FIG. 16 is an example of histology slides between mouse 3 (Right Front) and FIG. 17 shows the H&E staining of mouse 3 (Right Front) paws.

Figure 18:
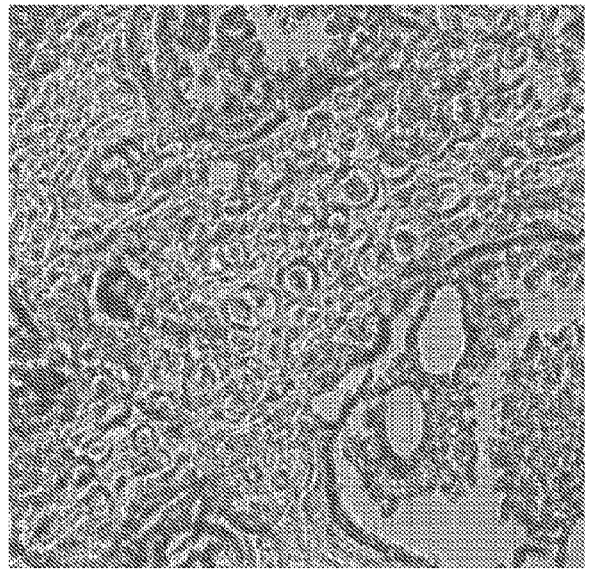

FIG. 18 shows the TRAP staining of control mouse 13 having no inflammatory sign in its paw yet still showing more osteoclasts that the inflamed mouse 3 shown above.

Figure 19:
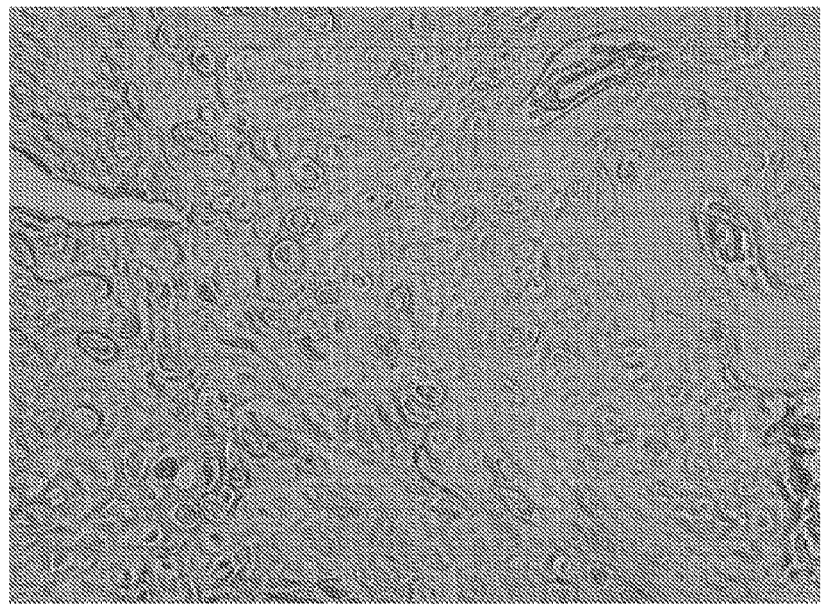

FIG. 19 shows a TRAP staining of inflamed paw of control mouse 17-Right front paw clearly showing a marked increase in osteoclasts.

Clearly, the control mouse has a higher number of active osteclasts as well as higher resorption and degradation even though both mice have the same inflammatory status.

Conclusion and Discussion:

Cathelicidin, inhibits bone erosion and deformation as found in either osteoporosis, ankylosing spondylitis, osteoarthritis and periodontitis and can therefore be used as a drug for treating these diseases.

In the present experiment, cathelicidin was delivered by IP injections. Therefore, it is obviously implied that the drug delivery of cathelicidin can be either orally using a vehicle carrier to the blood steam via the GI tract or by injection i.v. or subcutaneous injections.

The data convincingly shows that Cathelicidin is a suitable drug candidate in the treatment of osteoporosis, ankylosing spondylitis, osteoarthritis and periodontitis, Osteomyelitis, bone cancer, Osteogenesis imperfecta, Paget's disease, Osteochondroma, Osteomalacia, Osteomyelitis, Osteopetroses, Renal Osteodystrophy, Unicameral Bone Spurs, Bone Tumor, Craniosynostosis, Enchondroma, Fibrous Dysplasia, Giant Cell Tumor of Bone, Infectious Arthritis, Osteomyelitis, Klippel-Feil Syndrome, Limb Length Discrepancy, Osteochondritis Dissecans, and bone loss in periodontitis.

Example 7

Use of Cathelicidin analog and fragment for optimal treatment of diseases, such as psoriasis, which are associated with inflammation, autoimmunity and/or skin cell/tissue proliferation/differentiation imbalance and wound healing.

Background: Diseases associated with inflammation, autoimmunity and/or skin cell/tissue proliferation/differentiation imbalance include numerous diseases, such as psoriasis and dandruff, for which no optimal therapy exists. Angiogenesis and epithelialization common in psoriatic skin is enhanced by AMPs such as LL-37 (Koczulla, R. et al., 2003. J. Clin. Invest 111:1665-1672; Heilborn, J D. et al., 2003. J Invest Dermatol 120:379-389). An optimal strategy for treating such diseases would be to identify factors involved in dysregulation of skin cell/tissue proliferation/differentiation, and to use compounds capable of inhibiting the activity of such factors to treat such diseases.

Human tissue kallikreins are a family of 15 trypsin-like or chymotrypsin-like secreted serine proteases (KLK1-KLK15). Multiple KLKs have been quantitatively identified in normal stratum corneum (SC) and sweat as candidate desquamation-related proteases. Aberrant human tissue kallikrein levels levels in the stratum corneum and serum of patients with psoriasis (British Journal of Dermatology 2007 156, pp 875-883). These kallikreins are protease involved in the maturation process of cathelicidin LL-37 from its precursor hCAP-18. Inappropriate balance between various proteases can be a determining factor as to whether cathelicidin is cleaved into its pro-inflammatory or to its anti-inflammatory fragments.

As was demonstrated by the present inventor in WO 2004-056307, cathelicidin is an immune regulator in-vivo and plays a major role in psoriasis and skin inflammation. Inhibiting or regulating its activity is essential for treatment of the disease Inhibition of cathelicidin in skin inflammation was further demonstrated in psoriasis (Nature 2007 Oct. 4; 449(7162): 564-9) and in other skin inflammatory diseases such as rosacea (Nat Med. 2007 August; 13(8):975-80).

While reducing the present invention to practice, a method of using dominant negative cathelicidin peptide or fragments for optimal treatment in a human of a disease associated with inflammation, autoimmunity and/or skin cell/tissue proliferation/differentiation imbalance, such as psoriasis, was demonstrated for the first time, as described below, thereby overcoming the limitations of the prior art.

Materials and Methods:

Antimicrobial peptides (AMPs): The antimicrobial peptides used were used were the fragment cathelicidin SK29: SKEKIGKEFKRIVQRIKDFLRNLVPRTES (SEQ ID NO: 48) or GLLRKGGEKIGEKLKKIGQKIKN-FFQKLVPQPEQ (SEQ ID NO: 61) the mouse cathelicidin CRAMP (BIOSIGHT LTD, Karmiel, Israel), LLGDFFRKSKEKIGKEFKRIVQRIKDFL-RNLVPRTES (SEQ ID NO: 14) Catalogue No. 61302 LL-37 antimicrobial peptide human, AnaSpec, Inc. USA., Human Beta-Defensin-2 peptide was purchased from Sigma-Aldrich.

Human in-vivo psoriatic lesion treatment: Cathelicidin 10 ug/ml or human beta defensin-2 diluted in PBS containing 0.1% BSA, or buffer carrier was applied to lesions in a human subject in a blind trial.

Experimental Results:

Whereas the human beta defensin-2 showed a worsening of skin psoriatic legion over a seven week course of treatment, as exemplified in FIG. 20, the cathelicidins LL-37 and SK29 showed a slight improvement over the course of 5 days treatment.

Conclusion and Discussion:

Recently published material regarding rosacea has shown (Nat Med. 2007 August; 13(8):975-80) that inappropriate cathelicidin processing by endogenous protease is responsible for the disease progression of rosacea. It may well be that similar mechanisms are in effect in other diseases such as psoriasis in which case dominant negative peptide inhibitors that compete with fragments of LL-37 whithout activating the disease would form viable modes of treatment for the disease.

There is no contradiction that both inhibiting LL-37 by an antibody as was demonstrated by the previous application of the inventors in WO 2004-056307 and in the publication (Nature 2007 Oct. 4; 449(7162):564-9) and making use of LL-37 can be similarly effective. One possibility is that LL-37 may inhibit its own fragments formed by inappropriate endogenous protease action.

Example 8

Use of Cathelicidin Fragments or Analogs for the Treatment of Diabetes

In-Vitro Studies on Beta-Cells

Background: No optimal therapy exists for treatment of type 1 diabetes. An optimal strategy for treating such a disease would be to identify factors involved in inducing beta cell growth. While reducing the present invention to practice, a significant role for AMPs in driving beta cell proliferation was identified, and the capacity of cathelicidin to induce growth so as to enable optimal treatment of type 1 diabetes was demonstrated, as described below, thereby overcoming the limitations of the prior art.

Materials and Methods:

Antimicrobial peptides (AMPs): The antimicrobial peptides human cathelicidin LL-37: LLGDFFRK-SKEKIGKEFKRIVQRIKDFLRNLVPRTES (SEQ ID NO: 14) was obtained from AnaSpec, USA (Catalogue numbers: 61302). Cathelicidin at 2 µg/ml was added to the plate and compared with control.

Thymidine incorporation cell proliferation assay: Cell proliferation was evaluated by measuring [3(H)]-thymidine incorporation into DNA. Cells were pulsed with [3(H)]-thymidine (1 microcurie/mL, ICN, Irvine, Calif.) for 1 hour, at 37 degrees centigrade. After incubation, cells were washed 3 times with PBS, incubated for 15 minutes at room temperature in 5% trichloroacetic acid and solubilized in 1% triton X-100. The radioactivity incorporated into the cells was counted in the [3(H)]-window of a Tricarb liquid scintillation counter. Mean values were determined from measurements of triplicate samples under each experimental condition for each experiment. Thymidine incorporation was determined as number of disintegrations per minute (DPM) per mg of protein.

Experimental Results:

Beta cells are significantly stimulated to proliferate by AMPS: In order to investigate the effects of AMPs on beta cell growth, mouse BETATC beta cell line were chronically treated with cathelicidin, and their proliferation was monitored. As can be seen in FIG. 21, in all skin epithelial cells exposure to cathelicidin led to a slight increase in cell proliferation. This data clearly demonstrates that AMPs are involved in the pathogenesis of diabetes and in particular to type 1 diabetes with respect to cellular hyperproliferation.

Conclusion: The above-described results clearly demonstrate that AMPs, such as cathelicidin or its fragments or its analogs, are involved in driving proliferation of beta cells and therefore can be used in the treatment of diabetes by enabling the presence of an increased number of insulin secreting beta cells.

Example 9

Chemotaxis Assays

Chemotaxis assays. Cells (e.g. neutrophils, monocytes, T cells, HEK293; 25 microliters at a density of 1.0-3.0×106 cells/ml) in RPMI medium (Beit Haemek) containing 0.5% BSA (Sigma-Aldrich) are placed on the top of a 96-well ChemoTx disposable chemotaxis apparatus with a 5 micron pore size (Neuroprobe). Tenfold serial dilutions of the tested reagent in RPMI medium with or without 0.5% BSA are placed in the bottom wells of the chamber. The apparatus is incubated for 60-600 min at 37° C. in an atmosphere of 5% carbon dioxide, and the cells migrating at each concentration of chemoattractant is counted with the use of an inverted microscope.

Cells (1×107/mL) are suspended in a buffer containing 0.25% BSA, 145 mM NaCl, 5 mM KCl, 10 mM Na/MOPS, 1 mM CaCl2, 1 mM MgCl2, 10 mM glucose, 10 mM HEPES (all from Sigma-Aldrich), pH 7.4, and incubated with 2 micromolar Fura-2-AM (Molecular Probes, Eugene, Oreg.), for 40 min at room temperature. The cells are washed once, resuspended in the buffer containing 0.25% BSA, and are kept at room temperature. Just before use, aliquots of the cells (4×105) are washed and resuspended in 2 ml buffer containing 0.05% BSA in a stirred cuvette at 37° C. Measurement of intracellular Ca2+ concentration and chemotaxis assays are performed as previously described (Maghazachi, A A. et al., 1997. FASEB J. 11:765-774).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, and patent applications and sequences identified by their accession numbers mentioned in this specification are herein incorporated by reference in their entireties into the specification, to the same extent as if each individual publication, patent, or patent application or sequence identified by its accession number was specifically and individually indicated to be incorporated herein by reference. In addition, citation or identification of any reference in this application shall not be construed as an admission that such reference is available as prior art to the present invention.

What is claimed is:

1. A method for treating Rheumatoid arthritis or Osteoarthritis comprising administrating to a mammal in need thereof, a therapeutically effective amount of a cathelicidin peptide selected from mCRAMP (SEQ ID NO: 61) and LL-37 (SEQ ID NO: 14).

2. The method of claim 1, wherein the mammal is a human.

3. The method of claim 1, wherein the cathelicidin peptide is mCRAMP (SEQ ID NO:61).

4. The method of claim 1, wherein the cathelicidin peptide is LL-37 (SEQ ID NO: 14).

5. The method of claim 1, wherein the method is a method of treating Rheumatoid arthritis.

6. The method of claim 1, wherein the method is a method of treating Osteoarthritis.

* * * * *